(12) United States Patent
Regnier et al.

(10) Patent No.: US 7,449,170 B2
(45) Date of Patent: Nov. 11, 2008

(54) MATERIALS AND METHODS FOR CONTROLLING ISOTOPE EFFECTS DURING FRACTIONATION OF ANALYTES

(75) Inventors: Fred E. Regnier, West Lafayette, IN (US); Roujian Zhang, Newberry Park, CA (US)

(73) Assignee: Purdue Research Foundation, West LaFayette, IN (US)

( * ) Notice: Subject to any disclaimer, the term of this patent is extended or adjusted under 35 U.S.C. 154(b) by 894 days.

(21) Appl. No.: 10/256,326

(22) Filed: Sep. 27, 2002

(65) Prior Publication Data

US 2003/0186326 A1  Oct. 2, 2003

Related U.S. Application Data

(60) Provisional application No. 60/325,335, filed on Sep. 27, 2001.

(51) Int. Cl.
  *A61K 51/00* (2006.01)
  *G01N 24/00* (2006.01)

(52) U.S. Cl. .................... 424/1.11; 424/1.81; 424/1.89; 424/9.3; 436/173

(58) Field of Classification Search ................ 424/1.11, 424/1.81, 1.89, 9.3; 436/173
See application file for complete search history.

(56) References Cited

U.S. PATENT DOCUMENTS

| | | | |
|---|---|---|---|
| 5,393,669 A | 2/1995 | Brown | |
| 5,952,653 A | 9/1999 | Covey et al. | |
| 6,096,717 A | 8/2000 | Jarvik | |
| 6,156,527 A | 12/2000 | Schmidt et al. | |
| 6,391,649 B1 | 5/2002 | Chait et al. | |
| 6,629,040 B1 | 9/2003 | Goodlett et al. | |
| 6,670,194 B1 * | 12/2003 | Aebersold et al. | 436/173 |
| 6,852,544 B2 * | 2/2005 | Aebersold et al. | 436/173 |
| 6,864,099 B2 | 3/2005 | Regnier | |
| 6,872,575 B2 | 3/2005 | Regnier | |
| 6,905,879 B2 | 6/2005 | Qui et al. | |
| 7,045,296 B2 | 5/2006 | Parker et al. | |
| 7,052,915 B2 | 5/2006 | Aebersold et al. | |
| 7,183,116 B2 | 2/2007 | Aebersold et al. | |
| 7,183,118 B2 | 2/2007 | Aebersold et al. | |
| 2002/0037532 A1 | 3/2002 | Regnier et al. | |
| 2002/0049307 A1 | 4/2002 | Aebersold et al. | |
| 2002/0076739 A1 | 6/2002 | Aebersold et al. | |
| 2002/0119490 A1 | 8/2002 | Aebersold et al. | |
| 2002/0168644 A1 | 11/2002 | Aebersold et al. | |
| 2002/0192720 A1 | 12/2002 | Parker et al. | |
| 2003/0054570 A1 | 3/2003 | Qiu et al. | |
| 2003/0087322 A9 | 5/2003 | Aebersold et al. | |
| 2003/0092076 A1 | 5/2003 | Regnier et al. | |
| 2003/0129769 A1 | 7/2003 | Regnier | |
| 2003/0186326 A1 | 10/2003 | Regnier et al. | |
| 2004/0023306 A1 | 2/2004 | Aebersold et al. | |
| 2004/0033625 A1 | 2/2004 | Aebersold et al. | |
| 2004/0038319 A1 | 2/2004 | Aebersold et al. | |
| 2004/0110186 A1 | 6/2004 | Aebersold et al. | |
| 2004/0265810 A1 | 12/2004 | Aebersold et al. | |
| 2005/0095649 A1 | 5/2005 | Aebersold et al. | |
| 2005/0233399 A1 | 10/2005 | Aebersold et al. | |
| 2006/0008851 A1 | 1/2006 | Aebersold et al. | |
| 2006/0141528 A1 | 6/2006 | Aebersold et al. | |
| 2007/0099251 A1 | 5/2007 | Zhang et al. | |
| 2007/0202539 A1 | 8/2007 | Aebersold et al. | |
| 2007/0269895 A1 | 11/2007 | Aebersold et al. | |

FOREIGN PATENT DOCUMENTS

| | | |
|---|---|---|
| WO | WO 98/32876 A1 | 7/1998 |
| WO | WO 00/09654 A2 | 2/2000 |
| WO | WO 00/09654 A3 | 2/2000 |
| WO | WO 00/11208 A1 | 3/2000 |
| WO | WO 01/86306 A2 | 11/2001 |
| WO | WO 01/86306 A3 | 11/2001 |
| WO | WO 02/46770 A2 | 6/2002 |
| WO | WO 02/46770 A3 | 6/2002 |
| WO | WO 03/027682 A2 | 4/2003 |
| WO | WO 03/027682 A3 | 4/2003 |

OTHER PUBLICATIONS

Aebersold et al. "Mass Spectrometry in Proteomis" *Chem Rev.* 2001;101:269-295.

Amini et al., "The impact of buffers and surfactants from micellar electrokinetic chromatography on matrix-assisted laser desorption ionization (MALDI) mass spectrometry of peptides. Effect of buffer type and concentration on mass determination by MALDI-time-of-flight mass-spectrometry," *Journal of Chromatography A*, 894(1-2):345-355 (2000).

Andersen et al., "Functional genomics by mass spectrometry," *FEBS Letters*, 480:25-31 (2000).

Anderson et al., "Twenty years of two-dimensional electrophoresis: past, present and future," *Electrophoresis*, 1996;17(3):443-453.

Anderson et al., "Back to the future: The human protein index (HPI) and the agenda for post-proteomic biology," *Proteomics*, 2001;1:3-12.

Arnott et al., "Selective Detection of Membrane Proteins Without Antibodies," *Molecular & Cellular Proteomics 1.2* 2002;148-156.

Badman et al., "Cylindrical ion trap array with mass selection by variation in trap dimensions," *Anal. Chem.* 2000;72:5079-5086.

(Continued)

*Primary Examiner*—Rei-tsang Shiao
*Assistant Examiner*—Susannah Chung
(74) *Attorney, Agent, or Firm*—Meuting Raasch & Gebhardt, P.A.

(57) ABSTRACT

Compositions and methods for controlling or eliminating isotope effects during fractionation of chemically equivalent but isotopically distinct compounds. Isotope coding agents contain heavy isotopes other than deuterium. The invention facilitates intelligent data acquisiton. After sample fractionation, isotope abundance ratios are calculated using mass spectrometry, and analytes of interest are identified in real time.

14 Claims, 22 Drawing Sheets

OTHER PUBLICATIONS

Bai et al., "High performance hydrophobic interaction chromatography—A new approach to separate intermediates of protein folding," *Chinese Chemical Letters*, 8(1):67-70 (1997).

Boersma et al., "$^{19}$F NMR metabolomics for the elucidation of microbial degradation pathways of fluorophenols," *J. Ind. Microbiol. Biotechnol.* 2001;26:22-34.

Chakraborty, Asish, "Comparative Proteomics Based on Global Internal Standard Labeling Technology," Ph.D. Thesis, Purdue University, (cover date May 2002).

Chen et al., "Site-Specific Mass Tagging with Stable Isotopes in Proteins for Accurate and Efficient Protein Identification," *Anal. Chem.* 2000;72:1134-1143.

Clauser et al., "Rapid mass spectrometric peptide sequencing and mass matching for characterization of human melanoma proteins isolated by two-dimensional PAGE," *Proceedings of the National Academy of Sciences USA*, 92(11):5072-5076 (1995).

Conrads et al., "Quantitative analysis of bacterial and mammalian proteomes using a combination of cysteine affinity tags and $^{15}$N-metabolic labeling," *Anal. Chem.* 2001;73:2132-2139.

Corthals et al., "Identification of proteins by mass spectrometry," *Proteome Research: Two-Dimensional Gel Electrophoresis and Identification Methods*, selected portion available on-line, The Garvan Institute of Medical Research, Biological Mass Spectrometry and Protein Analysis Laboratory [on-line] New York, NY, Springer, 1999 [retrieved on Sep. 12, 2001]. Retrieved from the Internet: <URL: http://www.garvan.unsw.edu.au/public/corthals/book/IPMS.html>, pp. 1-17.

Corthals et al., "Chapter 10: Identification of Proteins by Mass Spectrometry," *Proteome Research: Two-Dimensional Gel Electrophoresis and Identification Methods*, Rabilloud, ed., Springer Verlag, Heidelberg, Germany, title page, publication page, and pp. 197-231 (2000).

Corthals et al., "Large-scale proteomics and its future impact on medicine," *Pharmacogenomics J.*, 2001;1:15-19.

Dass et al., "Manipulation of ion-pairing reagents for reversed-phase high-performance liquid chromatographic separation of phosphorylated opioid peptides from their non-phosphorylated analogues," *J. Chromatogaphy. A*, 1994;678:249-257.

Dormady et al., "Eliminating disulfide exchange during glutamyl endopeptidase digestion of native protein," *Journal of Chromatography A*, 864:237-245 (1999).

Dunlap et al., "Synthesis and chromatographic characterization of dextran-coated zirconia high-performance liquid chromatographic stationary phases," *Journal of Chromatography A*, 746(2):199-210 (1996).

Dwek et al., "Proteome and glycosylation mapping identifies post-translational modifications associated with aggressive breast cancer," *Proteomics* 2001;1:756-762.

Eng et al., "An Approach to Correlate Tandem Mass Spectral Data of Peptides with Amino Acid Sequences in a Protein Database," *Journal of the American Society for Mass Spectrometry*, 5(11):976-989 (1994).

Fiehn, "Combining genomics, metabolome analysis, and biochemical modeling to understand metabolic networks," *Comp. Funct. Genom.* 2001;2:155-168.

Geng et al., "Proteomics of Glycoproteins Based on Affinity Selection of Glycopeptides from Tryptic Digests," *Journal of Chromatography B*, 752:293-306 (2001).

Goodlett et al., "Protein Identification with a Single Accurate Mass of a Cysteine-Containing Peptide and Constrained Database Searching," *Analytical Chemistry*, 72(6):1112-1118 (2000).

Goodlett et al., "Differential stable isotope labeling of peptides for quantitation and de novo sequence derivation," *Rapid Commun. Mass Spectrom.* 2001;15:1214-1221.

Griffin et al., "Toward a High-Throughput Approach to Quantitative Proteomics Analysis: Expression-Dependent Protein Identification by Mass Spectrometry," *J. Am. Soc. Mass Spectrom.* 2001;12:1238-1246.

Gygi et al., "Quantitative analysis of complex protein mixtures using isotope-coded affinity tags," *Nature Biotechnology*, 17(10):994-999 (1999).

Gygi et al., "Measuring gene expression by quantitative proteome analysis," *Current Opinion in Biotechnology*, 11(4):396-401 (2000).

Gygi et al., "Mass spectrometry and proteomics," *Current Opinion in Chemical Biology*, 4(5):489-494 (2000).

Gygi et al., "Proteome analysis of low-abundance proteins using multidimensional chromatography and isotope-coded affinity tags," *Journal of Proteome Research* 2002;1:47-54.

Hsieh et al., "Automated Analytical System for the Examination of Protein Primary Structure," *Analytical Chemistry*, 68:455-462 (1996).

Hsieh et al., "Separation and Identification of Peptides in Single Neurons by Microcolumn Liquid Chromatography-Matrix-Assisted Laser Desorption/Ionization Time-of-Flight Mass Spectrometry and Postsource Decay Analysis," *Analytical Chemistry*, 70(9):1847-1852 (1998).

Ishizuka et al., "Performance of a monolithic silica column in a capillary under pressure-driven and electrodrive conditions," *Anal. Chem.* 2000;72:1275-1280.

Jensen et al., "Probing proteomics using capillary isoelectric focusing-eletrospray ionization fourier transform ion cyclotron resonance mass spectrometry," *Anal. Chem.* 1999;71:2076-2084.

Ji et al., "Strategy for qualitative and quantitative analysis in proteomics based on signature peptides," *Journal of Chromatography B*, 745:197-210 (2000).

Kaufmann et al., "Use of antibodies for detection of phosphorylated proteins separated by two-dimensional gel electrophoresis," *Proteomics* 2001;1:194-199.

Küster et al., "$^{18}$O-labeling of N-glycosylation sites to improve the identification of gel-separated glyoproteins using peptide mass mapping and database searching," *Anal. Chem.* 1999;71:1431-1440.

Kosaka et al., "Identification and C-Terminal Characterization of Proteins from Two-Dimensional Polyacrylamide Gels by a Combination of Isotopic Labeling and Nanoelectrospray Fourier Transform Ion Cyclotron Resonance Mass Spectrometry," *Analytical Chemistry*, 72:1179-1185 (2000).

Larsen et al., "Characterization of differently processed forms of enolase 2 from *Saccharomyces cerevisiae* by two-dimensional gel electrophoresis and mass spectrometry," *Electrophoresis* 2001;22:566-575.

Lee et al., "Enzymatic and Chemical Digestion of Proteins for Mass Spectrometry," *Methods in Enzymology*, 193:361-374 (1990).

Link et al., " Direct analysis of protein complexes using mass spectrometry," *Nature Biotechnology*, 17(10):676-682 (1999).

Mann et al., "Analysis of proteins and proteomes by mass spectrometry," *Ann. Rev. Biochem.* 2001;70:437-473.

Mirgorodskaya et al., "Quantitative determination of peptides and proteins by MALDI MS," *Russ. J. Bioorg. Chem.* 2000;26(9):593-602; translated from *Bioorganicheskaya khimiya*, vol. 26, No. 9. pp. 662-671 (2000).

Nelson et al., "BIA/MS of Epitope-Tagged Peptides Directly from *E. coli* Lysate: Multiplex Detection and Protein Identification at Low-Femtomole to Subfemtomole Levels," *Analytical Chemistry*, 71:2858-2865 (1999).

O'Farrell, "High Resolution Two-Dimensional Electrophoresis of Proteins," *The Journal of Biological Chemistry*, 250(10):4007-4021 (1975).

Patterson et al., "C-Terminal Ladder Sequencing via Matrix-Assisted Laser Desorption Mass Spectrometry Coupled with Carboxypeptidase Y Time-Dependent and Concentration-Dependent Digestions," *Analytical Chemistry*, 67(21):3971-3978 (1995).

Pedersen et al., "Patterns of Protein Synthesis in *E. coli*: a Catalog of the Amount of 140 Individual Proteins at Different Growth Rates," *Cell*, 14(1):179-190 (1978).

Perkin-Elmer Applied Biosystems Press Release, "PE Biosystems Obtains Exclusive License for ICAT™ Reagents for Proteomics," [online]. Applied Biosystems, Foster City, Calif., Nov. 17, 2000 [retrieved on Sep. 26, 2001]. Retrieved from the Internet: <URL:www.appliedbiosystems.com/press_releases/icat> 2 pages.

Porath et al., "Metal chelate affinity chromatography, a new approach to protein fractionation," *Nature*, 258(5536):598-599 (1975).

Porath, "Immobilized Metal Ion Affinity Chromatography," *Protein Expression and Purification*, 3(4):263-281 (1992).

Posewitz et al., "Immobilized Gallium(III) Affinity Chromatography of Phosphopeptides," *Analytical Chemistry*, 71(14):2883-2892 (1999).

Raamsdonk et al., "A functional genomics strategy that uses metabolome data to reveal the phenotype of silent mutations," *Nature Biotechnology* 2001;19:45-50.

Raj et al., "Indoles and auxins. V. Separation of 2,4-dinitrophenylthio-derivatives of naturally occurring indoles by thin layer chromatography," *Journal of Chromatography*, 44(1):199-201 (1969).

Raj et al., "Indoles and auxins. X. 2,4-Dinitrophenylsulfenyl chloride, a reagent for separation and identification of naturally-occurring indoles," *Canadian Journal of Biochemistry*, 48(6):664-670 (1970).

Regnier, Fred E., "Chip Based Systems for the Analysis of Regulation," Grant Abstract, Grant No. 1R01GM059996-01 [online]. National Institutes of General Medical Sciences, National Institutes of Health, project dates Sep. 1, 1999-Aug. 31, 2003 [retrieved on Sep. 10, 2001]. Retrieved from the Internet: URL: http.commons.cit.nih.gov/crisp3/crisp_lib.getdoc?textkey=2899517 &p_grant_num=1R01GM059996-01&p_query=ticket=78685 &p_audit_session_id=1046138&p_keywords=>, 2 pages.

Regnier, Fred E., "Chip Based Systems for the Analysis of Regulation," Grant Abstract, Grant No. 5R01GM059996-02 [online]. National Institutes of General Medical Sciences, National Institutes of Health, project dates Sep. 1, 1999-Aug. 31, 2003 [retrieved on Sep 10, 2001]. Retrieved from the Internet: URL: http.commons.cit.nih.gov/crisp3/crisp_lib.getdoc?textkey=6181543 &p_grant_num=5R01GM059996-02&p_query=ticket=78685 &p_audit_session_id=1046138&p_keywords=>, 2 pages.

Regnier et al., "Chromatography and electrophoresis on chips: critical elements of future integrated, microfluidic analytical systems for life science," *Trends in Biotechnology*, 17(3):101-106 (1999).

Regnier, Fred E., "High Speed Liquid Chromatography of," Grant Abstract, Grant No. 1R01GM025431-01 [online]. National Institutes of General Medical Sciences, National Institutes of Health, project dates Jul. 1, 1978-Jun. 30, 1980 [retrieved on Sep. 10, 2001]. Retrieved from the Internet: URL: http.commons.cit.nih.gov/crisp3/crisp_lib.getdoc?textkey=4379470 &p_grant_num=1R01GM025431-01&p_query=ticket=78685 &p_audit_session_id=1046138&p_keywords=>, 1 page.

Regnier, Fred E., "High Speed Liquid Chromatography of," Grant Abstract, Grant No. 5R01GM025431-02 [online]. National Institutes of General Medical Sciences, National Institutes of Health, project dates Jul. 1, 1978-Jun. 30, 1980 [retrieved on Sep. 10, 2001]. Retrieved from the Internet: URL: http.commons.cit.nih.gov/crisp3/crisp_lib.getdoc?textkey=4379471 &p_grant_num=5R01GM025431-02&p_query=ticket=78685 &p_audit_session_id=1046138&p_keywords=>, 1 page.

Regnier, Fred E., "High Performance Liquid Chromatography of Proteins," Grant Abstract, Grant No. 2R01GM025431-03 [online]. National Institutes of General Medical Sciences, National Institutes of Health, project dates Jul. 1, 1978-Jun. 30, 1983 [retrieved on Sep. 10, 2001]. Retrieved from the Internet: URL: http.commons.cit.nih.gov/crisp3/crisp_lib.getdoc?textkey=4130836 &p_grant_num=2R01GM025431-03&p_query=ticket=78685 &p_audit_session_id=1046138&p_keywords=>, 1 page.

Regnier, Fred E., "High Performance Liquid Chromatography of Proteins," Grant Abstract, Grant No. 5R01GM025431-04 [online]. National Institutes of General Medical Sciences, National Institutes of Health, project dates Jul. 1, 1978-Jun. 30, 1983 [retrieved on Sep. 10, 2001]. Retrieved from the Internet: URL: http.commons.cit.nih.gov/crisp3/crisp_lib.getdoc?textkey=4130837 &p_grant_num=5R01GM025431-04&p_query=ticket=78685 &p_audit_session_id=1046138&p_keywords=>, 1 page.

Regnier, Fred E., "High Performance Liquid Chromatography of Proteins," Grant Abstract, Grant No. 5R01GM025431-05 [online]. National Institutes of General Medical Sciences, National Institutes of Health, project dates Jul. 1, 1978-Jun. 30, 1983 [retrieved on Sep. 10, 2001]. Retrieved from the Internet: URL: http.commons.cit.nih.gov/crisp3/crisp_lib.getdoc?textkey=4130838 &p_grant_num=5R01GM025431-05&p_query=ticket=78685 &p_audit_session_id=1046138&p_keywords=>, 1 page.

Regnier, Fred E., "High Performance Liquid Chromatography of Proteins," Grant Abstract, Grant No. 2R01GM025431-06 [online]. National Institutes of General Medical Sciences, National Institutes of Health, project dates Jul. 1, 1978-Jun. 30, 1988 [retrieved on Sep. 10, 2001]. Retrieved from the Internet: URL: http.commons.cit.nih.gov/crisp3/crisp_lib.getdoc?textkey=4130839 &p_grant_num=2R01GM025431-06&p_query=ticket=78685 &p_audit_session_id=1046138&p_keywords=>, 2 pages.

Regnier, Fred E., "High Performance Liquid Chromatography of Proteins," Grant Abstract, Grant No. 5R01GM025431-07 [online]. National Institutes of General Medical Sciences, National Institutes of Health, project dates Jul. 1, 1978-Jun. 30, 1988 [retrieved on Sep. 10, 2001]. Retrieved from the Internet: URL: http.commons.cit.nih.gov/crisp3/crisp_lib.getdoc?textkey=4130840 &p_grant_num=5R01GM025431-07&p_query=ticket=78685 &p_audit_session_id=1046138&p_keywords=>, 2 pages.

Regnier, Fred E., "High Performance Liquid Chromatography of Proteins," Grant Abstract, Grant No. 5R01GM025431-08 [online]. National Institutes of General Medical Sciences, National Institutes of Health, project dates Jul. 1, 1978-Jun. 30, 1988 [retrieved on Sep. 10, 2001]. Retrieved from the Internet: URL: http.commons.cit.nih.gov/crisp3/crisp_lib.getdoc?textkey=3272993 &p_grant_num=5R01GM025431-08&p_query=ticket=78685 &p_audit_session_id=1046138&p_keywords=>, 2 pages.

Regnier, Fred E., "High Performance Liquid Chromatography of Proteins," Grant Abstract, Grant No. 5R01GM025431-09 [online]. National Institutes of General Medical Sciences, National Institutes of Health, projcet dates Jul. 1, 1978-Jun. 30, 1988 [retrieved on Sep. 10, 2001]. Retrieved from the Internet: URL: http.commons.cit.nih.gov/crisp3/crisp_lib.getdoc?textkey=3272994 &p_grant_num=5R01GM025431-09& p_query=ticket=78685 &p_audit_session_id=1046138&p_keywords=>, 2 pages.

Regnier, Fred E., "High Performance Liquid Chromatography of Proteins," Grant Abstract, Grant No. 5R01GM025431-10 [online]. National Institutes of General Medical Sciences, National Institutes of Health, project dates Jul. 1, 1978-Jun. 30, 1988 [retrieved on Sep. 10, 2001]. Retrieved from the Internet: URL: http.commons.cit.nih.gov/crisp3/crisp_lib.getdoc?textkey=3272995 &p_grant_num=5R01GM025431-10&p_query=ticket=78685 &p_audit_session_id=1046138&p_keywords=>, 2 pages.

Regnier, Fred E., "High Performance Liquid Chromatography of Proteins," Grant Abstract, Grant No. 2R01GM025431-11 [online]. National Institutes of General Medical Sciences, National Institutes of Health, project dates Jul. 1, 1978-Jun. 30, 1993 [retrieved on Sep. 10, 2001]. Retrieved from the Internet: URL: http.commons.cit.nih.gov/crisp3/crisp_lib.getdoc?textkey=3272991 &p_grant_num=2R01GM025431-11&p_query=ticket=78685 &p_audit_session_id=1046138&p_keywords=>, 2 pages.

Regnier, Fred E., "High Performance Liquid Chromatography of Proteins," Grant Abstract, Grant No. 5R01GM025431-12 [online]. National Institutes of General Medical Sciences, National Institutes of Health, project dates Jul. 1, 1978-Jun. 30, 1993 [retrieved on Sep. 10, 2001]. Retrieved from the Internet: URL: http.commons.cit.nih.gov/crisp3/crisp_lib.getdoc?textkey=3272996 &p_grant_num=5R01GM025431-12&p_query=ticket=78685 &p_audit_session_id=1046138&p_keywords=>, 2 pages.

Regnier, Fred E., "High Performance Liquid Chromatography of Proteins," Grant Abstract, Grant No. 5R01GM025431-13 [online]. National Institutes of General Medical Sciences, National Institutes of Health, project dates Jul. 1, 1978-Jun. 30, 1993 [retrieved on Sep. 10, 2001]. Retrieved from the Internet: URL: http.commons.cit.nih.gov/crisp3/crisp_lib.getdoc?textkey=3272997 &p_grant_num=5R01GM025431-13&p_query=ticket=78685 &p_audit_session_id=1046138&p_keywords=>, 2 pages.

Regnier, Fred E., "High Performance Liquid Chromatography of Proteins," Grant Abstract, Grant No. 5R01GM025431-14 [online]. National Institutes of General Medical Sciences, National Institutes of Health, project dates Jul. 1, 1978-Jun. 30, 1993 [retrieved on Sep. 10, 2001]. Retrieved from the Internet: URL: http.commons.cit.nih.gov/crisp3/crisp_lib.getdoc?textkey=3272998 &p_grant_num=5R01GM025431-14&p_query=ticket=78685 &p_audit_session_id=1046138&p_keywords=>, 2 pages.

Regnier, Fred E., "High Performance Liquid Chromatography of Proteins," Grant Abstract, Grant No. 5R01GM025431-15 [online]. National Institutes of General Medical Sciences, National Institutes of Health, project dates Jul. 1, 1978-Mar. 31, 1994 [retrieved on Sep. 10, 2001]. Retrieved from the Internet: URL: http.commons.cit.nih.gov/crisp3/crisp_lib.getdoc?textkey=3272999&p_grant_num=5R01GM025431-15&p_query=ticket=78685&p_audit_session_id=1046138&p_keywords=>, 2 pages.

Regnier, Fred E., "Molecularly Imaged Media for HPLC of Proteins," Grant Abstract, Grant No. 2R01GM025431-16A1 [online]. National Institutes of General Medical Sciences, National Institutes of Health, project dates Jul. 1, 1978-Mar. 31, 1998 [retrieved on Sep. 10, 2001]. Retrieved from the Internet: URL: http.commons.cit.nih.gov/crisp3/crisp_lib.getdoc?textkey=2174438&p_grant_num=2R01GM025431-16A1&p_query=ticket=78685&p_audit_session_id=1046138&p_keywords=>, 1 page.

Regnier, Fred E., "Molecularly Imaged Media for HPLC of Proteins," Grant Abstract, Grant No. 5R01GM025431-17 [online]. National Institutes of General Medical Sciences, National Institutes of Health, project dates Jul. 1, 1978-Mar. 31, 1998 [retrieved on Sep. 10, 2001]. Retrieved from the Internet: URL: http.commons.cit.nih.gov/crisp3/crisp_lib.getdoc?textkey=2174439&p_grant_num=5R01GM025431-17&p_query=ticket=78685&p_audit_session_id=1046138&p_keywords=>, 1 page.

Regnier, Fred E., "Molecularly Imaged Media for HPLC of Proteins," Grant Abstract, Grant No. 5R01GM025431-18 [online]. National Institutes of General Medical Sciences, National Institutes of Health, project dates Jul. 1, 1978-Mar. 31, 1998 [retrieved on Sep. 10, 2001]. Retrieved from the Internet: URL: http.commons.cit.nih.gov/crisp3/crisp_lib.getdoc?textkey=2174440&p_grant_num=5R01GM025431-18&p_query=ticket=78685&p_audit_session_id=1046138&p_keywords=>, 1 page.

Regnier, Fred E., "Molecularly Imaged Media for HPLC of Proteins," Grant Abstract, Grant No. 5R01GM025431-19 [online]. National Institutes of General Medical Sciences, National Institutes of Health, project dates Jul. 1, 1978-Mar. 31, 1999 [retrieved on Sep. 10, 2001]. Retrieved from the Internet: URL: http.commons.cit.nih.gov/crisp3/crisp_lib.getdoc?textkey=2391855&p_grant_num=5R01GM025431-19&p_query=ticket=78685&p_audit_session_id=1046138&p_keywords=>, 1 page.

Regnier et al., "The next frontier in proteomics: recognizing and identifying proteins in regulatory flux," Poster Abstract, HPLC '99—23rd International Symposium on High Performance Liquid Phase Separation and Related Techniques, May 30-Jun. 4, Granada, Spain (May 31, 1999).

Regnier et al., "Multidimensional Separation Systems for the Analysis of Very Complex Peptide Mixtures," retrieved from http://www.richrom.com/assets/CD23PDF/pl25.pdf; Jun. 5, 2000; 13 pages.

Regnier et al., "Comparative proteomics based on stable isotope labeling and affinity selection," *J. Mass Spectrometry* 2002;37(2):133-145.

Reiber et al., "Identifying Proteins Using Matrix-Assisted Laser Desorption/Ionization In-Source Fragmentation Data Combined with Database Searching," *Analytical Chemistry*, 70(3):673-683 (1998).

Riggs et al., "Automated signature peptide approach for proteomics," *Journal of Chromatography A*, 924(1-2):359-368 (Jul. 27, 2001).

Riggs II, Larry D. "Phosphoprotein Proteomics" Ph.D. Thesis, Purdue University, (cover date May 2003). . . 157 Pages.

Rocklin et al., "A microfabricated fluidic device for performing two-dimensional liquid phase separations," *Anal. Chem.* 2000;72:5244-5249.

Roquemore et al., "Detection of O-linked N-Acetylglucosamine (O-GlcNAc) on Cytoplasmic and Nuclear Proteins," *Methods in Enzymology*, 230:443-460 (1994).

Roth et al., "Charge Derivatization of peptides for analysis by mass spectrometry," *Mass Spectrometry Reviews* 1998;17:255-274.

Schena et al., "Quantitative Monitoring of Gene Expression Patterns with a Complementary DNA Microarray," *Science*, 270, 467-470 (1995).

Schena et al., "Parallel human genome analysis: Microarray-based expression monitoring of 1000 genes," *Proceedings of the National Academy of Sciences USA*, 93(20):10614-10619 (1996).

Schnölzer et al., "Protease-catalyzed incorporation of $^{18}O$ into peptide fragments and its application for protein sequencing by electrospray and matrix-assisted laser desorption/ionization mass spectrometry," *Electrophoresis* 1996;17:945-953.

Scoffone et al., "Sulfenyl Halides as Modifying Reagents for Polypeptides and Proteins. I. Modification of Tryptophan Residues," *Biochemistry*, 7(3):971-979 (1968).

Smolka "Quantitative Protein Profiling Using Two-dimensional Gel Electrophoresis, Isotope-coded Affinity Tag Labeling, and Mass Spectrometry" *Molecular & Cellular Proteomics 1.1* 2002;19-29.

Sioma, Cathy S. "Multiplexed Global Inernal Standard Technique (mGIST) Using a Quanternary Amine Coding Agent," Ph.D. Thesis, Purdue University, (cover date May 2003).

VanBogelen et al., "Gene-Protein Database of *Escherichia coli* K-12, Edition 6," in *Escherichia coli and Salmonella, Cellular and Molecular Biology*, 2nd Ed., vol. 2, Neidhardt et al., eds., ASM Press, Washington, D.C., Title page, publication page and pp. 2067-2117 (1996).

Van der Werf et al., "Nutrigenomics: application of genomics technologies in mnutritional sciences and food technology." *J. Food Sci.* 2001;66:772-780.

Walsh et al., "The Australian proteome analysis facility (APAF): Assembling large-scale proteomics through integration and automation," *Electrophoresis* 1998;19:1883-1890.

Wang, H. et al., "Solute Retention Mechanism in Semipermeable Surface Chromatography," *Anal. Chem.* 1992;64:2821-2825.

Wang, S. et al., "Proteomics based on selecting and quantifying cysteine containing peptides by covalent chromatography," *Journal of Chromatography A*, 924(1-2):345-357 (Jul. 27, 2001).

Wang, Shihong "Novel Approaches in Proteomics to the Separation and Quantitation of Cellular Protein Expression," Ph.D. Thesis, Purdue University (cover date Aug. 2001).

Wang, S. et al., "Quantitative proteomics strategy involving the selection of peptides containing both cysteine and histidine from tryptic digests of cell lysates," *J. Chromatography A* 2002;949(1-2):153-162.

Washburn et al., "Large-scale analysis of the yeasts proteome by multidimensional protein identification technology," *Nature Biotechnology* 2001;19:242-247.

Watson, J.D. "The human genome project; past, present, and future." *Science* 1990;248:44-49.

Wilchek et al., "The isolation of tryptophan-containing peptides by affinity chromatography," *Biochimicia et Biophysica Acta*, 278(1):1-7 (1972).

Wilchek, "Isolation of Specific and Modified Peptides Derived from Proteins," *Methods in Enzymology*, 34:182-195 (1974).

Wu et al., "Simple method to identify cysteine-containing peptides by isotopic labeling and ion trap mass spectrometry," 219th ACS National Meeting. Abstract No. 2000:327134, (American Chemical Society) San Francisco, California, Mar. 26-30, 2000, 1 page.

Yao et al., "Proteolytic $^{18}O$ Labeling for Comparative Proteomics: Model Studies with Two Serotypes of Adenovirus," *Analytical Chemistry* 2001;73(13):2836-2842.

Yates, III, et al., "Direct Analysis of Protein Mixtures by Tandem Mass Spectrometry," *Journal of Protein Chemistry*, 16(5):495-497 (1997).

Yates, III, "Mass Spectrometry and the Age of the Proteome," *Journal of Mass Spectrometry*, 33(1):1-19 (1998).

Zhang, H. et al., "Capillary Electrophoresis Combined with Matrix-Assisted Laser Desorption/Ionization Mass Spectrometry; Continuous Sample Deposition on a Matrix-precoated Membrane Target," *Journal of Mass Spectrometry*, 31(9):1039-1046 (1996).

Zhang, R. et al., "Fractionation of isotopically labeled peptides in quantitative proteomics," *Analytical Chemistry* 2001;73(21):5142-5149.

Zhang, R. et al., "Minimizing Resolution of Isotopically Coded Peptides in Comparative Proteomics," *J. Proteome Research* 2002;1:139-147.

Zhang, R. et al., "Controlling Deuterium Isotope Effects in Comparative Proteomics," *Anal. Chem.* 2002;74(15):3662-3669.

Zhang, X. et al., "Analysis of channel-geometry effects on separation efficiency in rectangular-capillary electrochromatography columns," *Journal of Chromatography A*, 869(1-2):319-328 (2000).

Andersson et al "The use of immobilized $Fe^{+3}$ and other hard metal ions in chromatography of peptides and proteins." 1996 *Int. J. Bio-Chromatog.* 2:25-36.

Ausubel et al., eds., *Current Protocols in Molecular Biology*, vols. 1-4, John Wiley & Sons, Inc., New York, NY, 1994; title page, publisher's page and table of contents only; 12 pages.

Chakraborty "Global internal standard technology for comparative proteomics" 2002 *J. of Chromatography A* 949(1-2):173-84.

Chakraborty et al "Identification of up-regulated protein in *E. coli* based on signature peptides approach" 22th American Chemical Society National Meeting, Division of Analytical Chemistry, Symposium for Proteomics and Genomics in the 21st Century: Lecture 158. Washington, D.C.; Aug. 23, 2000. Available online [retrieved on Mar. 14, 2007]. Retrieved from the Internet: <http://chemistry.org/portal/PersonalScheduler/SearchResults.jsp?refineMode=Y&advSearch=0>; 1 pg.

"Cleavable ICAT Reagent" datasheet. Applied Biosystems; Foster City, CA; copyright 2003; 6 pgs.

Crestfield et al "The preparation and enzymatic hydrolysis of reduced and S-carboxylated proteins" 1963 *J. Biol. Chem.* 238(2):622-627.

Dormady, Shelly J., "Novel Applications of Bioanalytical Techniques for Proteomic Research," Ph.D. Thesis, Purdue University, (cover date May 2000).

Filer "Isotopic Fractionation of Organic Compounds in Chromatography" 1999 *J. Labelled Compd. Radiopharm.* 42:169-197.

Friso et al "Differential protein expression in rat trigeminal ganglia during inflammation." 2001 *Proteomics* 1:397-408.

Fu and vanHalbeek "N-glycolsylation site mapping of human serotransferrin by seral lectin affinity chromatography, fast atom bombardment-mass spectrometry, and 1H nuclear magnetic resonance spectroscopy" 1992 *Anal. Biochem.* 206(1):53-63.

Geng, Ming Hui "Proteomics of Glycoproteins," Ph.D. Thesis, Purdue University (cover date Aug. 2000).

Geng et al "Signature-peptide approach to detecting proteins in complex mixtures," 2000 *J. of Chromatography A* 870:295-313.

Griffiths, "Quantitative Proteomics Come of Age: Methods for quantitating proteins by MS increase in concentration," Sep. 1, 2007 *Analytical Chemistry* Product Review: 6451-6454.

Hansen et al "Immobilized metal ion affinity chromatography of synthetic peptides" 1992 *J. of Chromatography* 627:125-136.

Hemdan et al "Surface topography of histidine residues: A facile probe by immobilized metal ion affinity chromatography" 1989 *J. Proc. Antl. Acad. Sci. U.S.A.* 86:1811-1817.

Huczko et al "Characteristics of endogenous peptides eluted from the call I MHC molecule HLA-B7 determined by mass spectrometry and computer modeling" 1993 *J. Immunol.* 151(5):2572-2587.

Ji, Junyan, "Isotope Coding for Qualitative and Quantitative Study of Peptides and Proteins—a Global Internal Standard Technology in Proteomics," Ph.D. Thesis, Purdue University (cover date Dec. 2001).

Karger "High throughput mass spectrometry." 221st American Chemical Society National Meeting, Division of Industrial and Engineering Chemistry, ACS Award in Separation Science and Technology Symposium Honoring Csaba Horvath: Lecture 386. San Diego, California; Apr. 5, 2001. Available online [retrieved Mar. 13, 2007]. Retrieved from the Internet: <http://chemistry.org/portal/PersonalScheduler/SearchResults.jsp?refineMode=Y&advSearch=0>; 1 pg.

King et al "Mechanistic Investigation of Ionization Suppression in Electrospray Ionization" 2000 *J. Am. Soc. Mass Spec.* 11:942-950.

Kopf et al "Comparison of Tandem Mass Spectrometric Techniques Using Ion-trap and Hybrid Mass Spectrometers for Studies of the Degradation of a Herbicide by Biofilm." 1997 *Rapid Commun. Mass Spectrom.* 11:24-30.

Liu, Peiran "Qualitative Analysis of Proteomes with Isotope Labeling," Ph.D. Thesis, Purdue University (cover date Dec. 2003).

Mirgorodskaya et al "Quantitation of peptides and proteins by matrix-assisted laser desorption/ionization mass spectrometry using (18)O-labeled internal standards" 2000 *Rapid Commun Mass Spectrom* 14(14):1226-1232.

Munchbach, et al., "Quantitation and Facilitated de Novo Sequencing of Proteins by Isotopic N-Terminal Labeling of Peptides with a Fragmentation-Directing Moiety," Sep. 1, 2000 (web release date: Aug. 3, 2000) *Anal. Chem.* 72:4047-4057.

Nuwaysir and Stults "Electrospray ionization mass spectrometry of phosphopeptides isolated by on-line immobilized metal-ion affinity chromatography" 1993 *J. Am Soc Mass Spectrom.* 4:662-669.

Oda et al "Accurate quantitation of protein expression and site-specific phosphorylation" 1999 *Proc. Natl. Acad. Sci. USA* 96:6591-6596.

Parker et al "Quantitation in proteomics: Automatic processing of ICAT data," 48th ASMS Conference on Mass Spectrometry and Allied Topics [online]. Abstract No. 107. Long Beach, CA; Jun. 11-15, 2000. Available online [retrieved Mar. 12, 2007]. Retrieved from the Internet: <http://www.asms.org/aspfolder/ASMSarchresults.asp>; 6 pgs.

Pasa-Tolic et al "High Throughout Proteome—Wide Precision Measurements of Protein Expression Using Mass Spectrometry." 1999 *J. Am. Chem. Soc.* 121:7949-7950.

Patterson et al "Chapter 5: Mass spectrometry-based methods for protein identification and phosphorylation site analysis." (Pennington and Dunn, eds.) *Proteomics: From Protein Sequence to Function*; New York, NY:2001; Title page, Publisher's page, Table of Contents, and pp. 87-130.

Poehlein, Sara Kim, "I. Applications of fourier transform ion cyclotron resonance mass spectrometry to the studies of the isomers of the organometallic distonic ion and the reactivity of cobalt iodide. II. Analysis of polymers by matrix-assisted laser desorption ionization-TOF," Ph.D. thesis, Purdue University, 152 pages (Cover date Aug. 1999).

Preisler et al., "Capillary electrophoresis—matrix assisted laser desorption/ionization time-of-flight mass spectrometry using a vacuum deposition interface," 2000 *Anal Chem*. 72(20):4785-4795.

Ren, Diya "Sample Simplification Through Affinity Selection in Proteomics," Ph.D. Thesis; Purdue University (cover date May 2004).

Regnier et al "Multidimensional Chromatography and the Signature Peptide Approach to Proteomics." 2001 *LCGC* 19(2):200-213.

Regnier et al., "Multidimensional Chromatography and the Signature Peptide Approach to Proteomics," *LCGC*, 19(2) Feb. 2001 [online], [retrieved on Sep. 7, 2001]. Retrieved from the Internet <URL: http://www.chromatographyonline.com/articles.0102_Regnier_200-213/0102_Regnier.asp>, 14 pages.

Riggs II, Larry D. "Phosphoprotein Proteomics" Ph.D. Thesis, Purdue University, (cover date May 2003).

Schmidt et al., "A Novel Strategy for Quantitative Proteomics Using Isotope-Coded Protein Labels," 2005 *Proteomics* 5:4-15.

Sioma, Cathy S. "Multiplexed Global Inernal Standard Technique (mGIST) Using a Quanternary Amine Coding Agent," Ph.D. Thesis, Purdue University, (cover date May 2003).

Stemmann et al., "Dual Inhibition of Sister Chromatid Separation at Metaphase," Dec. 14, 2001 *Cell* 107:715-726.

Stewart et al "Refining high throughput peptide analysis (proteomics) using $^{18}O$ labeling," 49th ASMS Conference on Mass Spectrometry and Allied Topics [online]. Abstract No. 162. Chicago, IL; May 27-31, 2001. Available online [retrieved Mar. 12, 2007]. Retrieved from the Internet: <http://www.asms.org/aspfolder/ASMSarchresults.asp>; 2 pgs.

Thomas, "Metabolomics breaks the silence." 2001 *Trends in Biotechnology* 19:126-127.

Veenstra et al. "Protein Analysis Using Selective Incorporation of Isotopically Labeled Amino Acids." 2000 *J. Am. Soc. Mass Spectrom.* 11:78-82.

Wang et al "Inverse $^{18}O$ Labeling Mass Spectrometry for the Rapid Identification of Marker/Target Proteins." 2001 *Anal Chem* 73:3742-3748.

Yao et al., "Proteolytic 18O Labeling for Comparative Proteomics: Model Studies with Two Serotypes of Adenovirus," Jul. 1, 2001 *Anal. Chem.* 73:2836-2842.

Zhang, Xiang, "Informatics of Signature Peptide Approach to Proteomics," Ph.D. Thesis, Purdue University, (cover date Dec. 2001).

Aebersold "Quantitative proteome analysis: New technology and applications." Meeting Abstract: The 14th International Symposium of Microscale Seperations and Analysis: HPCE 2001; Boston, MA; Jan. 13-18, 2001. *Final Program & Book ob Abstracts*. Lecture L1101; p.195.

Karger "High throughput mass spectrometry for proteomics" Meeting Abstract: the 14th International Symposium of Microscale Seperations and Analysis: HPCE 2001; ; Boston, MA; Jan. 13-18, 2001. *Final Program & Book of Abstracts*. Lecture L1106; p. 198.

Regnier "Global internal standard Technology in proteomics" Meeting Abstract: The 14th International Symposium of Microscale Separations and Analysis: HPCE 2001; Boston, MA; Jan. 13-18, 2001. *Final Program & Book of Abstracts*. Lecture L1102; p. 196.

U.S. Appl. No. 60/958,106, filed Jul. 02, 2007, Regnier et al.

Aebersold et al., "The isotope-coded affinity tag reagent method for quantitative proteomics," *Am. Gen. Prot. Tech. (ISC, inc)* 2001 Jul. Aug., AGPT 2001: 22-27.

"Applied Biosystems iTRAQ™ Reagents: amine modifying labeling reagents for multiplexed relative and absolute protein quantification," Chemistry Reference Guide. Applied Biosystems: Foster CIty, CA; © 2004. Available online [retrieved Jan. 22, 2008]. Retrieved from the Internet: <http://www3.appliedbiosystems.com/cms/groups/psm_marketing/documents/generaldocuments/cms_041463.pdf>; 96 pages.

Bottari et al., "Design and Syntheis of visible isotope-coded affinity tags for the absolute quantification to specific proteins in complex mixtures," Feb. 21, 2004 *Bioconjugate Chem.* 15(2): 380-388. Epub on Feb. 21, 2004.

"Cleavable ICAT® Reagent" datasheet. Applied Biosystems; Foster City, CA; © 2002; printed in the USA Aug. 2002. 6 pgs.

"Cleavable ICAT® Reagent" product description. Applied Biosystems; Foster City, CA; Available online [retrieved Aug. 17, 2007]. Retrieved from the Internet: <https://products.appliedbiosystems.com/ab/en/US/adirect/ab;jsessionid=QmcNHpQFTL9BzLITdQT3YbGegFHv2Xj3clnBYnQQCHzwvVG9sSwr!-73289809?cmd=catNavigate2&catID=600902&tab=DetailInfo>; 2 pgs.

"Cleavable ICAT® Reagent Kit for Protein Labeling," protocol. Applied Biosystems; Foster City, CA; © 2003; printed in the USA Sep. 2003. 20 pages.

Ewing et al., "$^{18}$O proteome profiler kit: a useful tool for relative quantitation of global differential protein expression," Application Notes [online]. Sigma Aldrich, St. Louis, MO: 2005. [retrieved on Jan. 22, 2008]. Retrieved from the Internet: <http://www.sigmaaldrich.com/sigma/general%20information/vol6%20iss1%20o18proteome.pdf>; 2 pgs.

Han et al., Quantitative profiling of differentiation-induced microsomal proteins using isotope-coded affinity tages and mass spectrometry, *Nat. Biotechnol.* Oct. 2001., 19(10): 946-951.

"ICAT Reagent Technology: Breakthrough technology for protein expression analysis," product brochure. Applied Biosystems; Foster City, CA; ©2002; printed in the USA Feb. 2002. 10 pages.

"The ICPL-Kit for quantitative proteomics," product brochure: Bruker Daltronics; Billerica, Maryland. 2005, Available online [retrieved Jan. 22, 2008]. Retrieved from the Internet: <http://www.bdal.de/data/literature/care-icpl.pdf>; 4 pages.

"iTRAQ™ Reagents" Product Bulletin [online]. Applied Biosystems, Foster City, CA: © 2004. [retrieved on Jan. 22, 2008]. Retrieved from the Internet: <http://www.cbs.umm.edu/msp/services/iraq.pdf>; 8 pages.

Kindy et al., "Quantifying peptides in isotopically labeled protease digests by ion mobility/time-of-flight mass spectrometry," Mar. 1, 2002 *Anal. Chem.* 74(5):950-958. Epub 29 Jan. 2002.

Li et al., "CILAT - a new reagent for quantitative proteomics," Mar. 2, 2007 *Chem. Commun.* 2181-2183. Epub Mar. 2, 2007.

Lu et al., "Abosulte quantification of specific proteins in complex mixtures using visible isotope-coded affinity tags," Jul. 15, 2004 *Anal. Chem.* 76(14): 4104-4111. Epub Jun. 11, 2004.

"New amine specific iTRAQ™ reagents expand multiplexing and quantitation capabilities for proteomic researchers," Product News. Applied Biosystems; Foster City, CA. © 2004, printed in the UK. Available online [retrieved Jan. 22, 2008]. Retrieved from the Internet: <http://www.appliedbiosystems.com/europe/biosystems/pdf/iss10/biosol_iss10_itraq.pdf>; 3 pages.

"$^{18}$O Proteome Profiler Kit," Technical Bulletin [online]. Sigma: St. Louis, Missouri. Published post-2003. [retrieved on Jan. 22, 2008]. Retrieved from the Internet: <http://www.sigmaaldrich.com/sigma/bulletin/P3623bul.pdf>; 6 pages.

Schneider and Hall, "Stable isotope methods for high-precision proteomics," Mar. 2005 *Drug Discovery Today* 10(5):353-363.

Silverman et al., "Rapid mapping of protein stucture, interactions, and ligand binding by misincorporation proton-alkyl exchange," Aug. 23, 2002 *J. Biol. Chem.* 277(34):30968-30975. Epub May 25, 2002.

Shiio et al., "Quantitative proteomics analysis of Myc oncoprotein function," 2002 *EMBO J.* 21(19): 5088-5096.

Smolka et al., "Optimization of the isotope-coded affinity tag-labeling procedure for quantitative proteome analysis," Oct. 1, 2001 *Anal. Biochem.* 297(1): 25-31. Epub Sep. 12, 2001.

Wehr, "Quantitative proteomics: Available tools and results of collaborative study," Oct. 1, 2007 *LCGC North America e-Separation Solutions Newsletter*. Available online [retrieved Jan. 22, 2008]. Retrieved from the Internet: <http://license.icopyright.net/user/viewFreeUse.act?fuid=ODQ1NTA2>; 7 pages.

Zhou et al., "Quantitative proteome analysis by solid-phase isotope tagging and spectromety," May 2002 *Nat. Biotech.* 19: 512-515.

Aebersold and Cravatt, "Proteomics- advances, applications and the challenges that remain," Dec. 1, 2002 *Trends in Biotech.* 20(12 Suppl):s1-s2.

Cagney and Emili, "*De novo* peptide sequencing and quantitative profiling of complex protein mixtures using mass-coded abundance tagging," Feb. 2002*Nature Biotech.* 20(2); 163-170.

Flory et al., "Advances in quantitative proteomics using stable isotope tags," Dec. 1, 2002 *Trends in Biotech.* 20(12 Suppl): s23-s29.

Goodlett and Yi, "Proteomics without polyacrylamide: qualitative and quantitative uses of the tandem mass spectrometry in proteome analysis," Sep. 2002 *Funct. Imtegr. Genomics* 2(4-5): 138-153. Epub Jan. 22, 2002.

Goshe et al., "Phosphoprotein isotope-coded affinity tag approach for isolating and quantitating phosphopeptides in proteome-wide analyses," Jun. 1, 2001 *Anal. Chem.* 73(11): 2578-2586. Epub Apr. 28, 2001.

Griffin et al., "Quantitative proteomic analysis using a MALDI quadrupole time-of-flight mass spectrometer," Mar. 1, 2001 *Anal. Chem.* 73(5): 978-986.Epub Feb. 3, 2001.

Griffin et al., "Abundance ratio-dependent proteomic analysis by mass spectrometry," Feb. 15, 2003 *Anal. Chem.* 75(4): 8678-874. Epub Jan. 16, 2003.

Lee et al., "Development of the multiplexed microcapillary liquid chromatography system for high throughput proteome analysis," Sep. 1, 2002 *Anal. Chem.* 74(17): 4353-4360. Epub Aug. 8, 2002.

Liu and Regnier, "An isotope coding strategy for the proteomics involving both amine and carboxyl group labeling," Sep-Oct. 2002 *J. Proteome Res.* 1(5): 443-450. Epub Jul. 16, 2002.

Oda et al., "Quantitative chemical proteomics for identifying candidate drug targets,"May 1, 2003 *Anal. Chem.* 75(9): 2159-2165. Epub Apr. 3, 2003.

Peng and Gygi, "Proteomics: the move to the mixtures,"2001 *J. Mass. Spectrom.* 36: 1083-1091. Epub Oct. 3, 2001.

Qui, Ruiqing "Multidimensional Chromatography and Mass Spectrometry for Differential Glycoproteomics," Ph.D. Thesis; Purdue University (cover date May 2005).

Reynolds et al., "Proteolytic 18O labeling for comparative proteomics: evaluation of endoprotease Glu-C as the catalytic agent," Jan/Feb 2002 *J. Proteome Res.* 1(1): 27-33. Epub Jan. 7, 2002.

Sechi and Oda, "Quantitative proteomics using mass spectrometry," Feb. 2003 *Curr. Opinion in Chem. Biol.* 7(1): 70-77.

Smolka et al., "Quantitative protein profiling using two-dimensional gel electrophoresis, isotope-coded affinity tag labeling, and mass spectrometry," 2002 *Mol. Cell. Proteomics* 1(1): 19-29. Epub Oct. 11, 2001.

Steen and Pandey, "Proteomics goes quantitative: measuring protein abundance," Sep. 2002 *Trends Biotechnol.* 20(9): 361-364. Epub Jul. 9, 2002.

Tao and Aebersold, "Advances in quantitative proteomics via stable isotope tagging and mass spectrometry," Feb. 2003*Curr. Opinion in Biotech.* 14(1): 110-118.

Turecek, "Mass spectrommetry in coupling with affinity capture-release and isotope-coded affinity tags for quantitative protein analysis," Aug. 2002 *J. Mass Spectrom.* 37(1):1-14. Epub Dec. 21, 2001.

Zhang, Roujian "Intelligent Use of Signature Peptide Approach to Proteomics," Ph.D. Thesis; Purdue University (cover date Aug. 2002). Available in Purdue University Library on Aug. 4, 2003. Available online on Dec. 10, 2003.

\* cited by examiner

A

B

A

B

C

A

B

SEQUENCE LISTING

```
<160> NUMBER OF SEQ ID NOS: 14

<210> SEQ ID NO 1
<211> LENGTH: 8
<212> TYPE: PRT
<213> ORGANISM: artificial
<220> FEATURE:
<223> OTHER INFORMATION: test peptide

<400> SEQUENCE: 1

Gln Asn Cys Asp Gln Phe Glu Lys
```

```
1               5

<210> SEQ ID NO 2
<211> LENGTH: 5
<212> TYPE: PRT
<213> ORGANISM: artificial
<220> FEATURE:
<223> OTHER INFORMATION: test peptide

<400> SEQUENCE: 2

Ile Phe Val Gln Lys
1               5

<210> SEQ ID NO 3
<211> LENGTH: 6
<212> TYPE: PRT
<213> ORGANISM: artificial
<220> FEATURE:
<223> OTHER INFORMATION: test peptide

<400> SEQUENCE: 3

Tyr Ile Pro Gly Thr Lys
1               5

<210> SEQ ID NO 4
<211> LENGTH: 11
<212> TYPE: PRT
<213> ORGANISM: artificial
<220> FEATURE:
<223> OTHER INFORMATION: test peptide

<400> SEQUENCE: 4

Thr Gly Pro Asn Leu His Gly Leu Phe Gly Arg
1               5                   10

<210> SEQ ID NO 5
<211> LENGTH: 7
<212> TYPE: PRT
<213> ORGANISM: artificial
<220> FEATURE:
<223> OTHER INFORMATION: test peptide

<400> SEQUENCE: 5

Met Ile Phe Ala Gly Ile Lys
1               5

<210> SEQ ID NO 6
<211> LENGTH: 6
<212> TYPE: PRT
<213> ORGANISM: artificial
<220> FEATURE:
<223> OTHER INFORMATION: test peptide

<400> SEQUENCE: 6

Cys Ala Ser Ile Gln Lys
1               5

<210> SEQ ID NO 7
<211> LENGTH: 7
<212> TYPE: PRT
<213> ORGANISM: artificial
<220> FEATURE:
<223> OTHER INFORMATION: test peptide

<400> SEQUENCE: 7

Gly Ala Cys Leu Leu Pro Lys
1               5
```

```
<210> SEQ ID NO 8
<211> LENGTH: 7
<212> TYPE: PRT
<213> ORGANISM: artificial
<220> FEATURE:
<223> OTHER INFORMATION: test peptide

<400> SEQUENCE: 8

Leu Cys Val Leu His Glu Lys
1               5

<210> SEQ ID NO 9
<211> LENGTH: 9
<212> TYPE: PRT
<213> ORGANISM: artificial
<220> FEATURE:
<223> OTHER INFORMATION: test peptide

<400> SEQUENCE: 9

Ser His Cys Ile Ala Glu Val Glu Lys
1               5

<210> SEQ ID NO 10
<211> LENGTH: 12
<212> TYPE: PRT
<213> ORGANISM: artificial
<220> FEATURE:
<223> OTHER INFORMATION: test peptide

<400> SEQUENCE: 10

Ser Leu His Thr Leu Phe Gly Asp Glu Leu Cys Lys
1               5                   10

<210> SEQ ID NO 11
<211> LENGTH: 12
<212> TYPE: PRT
<213> ORGANISM: artificial
<220> FEATURE:
<223> OTHER INFORMATION: test peptide

<400> SEQUENCE: 11

Tyr Ile Cys Asp Asn Gln Asp Thr Ile Ser Ser Lys
1               5                   10

<210> SEQ ID NO 12
<211> LENGTH: 16
<212> TYPE: PRT
<213> ORGANISM: artificial
<220> FEATURE:
<223> OTHER INFORMATION: test peptide

<400> SEQUENCE: 12

Leu Phe Thr Phe His Ala Asp Ile Cys Thr Leu Pro Asp Thr Glu Lys
1               5                   10                  15

<210> SEQ ID NO 13
<211> LENGTH: 21
<212> TYPE: PRT
<213> ORGANISM: artificial
<220> FEATURE:
<223> OTHER INFORMATION: test peptide

<400> SEQUENCE: 13

Gly Leu Val Leu Ile Ala Phe Ser Gln Tyr Leu Gln Gln Cys Pro Phe
1               5                   10                  15
```

```
Asp Glu His Val Lys
            20

<210> SEQ ID NO 14
<211> LENGTH: 14
<212> TYPE: PRT
<213> ORGANISM: artificial
<220> FEATURE:
<223> OTHER INFORMATION: test peptide

<400> SEQUENCE: 14

Met Pro Cys Thr Glu Asp Tyr Leu Ser Leu Ile Leu Asn Arg
1               5                   10
```

MATERIALS AND METHODS FOR CONTROLLING ISOTOPE EFFECTS DURING FRACTIONATION OF ANALYTES

This application claims the benefit of U.S. Provisional Application Ser. No. 60/325,335, filed Sep. 27, 2001, which is incorporated herein by reference in its entirety.

STATEMENT OF GOVERNMENT RIGHTS

This invention was made with government support under a grant from the National Institutes of Health, Grant No. GM 59996. The U.S. Government has certain rights in this invention.

BACKGROUND OF THE INVENTION

The science of proteomics seeks to efficiently quantify, identify and characterize the large number of proteins/peptides that characterize a biological system. Two approaches to proteomics are being pursued today. One focuses on cataloging all the proteins in a biological system, the cellular components with which each of these protein interact, the pathways of which they are a part, and the location in which they reside. The other strategy, known as "comparative proteomics" is based on a comparison of proteins in a biological system in two different states. Disease and a wide range of other stimuli cause biological systems to pass into a new, chemically distinct state distinguished by changes in the occurrence and amount of specific proteins. Comparing samples taken from organisms in the normal and an altered state can be used to recognize proteins involved in the transition.

Although "proteomics" is a recently coined term, comparative proteomics has actually been practiced for at least three decades. For example, early studies used 2-D gel electrophoresis to examine thousands of proteins in blood. These reports, and many since, depended on resolution of complex protein mixtures with 2-D gels and differential staining to compare samples and recognize differences. This classical method is labor intensive, quantification is poor, and it is difficult to identify spots thought to be important.

With the advent of huge DNA and protein sequence databases there is an increasing dependence on mass spectrometry to identify proteins and peptides obtained from separation systems. The speed and resolution of mass spectrometers is shifting the focus in proteomics toward more rapid delivery of peptide mixtures to mass spectrometers and obtaining quantitative as well as qualitative data during mass analysis.

Stable isotope coding strategies are of great value for distinguishing changes in comparative proteomics. These coding techniques may be broadly characterized as internal standard methods in which components from control samples are derivatized with an isotopically distinct coding agent, mixed with experimental samples, then used as standards for determining the relative concentration of components in experimental samples derivatized with a different isoform of the coding agent (PCT WO 01/86306, published Nov. 15, 2001, Ji et al., *J. Chromatogr. B*, (2000) 745, 197-210). Most of the coding agents used today are labeled with deuterium, and relative concentration measurements are based on isotope abundance ratio determinations with either matrix assisted laser desorption ionization-mass spectrometry (MALDI-MS) or electrospray ionization-mass spectrometry (ESI-MS).

As with all internal standard methods, it is important that the behavior of analytes and standards be as nearly alike as possible before the final step of abundance ratio measurement. Ideally, segregation would occur only in the final step during quantification. The attractive feature of creating internal standards through isotopic labeling is that discrimination is minimized, particularly when the internal standard and analyte vary by a single heavy atom.

The problem with current stable isotope coding methods for proteomics is that as the number of deuterium atoms is increased to enlarge the mass difference between isotopically coded standards and analytes, there is a corresponding increase in chromatographic resolution of the isotopic isoforms, particularly in the case of reversed-phase chromatography (Zhang et al., Anal. Chem., 2001, 73, 5142-5149). As a result, the concentration ratio of isoforms varies continuously across the elution profile of the two components.

This "isotope effect" has a number of undesirable consequences. Because of the isotope effect caused by deuterium in chromatographic separation, the accuracy of abundance ratio measurement is greatly compromised, particularly in MALDI-MS. In online ESI-MS analysis, there is a serious trade-off between accurate quantification and MS/MS peptide sequencing because of the deuterium isotope effect.

For example, using existing methods (e.g., abundance ratio measurements) to determine a relative change in concentration of components from a single mass spectrum is not possible. Instead, relative concentration must be obtained by a comparison of area measurements between integrated extracted ion chromatograms in the case of ESI-MS or from eluate fractions with MALDI-MS. High quality MS/MS data of peptides are crucial to the reliability of protein identification and characterization. Unfortunately, this requires certain tuning and ion accumulation. In another word, it takes time. It is very much desired to selectively fragment the peptides of interest.

In the case of ESI-MS, the analyte peak must completely elute from the LC-MS system before it can be determined whether the peptide has changed in concentration and is therefore of interest (Griffin et al., Journal of the American Society for Mass Spectrometry, 2001, 12, 1238-1246). This effectively precludes the use of on-line, intelligent data acquisition and analysis (IDA), also referred to as real-time data dependent analysis (DDA). Either a second chromatographic run is required after the abundance ratio is determined in order to selectively perform MS/MS analysis on the peptides of interest, or the mass spectrometer has to acquire MS/MS data on every peptide to be sure data has been acquired on peptides that changed in concentration. In either case, instrument and computer time are wasted.

Feedback control software is available in some commercially available mass spectrometers. The most abundant peaks are typically selected for further analysis on-line in "real time". The most abundant peaks, however, do not necessarily coincide with analytes that are significantly up or down regulated, which in comparative proteomics are more often the analytes of interest. In other commercially available instruments, LC/MS is run twice, first to obtain abundance ratios and second to selectively fragment peptides based on the abundance ratios. This method may yield information on analytes that are up or down regulated, but has a major drawback in that abundance ratio based feedback control is not performed in "real time" since two chromatographic runs are used.

Reconstruction of extracted ion chromatograms is really only possible with ESI-MS. Reconstruction of peaks from MALDI-MS is very difficult in complex mixtures unless 10-60 fractions are collected across each peak. Anywhere from 2,000-10,000 fractions would have to be collected and analyzed by MALDI-MS to reconstruct extracted ion chromatograms for the thousands of peptides encountered in a single reversed phase chromatographic separation. This is so cumbersome that MALDI-MS by any approach but continuous deposition is essentially precluded when quantification accuracy is an issue.

Integration of peak areas is even more difficult and inaccurate when isotopically labeled peptides are fractionated in one or more of the early steps in a multi-dimensional separation experiment. For example, isotopically labeled peptides could be separated in ion exchange chromatography followed by reversed-phase chromatography, or reversed-phase chromatography followed by ion mobility separation.

Further complications can arise when ionization efficiency of the isoforms varies with time in ESI-MS or between fractions in MALDI-MS. Suppression of ionization between peptides has been noted in ESI-MS when total peptide concentration is high, as when one peptide is eluting in a large background of another. This means that ionization efficiency can vary across a chromatographic peak. In MALDI-MS, the chromatographic fractions used for spectral analysis may be enriched in one isotopic isoform over the other and may differ widely in matrix components. The peptide isoforms could be suppressed to very different degrees when they are not eluted simultaneously and thus ionized with a different matrix (i.e., with other co-eluting peptides). These effects compromise abundance ratio measurements by potentially producing both significant systematic errors and a higher level of random errors (Zhang et al., Anal. Chem. 2001, 73, 5142 -5149), even when relative peak areas are estimated with extracted ion chromatograms.

Finally there is the most serious problem of all. When the isotopic isoforms are completely resolved, as is frequently the case with labeled peptides that contain many deuterium atoms, whether or not the two peaks are related cannot be determine unless the peptides are sequenced or mass is measured with very high mass accuracy. This leads to the erroneous conclusion that the singlet cluster seen in one of the resolved peaks is representative for the peptide and that it has undergone a major change in concentration.

Clearly, minimizing chromatographic resolution of analyte isoforms would improve measurement accuracy and enable real-time measurements.

SUMMARY OF THE INVENTION

The invention advances the science of proteomics as well as analytical chemistry in general in that it provides a reliable, real-time method to detect the changes in analyte concentration and/or modification. Improved accuracy of isotope abundance ratio measurement is achieved, and false positives and false negatives caused by the systematic errors in the measurement are reduced or eliminated.

Isotope effect can cause significant errors in protein/peptide quantitation and identification. The invention solves this problem by minimizing the isotope effect. The isotope effect can be reduced by eliminating deuterium ($^2$H) from the isotope coding agent and using instead different heavy isotopes, preferably $^{13}$C, $^{18}$O and/or $^{15}$N, more preferably $^{13}$C, to provide the difference in mass. Preferably, proteins/peptides are labeled with an isotope coding agent containing two or more, preferably three or more, $^{13}$C atoms, $^{18}$O atoms, $^{15}$N atoms or any combination thereof. A difference of at least 2-3 amu (atomic mass units) among isoforms is needed, preferably a difference of 3 or more amu, otherwise the isotopically labeled analytes may heavily overlap in mass spectra and become difficult to deconvolute. The isotope coding agent of the invention preferably contains no deuterium atoms.

Importantly, the present invention makes real-time intelligent data acquisition possible. In addition, the identical or nearly identical chromatographic retention times can be used to confirm the recognition of isoform pairs. The invention is well-suited to comparative proteomics applications, general analytical chemistry, and the analysis of biomolecules such as peptides, small molecules, sugars and drugs.

In one aspect, the invention provides an isotope coding agent that includes at least three non-deuterium isotopes. The non-deuterium isotopes present in the isotope coding agent are preferably $^{13}$C, $^{18}$O, $^{15}$N or any combination thereof. The non-deuterium isotopes that are incorporated into an isotope coding agent of the invention can differ or be the same. A preferred isotope coding agent contains a reactive functional group that reacts with the analyte of interest, preferably with an amine, a carboxyl, a hydroxyl or a thiol present on the analyte of interest. Examples of a reactive functional group are iodoacetamide and iodoacetate, which react with free thiols. In a particularly preferred embodiment the isotope coding agent includes a reactive functional group and an isotopic linker that includes the least three heavy non-deuterium isotopes. Optionally, the isotope coding agent further includes an affinity "tag", i.e., a functional group such as biotin for affinity selection. An example of such an isotope coding agent is the $^{13}$C-ICAT reagent available from Applied Biosystems, Inc. Succinic anhydride, N-acetoxysuccinimide and propionate-N-hydroxysuccinimide that include heavy non-deuterium isotopes are also preferred isotope coding agents.

The invention also includes a method for making an isotope coding agent. Many deuterated isotope coding agents are in common use. In this aspect of the invention, any deuterated isotope coding agent can serve as the basis for the design of an isotope coding agent that includes non-deuterium heavy isotopes. The method involves synthesizing an isoform of the isotope coding agent that includes non-deuterium heavy isotopes instead of deuterium. At least three heavy isotopes are independently selected from the group consisting of $^{13}$C, $^{18}$O and $^{15}$N and incorporated into a compound to yield the analogous $^{13}$C-, $^{18}$O- and/or $^{15}$N-containing isotope coding agent. The isotope effect observed for the $^{13}$C-, $^{18}$O- and/or $^{15}$N-isotope coding agent is expected to be smaller than the isotope effect observed for the deuterated isoform. Also included in the invention is a method for isotopically coding an analyte that involves covalently linking the analyte to an isotope coding agent, wherein the isotope coding agent includes at least three heavy isotopes independently selected from the group consisting of $^{13}$C, $^{18}$O and $^{15}$N.

In another aspect, the invention includes a peptide that is covalently linked to one or more isotope coding agents, each having at least three non-deuterium (e.g., $^{13}$C, $^{18}$O or $^{15}$N or any combination thereof) isotopes. Preferred isotope coding agents for linkage to the peptide include an ICAT reagent, succinic anhydride, N-acetoxysuccinimide and propionate-N-hydroxysuccinimide.

In yet another aspect, the invention provides a device for detecting a difference in the concentration of an analyte present in first sample and second samples. The device includes a sample fractionator which has an outlet, and a mass spectrometer coupled to the outlet of the sample fractionator. The fractionator is preferably a chromatography column, more preferably a reversed phase column.

Software is also included, which advantageously allows determination of the abundance ratio for the analyte using the mass spectrum of a combined sample immediately following elution of isotopically labeled analytes from the sample fractionator. In one embodiment, the software determines a normalized abundance ratio characterizing analytes whose concentration is the same in the first and second samples and an abundance ratio of the first and second isotopically labeled analytes. A difference in the abundance ratio of the first and second isotopically labeled analytes and the normalized abundance ratio is indicative of a difference in concentration of the analyte in the first and second samples.

Importantly, the abundance ratios are determined in real time such that an eluted fraction containing analytes that have changed in concentration can be immediately subjected to further analysis using MS-MS. This analysis can be performed on-line, in real time. Advantageously, the decision of whether to perform MS-MS on a peak can be made by the software without input from a human operator. Preferred devices are those incorporating software designed for proteomics applications and blood sample analysis.

A method for using the device is also provided. Samples to be analyzed each contain a plurality of analytes. Analytes in each sample are labeled with, or contain, an isoform of an isotope coding agent. Preferably the isotope coding agent contains no deuterium. The isoforms of the isotope coding agent differ as between the samples; at least one isoform includes at least one non-deuterium heavy atom (e.g., $^{13}C$, $^{18}O$ and/or $^{15}N$) and has a mass of at least 3 amu greater than the mass of an isoform comprising no heavy isotopes.

The samples are combined, and the combined sample is fractionated using the fractionator, yielding a plurality of elution peaks. Fractionation includes, for example, single or multi-dimensional reversed phase chromatography, ion exchange chromatography, hydrophobic interaction chromatography, size exclusion chromatography, capillary gel electrophoresis, capillary zone electrophoresis, and capillary electrochromatography, capillary isoelectric focusing, immobilized metal affinity chromatography, affinity electrophoresis or any combination thereof. Preferably, the different isoforms of an analyte do not resolve during fractionation.

MS is performed on each elution peak, and the relative abundance ratio is calculated in real time to detect analytes exhibiting a change in concentration. Optionally, MS-MS is performed on the elution peak comprising the isoforms exhibiting a change in concentration to further analyze said isoforms. Preferably, mass spectrometric analysis is performed using matrix assisted laser desorption ionization (MALDI), electrospray ionization (ESI), fast atom bombardment (FAB), electron impact ionization, atmospheric pressure chemical ionization (APCI), time-of-flight (TOF), quadrapole, ion trap, magnetic sector, ion cyclotron resonance mass, or combinations thereof. Also optionally, the analyte exhibiting the change in concentration is identified.

The first sample can be obtained from an environment before application of a stimulus, and the second sample can be obtained from an environment after application of the stimulus. Likewise, the first sample can be obtained from an environment in the presence of, or after application of, a stimulus and the second sample can be obtained from an environment in the absence of the stimulus. The samples can be obtained from different organisms, cells, organs, tissues or bodily fluids, the method further comprising determining differences in concentration of at least one protein in the organisms, cells, organs, tissues or bodily fluids from which the samples were obtained, and can contain about 100 or more proteins. In biological samples, the analytes can be peptides produced by proteolysis of samples containing proteins, and MS-MS analysis of the elution peak that contains isoforms of peptides exhibiting a change in concentration can be used to identify the proteins from which the peptides were derived.

The method of the invention allows detection of a difference in the concentration of an analyte, preferably a protein, present in first sample and second samples, wherein each sample includes a plurality of analytes. In this embodiment, the method involves first covalently attaching a first isoform of a labeling agent to the analyte in the first sample to yield at least one first isotopically labeled analyte, and covalently attaching a second isoform of the labeling agent to the analyte in the second sample to yield at least one second isotopically labeled analyte, wherein the first isoform includes at least one non-deuterium heavy isotope, and wherein the first and second isoforms differ in mass by at least 3 amu. At least portions of the first and second samples are then mixed to yield a combined sample.

The combined sample is subjected to mass spectrometric analysis to determine a normalized abundance ratio characterizing analytes whose concentration is the same in the first and second samples and an abundance ratio of the first and second isotopically labeled analytes, wherein a difference in the abundance ratio of the first and second isotopically labeled analytes and the normalized abundance ratio is indicative of a difference in concentration of the analyte in the first and second samples.

Optionally, the method includes fractionating the combined sample using a sample fractionator to yield at least one fraction containing the first and second isotopically labeled analytes prior to determining the abundance ratios. The isotope effect observed during fractionation of a mixture of the first and second isotopically labeled analytes is expected to be smaller than the isotope effect observed during fractionation of a mixture that includes the second isotopically labeled analyte and an analyte labeled with a deuterated isoform of the labeling agent.

Optionally, mass spectrometric analysis is performed on the fraction immediately following elution of the fraction from the sample fractionator. Abundance ratios are determined in real time such that an eluted fraction comprising analytes that have changed in concentration can be immediately subjected to further analysis using MS-MS.

When the analyte of interest is a protein, proteins in the samples can be cleaved after labeling to yield first and second isotopically labeled peptides in the first and second samples, respectively. At least portions of the first and second samples are mixed to yield the combined sample, which is subjected to further fractionation and mass spectrometric analysis in accordance with the invention, as desired.

Alternatively, proteins in the samples can be cleaved prior to labeling to yield constituent peptides. A first isoform of a labeling agent is covalently attached to a peptide in the first sample to yield at least one first isotopically labeled peptide and a second isoform of the labeling agent is covalently attached to a peptide in the second sample to yield at least one second isotopically labeled peptide. Preferably, the first and second isoforms of the labeling agent are attached to at least one amino group on peptides in the first and second samples. The first isoform comprises at least one non-deuterium heavy isotope, and the first and second isoforms differ in mass by at least 3 amu. At least portions of the first and second samples are then mixed to yield the combined sample, which is subjected to further fractionation and mass spectrometric analysis in accordance with the invention, as desired.

A normalized abundance ratio characterizing peptides derived from proteins whose concentration is the same in the first and second samples is determined, as well as an abundance ratio of the first and second isotopically labeled peptides. Mass spectrometric analysis is performed on the fraction immediately following elution of the fraction from the sample fractionator, and abundance ratios are determined in real time such that an eluted fraction comprising analytes that have changed in concentration can be immediately subjected to further analysis using MS-MS. A difference in the abundance ratio of the first and second isotopically labeled peptides and the normalized abundance ratio is indicative of a difference in concentration in the first and second samples of a protein from which the peptide is derived.

Optionally, the first and second isotopically labeled peptides can include at least one affinity ligand. In that case, the method further includes, prior to determining the abundance ratios, contacting the peptides with a capture moiety to select peptides comprising the at least one affinity ligand. Also optionally, the protein from which the peptide was derived can be identified.

In another aspect, the invention provides a multiplexed method for detecting a difference in the concentration of an analyte of interest present in multiple samples, each sample comprising a plurality of analytes. Preferably, about 3 to about 5 samples are analyzed concurrently. The method includes, for each sample, covalently attaching an isoform of a labeling agent to the analyte of interest to yield an isotopically labeled analyte of interest. Different isoforms of the labeling agent are used for each sample, and the isoforms differ from one another in mass by at least about 3 amu. Preferably, all but at most one isoform include at least one non-deuterium heavy isotope. At least portions of the samples are mixed to yield a combined sample.

The combined sample is subjected to mass spectrometric analysis to determine a normalized abundance ratio characterizing analytes whose concentration is the same in the samples and an abundance ratio of at least one pair of the isotopically labeled analytes of interest. A difference in the abundance ratio of the isotopically labeled analytes of interest and the normalized abundance ratio is indicative of a difference in concentration of the analyte of interest in the samples.

Where the analyte of interest is a protein, the multiplexed method optionally includes cleaving the proteins in the samples to yield at least one peptide of interest derived from the protein of interest. Then, for each sample, an isoform of a labeling agent is covalently attached to the peptide of interest to yield an isotopically labeled peptide of interest.

At least portions of the samples are mixed to yield a combined sample. The combined sample is subjected to mass spectrometric analysis to determine a normalized abundance ratio characterizing peptides derived from proteins whose concentration is the same in the samples and an abundance ratio of at least one pair of the isotopically labeled peptides of interest. A difference in the abundance ratio of the isotopically labeled peptides of interest and the normalized abundance ratio is indicative of a difference in concentration in the samples of a protein from which the peptide is derived. Again, preferably about 3 to 5 samples are analyzed concurrently.

In yet another aspect, the invention provides a method for identifying isoforms of an analyte. Nondeuterated isoforms of the analyte do not resolve during fractionation, and the fractionation yields a plurality of elution peaks. MS can be performed on each elution peak to detect isoforms of the analyte.

(a) Extracted ion chromatogram of the deuterated peptide (▲), non-deuterated peptide (◆), and ratio between them (■); (b) mass spectrum at 50.7 minutes; (c) mass spectrum at 51.2 minutes; (d) mass spectrum at 51.6 minutes; (e) mass spectrum of fraction collected at 50.2-50.8 minutes; (f) mass spectrum of fraction collected at 50.8-51.4 minutes; (g) mass spectrum of fraction collected at 51.4-52.0 minutes.

Figure 7:
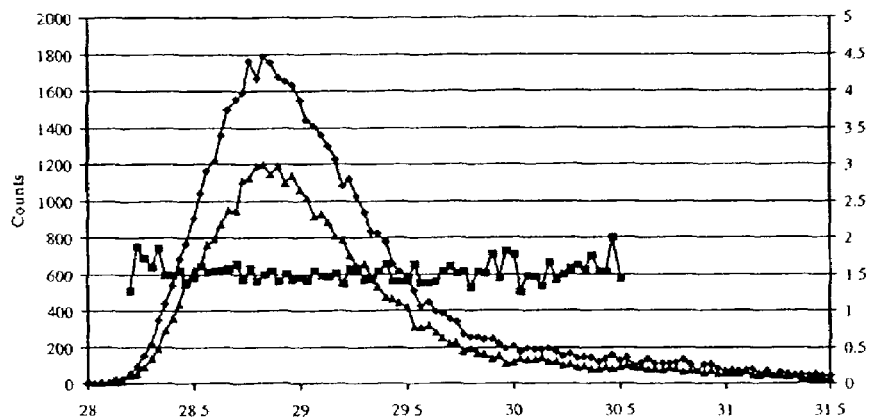
Figure 7:
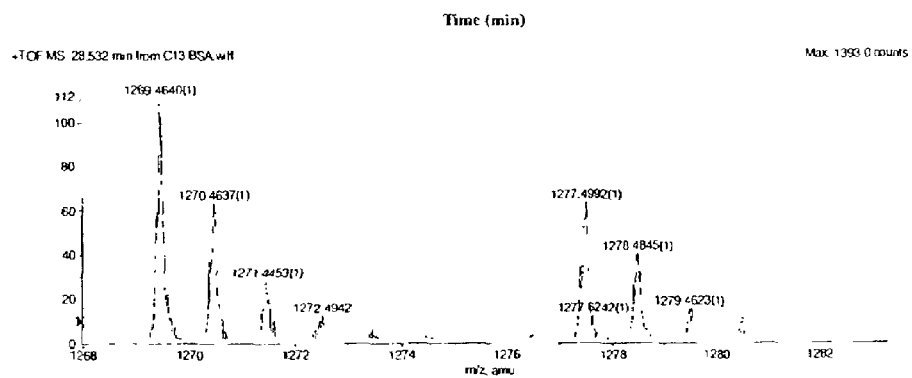
Figure 7:
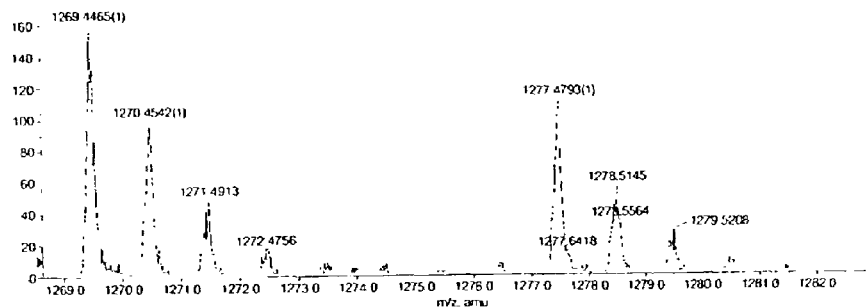
Figure 7:
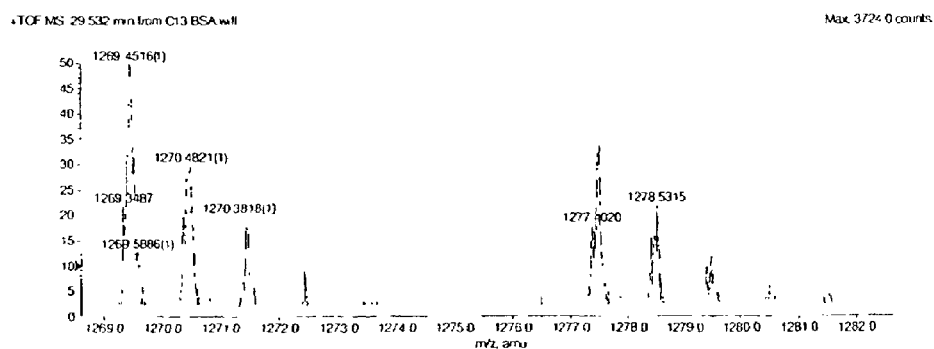

FIG. 7 depicts a pair of succinic anhydride-$^{13}C_0$ and $^{13}C_4$ labeled peptides coelute in revered-phase chromatography. The peptide sequence is QNCDQFEK (SEQ ID NO: 1). Eight $^{13}C$ were incorporated into the heavy isotope labeled peptide. (a) Extracted ion chromatogram of the $^{13}C$-labeled peptide (▲), non-$^{13}C$-labeled peptide (♦), and ratio between them (■); (b) mass spectrum at 28.5 minutes; (c) mass spectrum at 29.0 minutes; (d) mass spectrum at 29.5 minutes.

Figure 8:
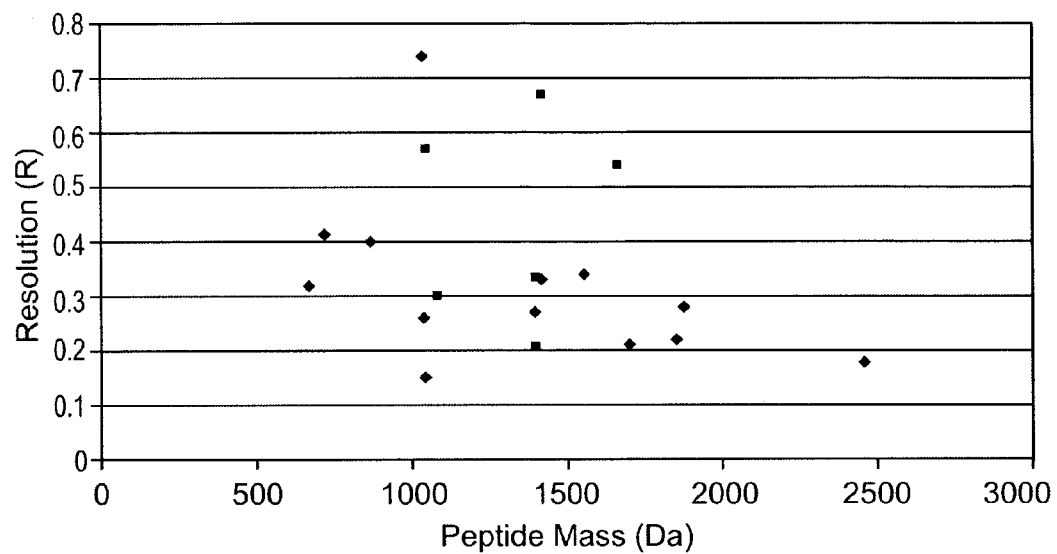

FIG. 8 depicts resolution (R) caused by ICAT-$^2H_8$ of tryptic peptides of BSA. Thirteen peptides contain one cysteine and have 8 deuterium incorporated (♦). Six peptide contain two cysteine and have 16 deuterium incorporated (■).

Figure 9:
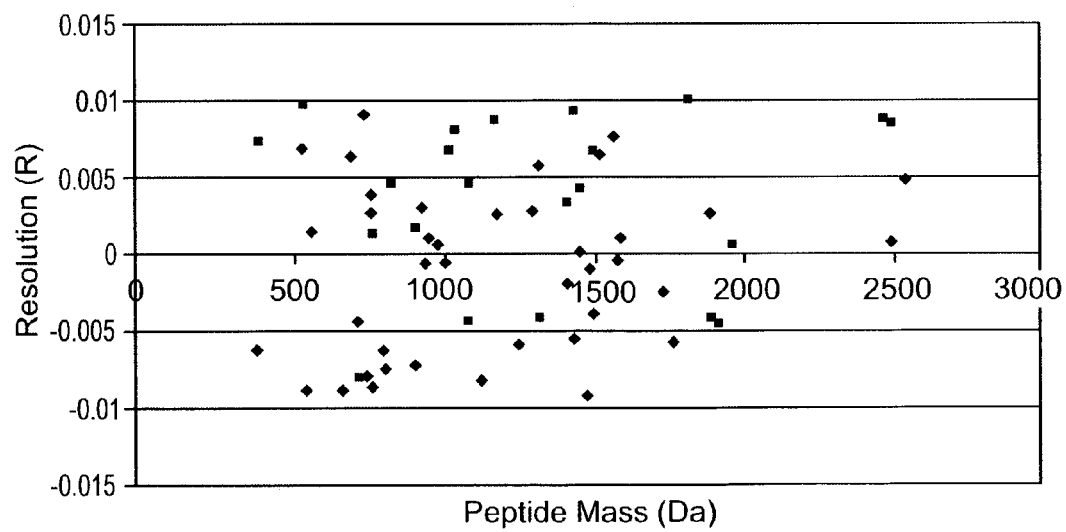

FIG. 9 depicts resolution (R) caused by succinic anhydride-$^{13}C_4$ on tryptic peptides of BSA. Forty-four peptides contain no lysine and have 4 $^{13}C$ incorporated (♦). Twenty-three peptides contain lysine and have 8 $^{13}C$ incorporated (■).

Figure 10A:
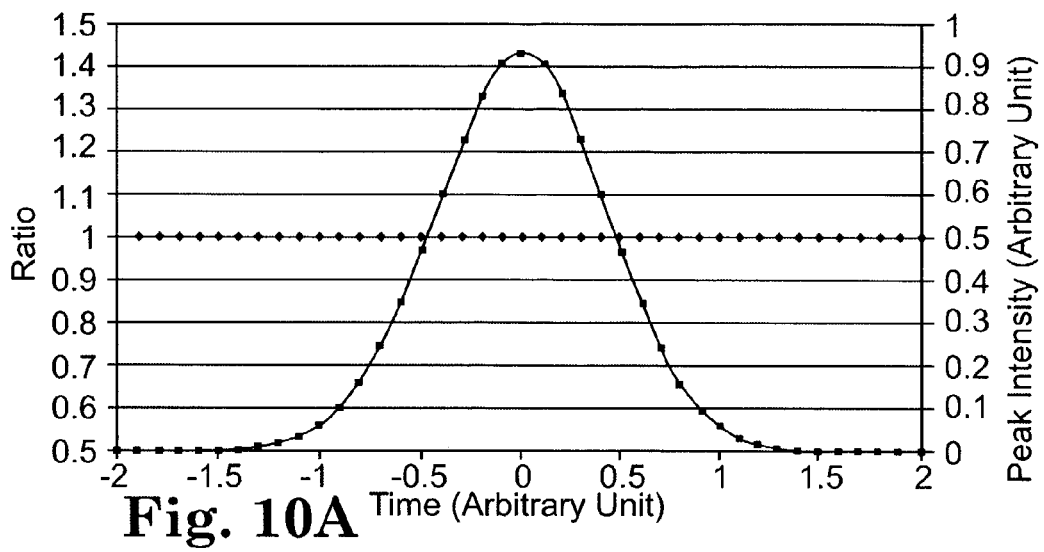
Figure 10B:
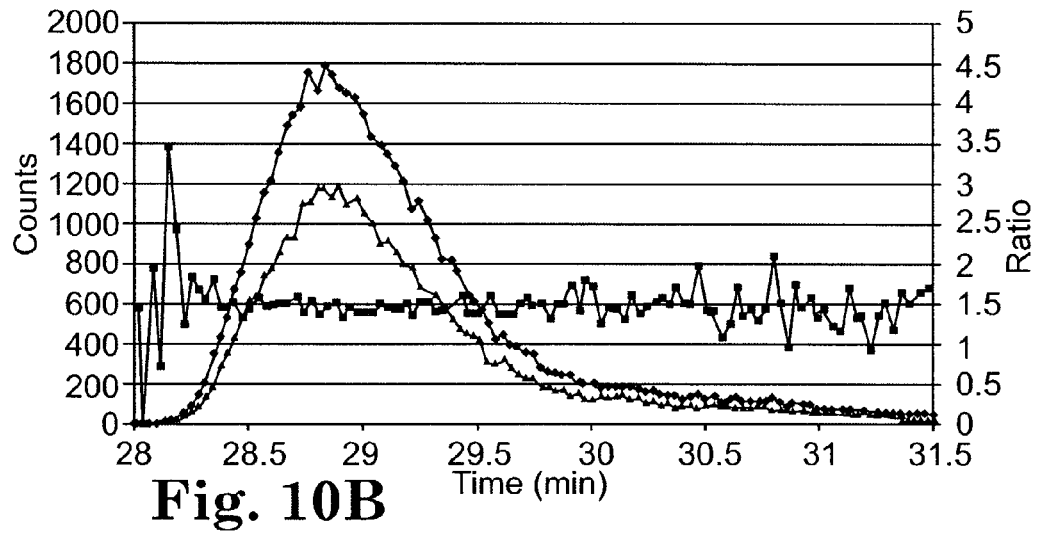

FIG. 10 depicts real-time intelligent data acquisition (IDA) when resolution is negligible. (a) A simulation of abundance ratio (♦) as a function of elution time in a chromatographic separation of isotopically labeled peptides. R=0 and ratio (♦) does not vary with time; (b) A pair of succinic anhydride-$^{13}C_0$ (♦) and $^{13}C_4$ (▲) labeled peptides coelute in reversed-phase chromatography. Ratio (■) is constant in the middle of elution peak where counts are high. Large random errors in ratio (■) exist at both ends of the elution peak where counts are low; (c) ratios settle quickly when ratios are calculated based on cumulative counts, instead of counts in individual mass spectrum. In this case it reaches accurate ratio at approximately 28.5 minutes, which leaves approximately 1 minute (28.5-29.5 minutes) to perform MS/MS analysis if the ratio exceeds preset threshold.

Figure 11A:
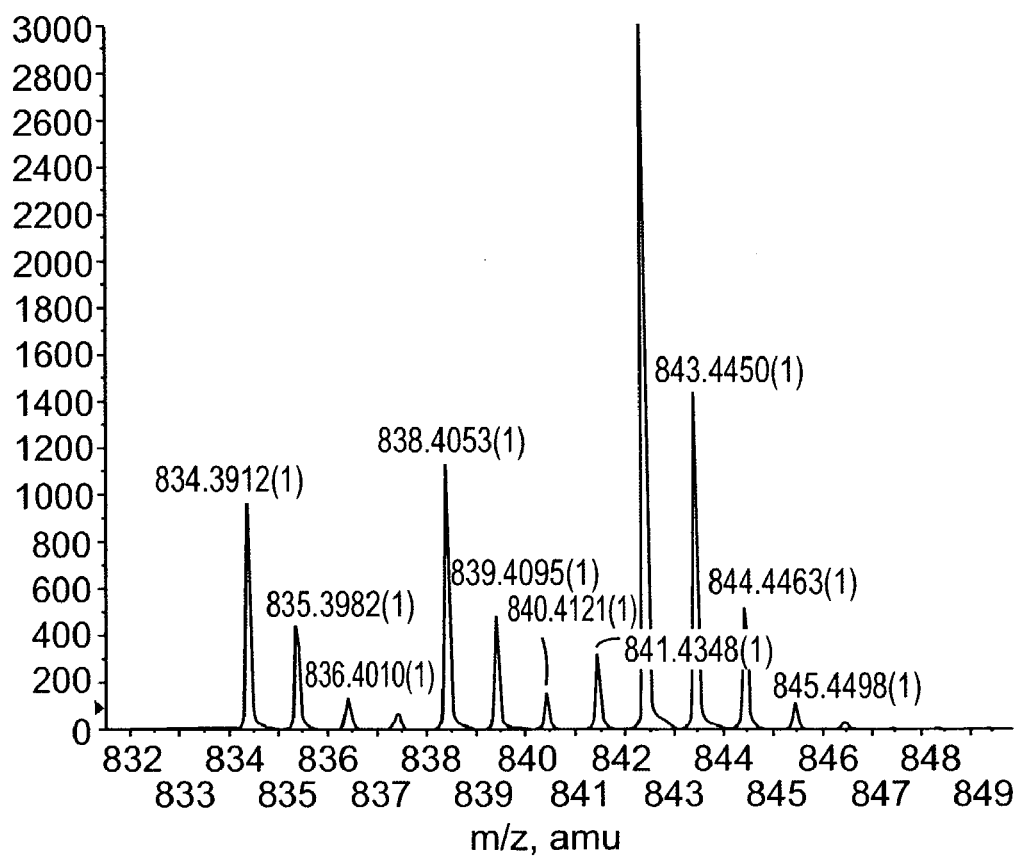
Figure 11B:
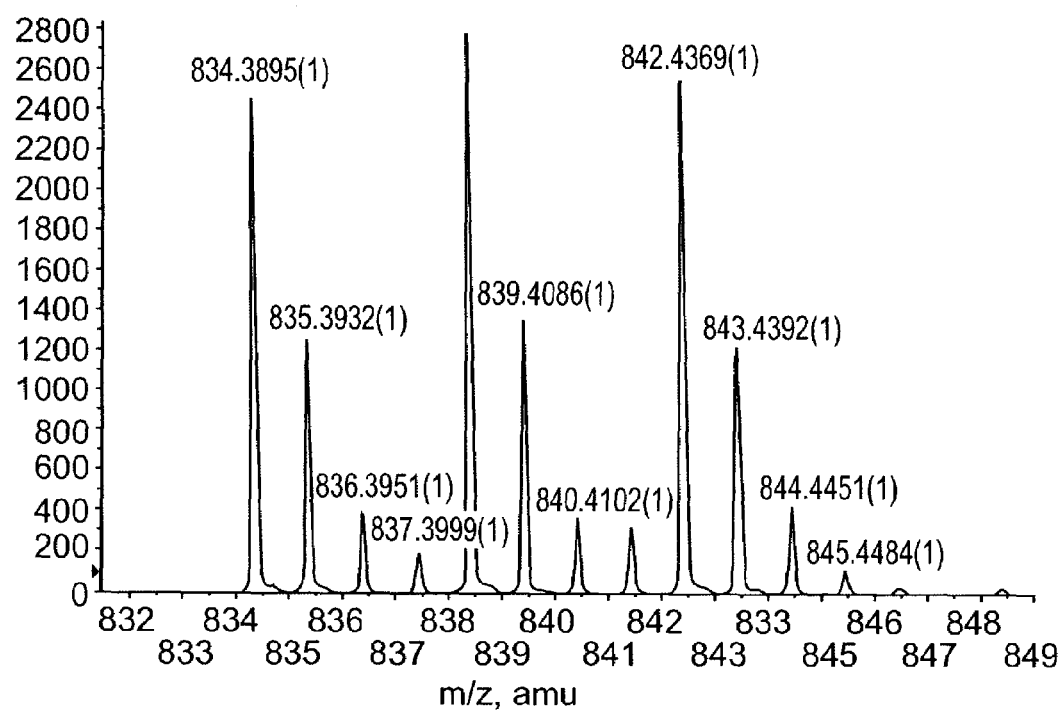
Figure 11C:
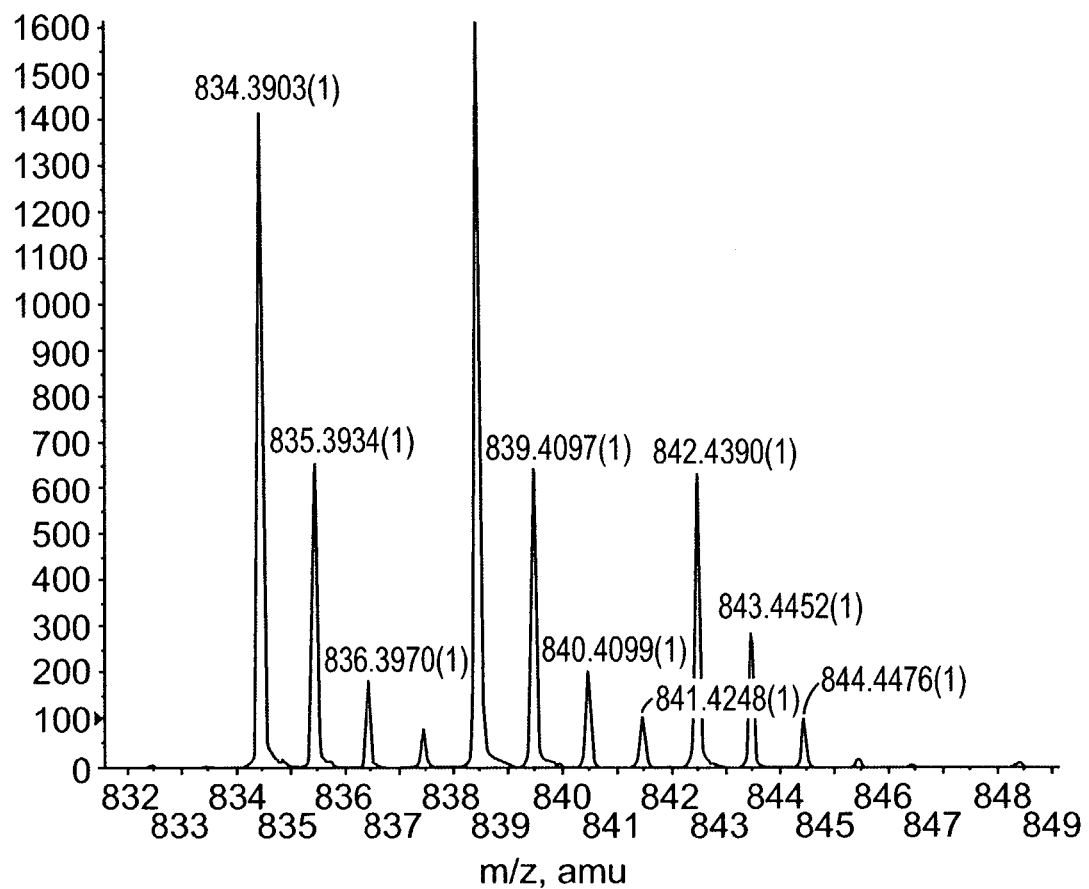

FIG. 11 shows mass spectra of a peptide (IFVQK; SEQ ID NO:2) labeled by succinic anhydride (m/z=834.4, control sample), succinic-$^{13}C_2$-anhydride (m/z=838.4, experimental sample 1) and succinic-$H_4$-anhydride (m/z=842.4, experimental sample 2) at different times: (A) t=39.025 minutes, (B) t=39.125 minutes, (C) t=39.359 minutes.

Figure 12:
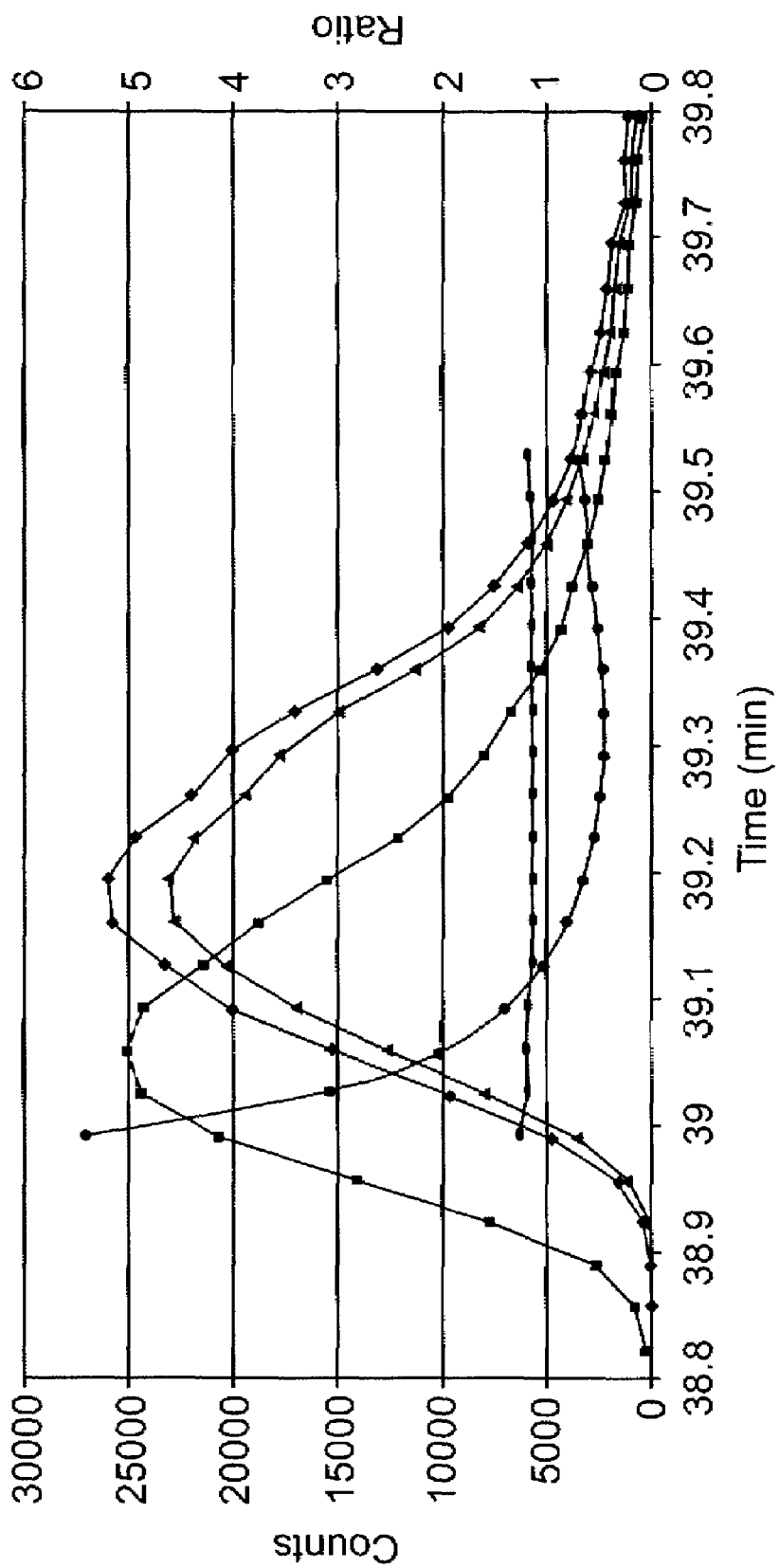

FIG. 12 shows extracted ion chromatograms of the monoisotopic peaks of isotopically labeled peptides in FIG. 11 (▲: m/z=834.4, control sample, ♦: m/z=838.4, experimental sample 1, ■: m/z=842.4, experimental sample 2) and the ratios between experiment and control samples (——: ratio between experimental sample 1 and control sample, (●: ratio between experimental sample 2 and control sample).

FIG. 13 shows the worst cases of each labeling reagent tested in this work. Extracted ion chromatograms of the isotopically labeled peptides (▲: heavy isotope labeled experimental sample, ♦: non-isotope labeled control sample) and the ratios between experiment and control samples derivatized by various reagents (■: ratio); (A) Peptide (YIPGTK; SEQ ID NO:3) labeled by propionate-N-hydroxysuccinimide ester and propionate-$^2H_5$-N-hydroxysuccinimide ester. Ten $^2H$ were incorporated. R equals 1.0; (B) Peptide (YIPGTK; SEQ ID NO:3) labeled by succinic anhydride and succinic-$^2H_4$-anhydride. Eight $^2H$ were incorporated. R equals 0.31; (C) Peptide (IFVQK; SEQ ID NO:2) labeled by N-acetoxysuccinimide and N-acetoxy-$^2H_3$-succinimide. Six $^2H$ were incorporated. R equals 0.27; (D) Peptide (TGPNLHGLFGR; SEQ ID NO:4) labeled by $H_2^{16}O$ and $H_2^{18}O$. Two $^{18}O$ were incorporated. R equals 0.061; (E) Peptide (MIFAGIK; SEQ ID NO:5) labeled by succinic anhydride and succinic-$^{13}C_2$-anhydride. Four $^{13}C$ were incorporated. R equals 0.0096.

FIG. 14 shows derivatization of tryptic peptides of cytochrome c by various reagents. Resolution (R) was found to be dependent on peptide mass; (A) Propionate-N-hydroxysuccinimide ester and propionate-$^2H_5$-N-hydroxysuccinimide ester (■: 10 $^2H$ incorporated, ♦: 5 $^2H$ incorporated); (B) Succinic anhydride and succinic-$^2H_4$-anhydride (■: 8 $^2H$ incorporated, ♦: 4 $^2H$ incorporated); (C) N-acetoxysuccinimide and N-acetoxy-$^2H_3$-succinimide (■: 6 $^2H$ incorporated, ●: 3 $^2H$ incorporated); (D) $H_2^{16}O$ and $H_2^{18}O$; (E) Succinic anhydride and succinic-$^{13}C_2$-anhydride (■: 4 $^2H$ incorporated, ♦: 2 $^2H$ incorporated).

Figure 15:
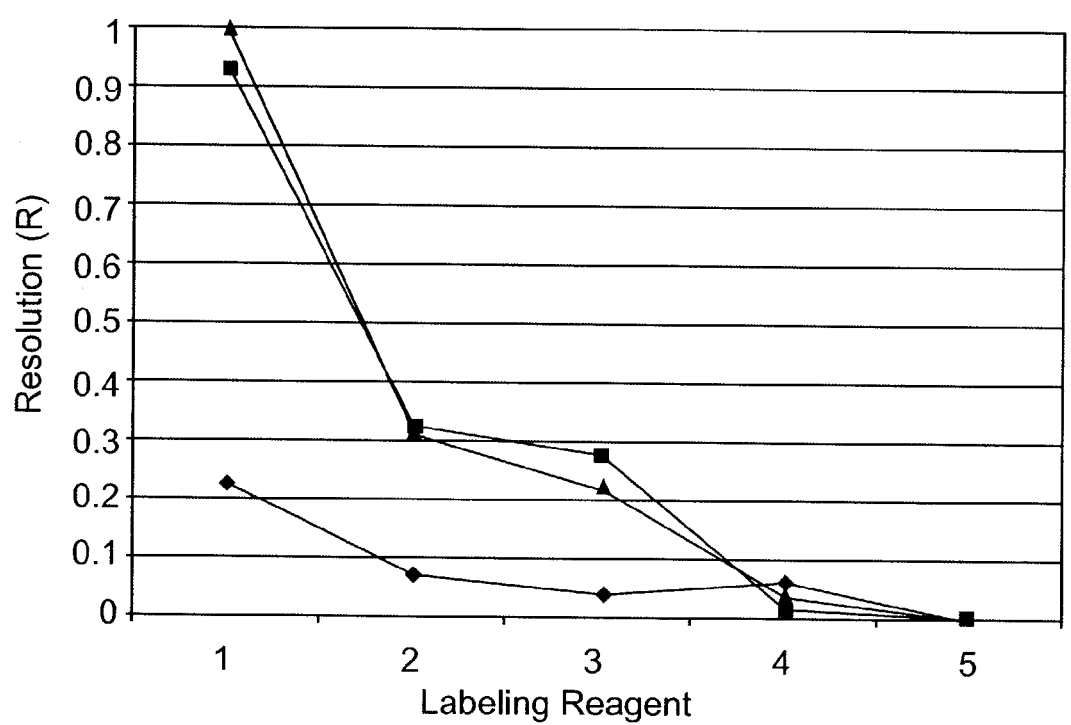

FIG. 15 shows the relationship between resolution (R) and various labeling reagents. 1: propionate-$^2H_5$-N-hydroxysuccinimide ester, 2: succinic-$^2H_4$-anhydride, 3: N-acetoxy-$^2H_3$-succinimide, 4: $H_2^{18}O$, 5: succinic-$^{13}C_2$-anhydride. ▲: YIPGTK (SEQ ID NO:3), ■: IFVQK (SEQ ID NO: 2), ♦: TGPNLHGLFGR (SEQ ID NO:4).

DETAILED DESCRIPTION OF ILLUSTRATIVE EMBODIMENTS

The present invention is directed to materials and methods for minimizing the "isotope effect" during analyte fractionation. Analytes are labeled with non-deuterium isotopes prior to fractionation, resulting in reduction or elimination of the isotope effect.

The invention is especially useful in the area of comparative proteomics, where differential heavy isotope coding methods are used to quantify and identify peptides and proteins in complex mixtures. Minimization of the isotope effect allows the isotope abundance ratio to be measured accurately and quickly, because these ratios can be measured in real time. For example, in comparative proteomics, the invention allows abundance ratios to be determined based on a single mass spectrum taken on-line, in real time, at any point during the reversed phase elution of a complex, isotopically labeled peptide mixture of peptides. Proteins whose abundance ratio differs from the reference ratio can be immediately identified, via MS/MS fragmentation of the peptides.

The ability to make abundance ratio measurements on-line, in real time, represents a tremendous advance in the art of comparative proteomics. For the first time, chromatographic separation such as reversed phase chromatography (RPC) and mass spectrometric analysis can be executed within a single multidimensional chromatographic system. Upstream reduction, alkylation, proteolysis and/or affinity selection can be added as desired. This advance allows more time to be spent on MS/MS of peptides of interest. The system can even be operated without the attention of an operator, relying on intelligent data acquisition and immediate application of an algorithm that specifies that MS/MS be carried out when the abundance ratio exceeds a predetermined threshold.

Elimination of the isotope effect in accordance with the invention also permits the use of a chemically multiplexed global internal standard technique (mGIST). This technique can be use to concurrently analyze analytes in three, four, five and even more samples, provided that multiple isoforms of the labeling agent are available. mGIST is especially useful in comparative proteomics. For example, it allows discrimination among post-translational variants of proteins, and rapid accommodation of the analysis of structural diversity as described in Example 4.

The identical or nearly identical chromatographic retention times of analyte isoforms also serves as one of the criteria to recognize isoform pairs from among multiple analytes with equivalent masses observed using MS. Proteomes are extremely complicated, and many totally irrelevant peptides could appear to be isoform pairs based on mass alone. Without a means to distinguish isoform pairs from other species having the same mass, abundance ratio is calculated and an up/down regulation may be erroneously reported. This kind of erroneous conclusions can be avoided if additional data is available that might otherwise distinguish the species, such as chromatographic retention time, MS/MS spectra, etc.

Isotope Effect

For mass spectrometric analysis of comparative samples as described above, it is desired that the labeled analytes be chemically equivalent but isotopically distinct. Labeled analytes that are chemically equivalent but isotopically distinct are referred to as isotopic isoforms or simply isoforms. Isotopic isoforms are "chemically equivalent" in that they have the same chemical composition and structure; however they are "isotopically distinct" in that at least one atom in a first isoform is substituted with a heavy isotope of that atom in a second isoform. It is evident that many different isoforms of a compound can be synthesized, depending on the number and type of atoms substituted with a heavy isotope of that atom.

Because they are chemically equivalent, isotopic isoforms typically exhibit identical or substantially identical behavior during physical or chemical fractionation processes, such as chromatography or electrophoresis, such that isoforms cannot be readily separated from one another using standard laboratory purification and separation techniques. For example, a protein or peptide present in each sample may, after labeling, differ in mass by a few atomic mass units when the protein or peptide from one sample is compared to the same protein or peptide from the other sample (i.e., they are isotopically distinct). However, these two proteins or peptides would ideally exhibit identical chromatographic behavior and electrophoretic migration patterns.

To the extent isotopic isoforms exhibit non-identical fractionation behavior, this is referred to as the "isotope effect." Unless otherwise indicated, the term "isotope effect," when used herein to describe the behavior of a heavy atom isoform of a compound, means the difference in fractionation behavior of the heavy atom isoform and an isoform of that compound containing no heavy atoms.

A primary objective of the present invention is to reduce or eliminate the isotope effect. Isotope coding agents that contain heavy isotopes other than deuterium in accordance with the invention can be employed to reduce or eliminate the "isotope effect" that characterizes deuterated isoforms.

Labeling Agents and Non-deuterium Mass Isotopes

It has been discovered that the isotope effect is ameliorated when heavy isotopes other than deuterium are used to isotopically code peptides and proteins. As noted in more detail below, this strategy can be used with amino acid specific coding agents, such as the -SH labeling agent known by the tradename "ICAT" (isotope coding affinity tag) (Gygi et al., Nat. Biotechnol. (1999) 17, 994-999), or with the global internal standard technique (GIST) (PCT WO 01/86306, published Nov. 15, 2001, Ji et al., J. Chromatogr. B, (2000) 745, 197-210). Examples of stable mass isotopes (other than deuterium) that can be used to label an analyte include $^{13}C$, $^{15}N$, $^{17}O$, $^{18}O$, $^{33}S$, and $^{34}S$ but should be understood that the invention is in no way limited by the choice of isotope. For purposes of the invention, the term "non-deuterium heavy isotope" includes all stable mass isotopes other than $^2H$.

A heavy isotope can be incorporated into a labeling agent such as an affinity tag, or it can be linked to the peptide or protein in a separate chemical or enzymatic reaction. The term "isotope coding agent" refers to a reagent in the form of, for example, a labeling agent, such as ICAT, containing one or more heavy isotopes, which can be covalently linked to an analyte to isotopically label it. A "labeling agent" is a reagent includes a reactive group capable of covalent linkage to the analyte, such as a peptide or protein, and, optionally, an affinity tag to facilitate selection of the labeled analytes. Affinity selection of peptides is an optional step the comparative analysis of biological metabolites (see below), thus the inclusion of an affinity ligand in the labeling agent is optional.

The term "isotope coding agent" also includes a heavy isotope that is incorporated into a metabolite either post-synthetically, such as $^{18}O$ that is incorporated into proteins and peptides by isotope exchange with $H_2^{18}O$ during proteolysis or deglycosylation, or during biosynthesis, such as by providing a cell with enriched media containing $^{13}C$- or $^{15}N$-labeled amino acids during protein synthesis.

Any labeling agent with known or expected utility as a deuterated isotope coding agent can be employed as an isotope coding agent containing $^{13}C$, $^{18}O$ and/or $^{15}N$ instead of deuterium, provided the labeling agent contains carbon, oxygen and/or nitrogen atoms, respectively. Examples of labeling agents include succinic anhydride and ICAT reagent or derivative thereof.

Biological Samples

Samples analyzed according to the method of the invention are preferably obtained from a "biological environment," which is to be broadly interpreted to include any type of biological system in which enzymatic reactions can occur, including in vitro environments, cell culture, cells at any developmental stage, whole organisms, organs, tissues, bodily fluids, and the like.

Metabolites such as proteins (or peptides if proteolysis is employed) in control and experimental samples are labeled (either post-synthetically or during biosynthesis) with distinct isotopic forms of a labeling agent. In proteomics, MS can be performed on polypeptides of any length. Proteins are typically fragmented into peptides prior to labeling, but whole proteins can be labeled if desired.

The terms "polypeptide," "protein/peptide" and "protein" as used herein are equivalent and include both peptides (i.e., short polypeptides, typically less than about 50 amino acids, more typically less than about 30 amino acids), and longer polypeptides. These terms are used interchangeably. Furthermore, unless otherwise indicated, techniques described with reference to longer polypeptides are equally applicable to shorter polypeptides (peptides), and vice versa. It should be understood that the terms "polypeptide," "protein/peptide" and "protein" refer to a polymer of amino acids and do not connote a specific length of a polymer of amino acids. Thus, for example, the terms oligopeptide, polypeptide, and enzyme are included within the definition of polypeptide, protein/peptide and protein, whether produced using recombinant techniques, chemical or enzymatic synthesis, or naturally occurring. These terms also includes polypeptides that have been modified or derivatized, such as by glycosylation, acetylation, phosphorylation, and the like. When the term "peptide" is used herein, it generally refers to a protein fragment produced in solution.

The method of the invention is especially well-suited for use in complex samples containing a number of different metabolites, although it is applicable to less complex samples as well. In comparative proteomics applications, the sample preferably contains at least about two proteins; more preferably it contains at least about 100 proteins; still more preferably it contains at least about 1000 proteins. A sample can therefore include total cellular protein or some fraction thereof. For example, a sample can be obtained from a particular cellular compartment or organelle, using methods such as centrifugal fractionation. The sample can be derived from any type of cell, organism, tissue, organ, or bodily fluid, without limitation. The method of the invention can be used to identify one or more proteins in the sample, and is typically used to identify multiple proteins in a single complex mixture. It should therefore be understood that when the method of the invention is referred to, for simplicity, as a method for identifying "a protein" in a mixture that contains multiple proteins, the term "a protein" is intended to mean "at least one protein" and thus includes one or more proteins.

Comparative Analysis of Biological Metabolites

There is a growing need to move beyond the massive effort to define genetic and protein components of biological systems to the study of how they and other cellular metabolites are regulated and respond to stimuli. Advantageously, the invention permits faster and more accurate identification, compared to previous methods, of up- and down-regulated metabolites in biological samples in response to the application of a stimulus. The words "stimulus" and "stimuli" are used broadly herein and mean any agent, event, change in conditions or even the simple passage of time that may be associated with a detectable change in expression of at least one metabolite within a cell, without limitation. For example, a stimulus can include a change in growth conditions, disease state, pH, nutrient supply, temperature, electrical or electrochemical environment, or pressure; contact with an exogenous agent such as a drug or microbe, competition with another organism; and the like. The term "metabolite" refers, in this context, to a cellular component, preferably an organic cellular component, which can change in concentration in response to a stimulus, and includes large biomolecules such as proteins, polynucleotides, carbohydrates and fats, as well as small organic molecules such as hormones, peptides, cofactors and the like.

Advantageously, in comparative analysis of biological metabolites according to the invention, it is not necessary to preselect the change in concentration that will be studied; instead, any of the hundreds of thousands or millions of the proteins in the samples can change in relative concentration, and these proteins can be readily identified.

As noted above, labeling of biological metabolites using isotope coding agents that contain heavy isotopes other than, or in addition to, deuterium in accordance with the invention reduces or eliminates the "isotope effect" observed during fractionation of deuterated samples.

Isotopically labeled samples are combined, and the mixture is then fractionated using one or more selection or fractionation techniques. The objective of fractionation is to reduce sample complexity to the extent that abundance ratio analysis can be performed, using a mass spectrometer, on individual analyte pairs. The method is not limited by the techniques used for selection and/or fractionation. Typically, fractionation is carried out using single or multidimensional chromatography such as reversed phase chromatography (RPC), ion exchange chromatography, hydrophobic interaction chromatography, size exclusion chromatography, or affinity fractionation such as immunoaffinity and immobilized metal affinity chromatography. Preferably the fractionation involves surface-mediated selection strategies. Electrophoresis, either slab gel or capillary electrophoresis, can also be used to fractionate the analytes. Examples of slab gel electrophoretic methods include sodium dodecyl sulfate polyacrylamide gel electrophoresis (SDS-PAGE) and native gel electrophoresis. Capillary electrophoresis methods that can be used for fractionation include capillary gel electrophoresis (CGE), capillary zone electrophoresis (CZE) and capillary electrochromatography (CEC), capillary isoelectric focusing, immobilized metal affinity chromatography and affinity electrophoresis.

Because >95% of cellular proteins do not change in response to a stimulus, proteins (as well as other metabolites) in flux can be readily identified by abundance ratio changes in species resolved, for example, by 2-D gel electrophoresis or liquid chromatography. Once these proteins are detected, they can optionally be identified using the "signature peptide" approach as described in (PCT WO 01/86306, published Nov. 15, 2001, Ji et al., *J. Chromatogr. B*, (2000) 745, 197-210) or any other convenient method. One example of how this method of the invention can be used is to analyze patterns of protein expression in a breast cancer cell before and after exposure to a candidate drug. The method can also be used to analyze changes in protein expression patterns in a cell or an organism as a result of exposure to a harmful agent. As yet another example, the method can be used to track the changes in protein expression levels in a cell as it is exposed, over time, to changes in light, temperature, electromagnetic field, sound, humidity, and the like.

Post-synthetic isotope labeling of proteins advantageously creates internal standards from proteins of unknown structure and concentration. Whenever there is a control, or reference state, in which the concentration of proteins is at some reference level, proteins in this control state can serve as internal standards. In a preferred embodiment of the invention, constituent peptides are labeled after proteolytic cleavage proteins in the sample. The timing of the labeling step provides an opportunity to label every peptide in the mixture by choosing a labeling method that labels at the N or the C terminus of a polypeptide, in what is referred to as the "Global Internal Standard Technique" or "GIST". The GIST strategies exploit the facts that 1) proteolysis generates primary amine and carboxyl groups during peptide bond hydrolysis, 2) primary amines are easily acetylated with N-acetoxysuccinimide, and 3) $^{18}O$ is easily incorporated into carboxyl groups during proteolysis. However, it should be noted that the resolution of some $^{18}O$ labeled peptides was larger than with $^{2}H$ labeled coding reagents.

Isotopic labeling after the proteins have been synthesized has a further advantage. Although metabolic incorporation of labeled amino acids has been widely used to label proteins and is not to be excluded from the invention, it is not very reproducible and is objectionable in human subjects. Post-sampling strategies for incorporation of labels are much more attractive.

An advantage of the internal standard method is that it detects relative changes in, not changes in absolute amounts of, analytes. It is very difficult to determine changes in absolute amounts analytes that are present at very low levels. This method is as sensitive to changes in very dilute analytes as it is those that are present at great abundance. Another important advantage of this approach is that it is not influenced by quenching in the MALDI. This means that large number of peptides can be analyzed irrespective of the expected quenching.

In comparative proteomics applications, it is often advantageous to cleave proteins in a sample into their constituent peptides at some point prior to mass spectrometric analysis. Fragmentation of proteins can be achieved by chemical, enzymatic or physical means, including, for example, sonication or shearing. Preferably, a protease enzyme is used, such as trypsin, chymotrypsin, papain, gluc-C, endo lys-C, proteinase K, carboxypeptidase, calpain, subtilisin and pepsin; more preferably, a trypsin digest is performed. Alternatively, chemical agents such as cyanogen bromide can be used to effect proteolysis. The proteolytic agent can be immobilized in or on a support, or can be free in solution.

In one embodiment of the method of the invention, proteins are isotopically labeled prior to cleavage. For example, proteins in a control sample can be derivatized with a labeling agent that contains a heavy isotope (an isotope coding agent), while proteins in an experimental sample can be derivatized with the normal labeling agent. The samples are then combined for further analysis. The derivatized proteins can be chemically or enzymatically cleaved, if desired, either before or after fractionation. Cleavage is optional; isotopically labeled proteins can, if desired, be analyzed directly following a fractionation step such as multidimensional chromatography, 2-D electrophoresis or affinity fractionation.

When the derivatized proteins are cleaved before fractionation, the labeling agent preferably contains an affinity ligand, and the tagged peptide fragments are first affinity selected, then fractionated in a 1-D or 2-D chromatography system, after which they are analyzed using mass spectrometry (MS). In instances where the derivatized proteins are cleaved after fractionation, 2-D gel electrophoresis is preferably used to separate the proteins. If the peptides have also been affinity labeled, selection of the affinity-tagged peptides can be performed either before or after electrophoresis.

Mass spectrometric analysis can be used to determine peak intensities and quantitate abundance ratios in the combined sample, determine whether there has been a change in the concentration of a protein between two samples, and to facilitate identification of a protein from which a peptide fragment, preferably a signature peptide, is derived. Preferably, changes in peptide concentration between the control and experimental samples are determined by abundance ratio MALDI-mass spectrometry because MALDI-MS allows the analysis of more complex peptide mixtures, but ESI-MS may also be used when the peptide mixture is not as complex.

In a complex combined mixture, there may be hundreds to thousands of peptides, and many of them will not change in concentration between the control and experimental samples. These peptides whose levels are unchanged are used to establish the normalized abundance ratio for peptides that were neither up nor down regulated. All peptides in which the abundance ratio exceeds this value are up regulated. In contrast, those in which the ratio decreases are down regulated. A difference in relative abundance ratio of a peptide pair, compared to peptide pairs derived from proteins that did not change in concentration, thus signals a protein whose expression level did change between the control and experimental samples. If the peptide characterized by an abundance ratio different from the normalized ratio is a signature peptide, this peptide can be used according to the method of the invention to identify the protein from which it was derived.

If desired, isotope labeling can take place after cleavage of the proteins in the two samples. Derivatization of the peptide fragments is accomplished using a labeling agent that preferably contains an affinity ligand. On the other hand, an affinity ligand can be attached to the peptides in a separate reaction, either before or after isotopic labeling. If attached after isotopic labeling, the affinity ligand can be attached before or after the samples are combined. The peptide fragments in the combined mixture are affinity selected, then optionally fractionated using a 1-D or multi-dimensional chromatography system, or a capillary or slab gel electrophoretic technique, after which they are analyzed using mass spectrometry. In instances where the peptides are not affinity tagged, they are either affinity selected based on their inherent affinity for an immobilized ligand (preferably using IMAC or immobilized antibody or lectin) or analyzed without selection.

Post-synthetic Isotope Labeling Techniques

1. Alkylation with Isotopically Distinct Reagents

It is often desirable to protect free thiols by alkylation after reduction and prior to fractionation and mass spectrometry. Accordingly, proteins or other thiol-containing metabolites in control and experimental samples are optionally alkylated using alkylating agents. The alkylating agent can double as an isotope coding agent, in which case different isoforms of the alkylating agent are used for control and experimental samples.

Iodoacetic acid ($ICH_2COOH$) is an example of an alkylating agent. Normal iodoacetate can be used to derivative the control, for example, and $^{13}C$ iodoacetate can be used to derivatize the experimental sample. Preferably, the $^{13}C$ isoform contains two atoms of $^{13}C$.

Based on the fact that proteins from control and experimental samples are identical in all respects except the isotopic content of the iodoacetate alkylating agent, their relative molar response (U) is expected to be 1. This has several important ramifications. When control and experimental samples are mixed:

$$A = \Lambda \Delta$$

In this case $\Delta$ will be i) the same for all the proteins in the mixture that do not change concentration in the experimental sample and ii) a function of the relative sample volumes mixed. If the protein concentration in the two samples is the same and they are mixed in a 1/1 ratio for example, then $\Delta=1$. With a cellular extract of 20,000 proteins, $\Delta$ will probably be the same for >19,900 of the proteins in the mixture. The concentration of a regulated protein that is either up- or down-regulated is expressed by the equation:

$$A_{exptl} = \Lambda_{contl} \Delta \delta$$

where $A_{exptl}$ is a protein from the experimental sample that has been synthetically labeled with a derivatizing agent, $\Lambda_{contl}$ is the same protein from the control sample labeled with a different isotopic form of the derivatizing agent, and $\delta$ is the relative degree of up- or down-regulation. Because $\Delta$ is an easily determined constant derived from the concentration ratio of probably >95% of the proteins in a sample, $\delta$ is readily calculated and proteins in regulatory flux easily identified.

Another example of an alkylating agent that is useful for isotope coding is an ICAT (isotope coding affinity tag) reagent. An ICAT reagent includes a reactive functional group that reacts with an amine, a thiol, a hydroxyl or a carboxyl; an isotopic linker; and, optionally, an affinity functional group for affinity selection. The "linker" links the reactive functional group and the optional affinity functional group. In a preferred embodiment, the reactive function group is reactive group such as iodoacetic acid or iodocetamide, capable of covalent linkage to a thiol-containing metabolite such as a protein or peptide.

For example, an ICAT reagent can alkylate the free cysteines in a protein or peptide. An affinity tag, such as biotin, facilitates selection of the tagged compounds. To function as an isotope coding agent, an ICAT reagent further includes an isotopically labeled linker, e.g., $C_{10}H_{17}N_3O_3$, which can carry up to ten $^{13}C$ atoms, three $^{18}O$ atoms or three $^{15}N$ atoms, or any combination thereof. An ICAT reagent containing a linker having nine $^{13}C$ isotopes is a particularly preferred embodiment of the invention and can be obtained from Applied Biosystems, Inc.

The ICAT reagent of the invention is very versatile isotope coding agent and is expected to be useful in experiments utilizing the multiplexed global internal standard technique (mGIST) as described in more detail below.

It should be understood that the ICAT reagent is not limited by the particular isotopic linker, and that linkers other than $C_{10}H_{17}N_3O_3$ can be used. Optionally, the ICAT reagent also includes a cleavage site that allows removal of the affinity portion of the label and part of the linker reducing the overall mass of the tag on the peptides and improving the overall peptide fragmentation efficiency.

2. Isotopic Labeling of Amines

If not included as part of the alkylating agent, an isotope label can be applied to the peptide or other metabolite as part of an affinity tag (if affinity selection is contemplated), or at some other reactive site on the peptide. Although application of the internal standard isotopic label in the affinity tag is operationally simpler and, in some cases, more desirable, it requires that each affinity tag be synthesized in at least two isotopic forms. Amine-labeling in a separate step (i.e., uncoupling the label and the affinity ligand) is therefore a preferred alternative.

Peptides that are generated by trypsin digestion (as well as those generated by many other types of cleavage reactions) have a primary amino group at their amino-terminus in all cases except those in which the peptide originated from a blocked amino-terminus of a protein. Moreover, the specificity of trypsin cleavage dictates that the C-terminus of signature peptides will have either a lysine or arginine (except the C-terminal peptide from the protein). In rare cases there may also be a lysine or arginine adjacent to the C-terminus.

Primary amino groups are easily acylated with, for example, acetyl N-hydroxysuccinimide (ANHS). Indeed, any analyte having a carboxyl group can be activated by NHS then derivatized with a labeling agent that having a free amine. Control samples can be acetylated with normal ANHS whereas experimental tryptic digests can be acylated with either $^{13}CH_3CO$—NHS or other $^{13}C$-containing derivatizing agent. Our studies show that the ε-amino group of all lysines can be derivatized in addition to the amino-terminus of the peptide, as expected. This is actually an advantage in that it allows a determination of the number of lysine residues in the peptide.

Essentially all peptides in both samples will be derivatized and hence distinguishable from their counterparts using mass spectrometry. This means that any affinity selection method or combination of affinity selection methods (other than possibly those that select for arginine or lysine, which contain free amines) can be used at any point in the process to obtain a selected population enriched for signature peptides. For example, isotope labeling at amines can be used to identify changes in the relative amounts of peptides selected on the basis of cysteine, tryptophan, histidine, and a wide variety of post-translational modifications. In this preferred embodiment of the method, isotopic labeling and affinity labeling are two independent and distinct steps, and virtually all peptides are isotopically labeled. This provides significantly more flexibility and greater control over the production of signature peptides than is possible when the alkylating agent doubles as the isotope labeling agent.

3. Isotopic Labeling of Hydroxyls and Other Functional Groups

While acetylation is a convenient labeling method for proteins and their constituent peptides, other labeling methods may be useful for other types of cellular metabolites. For example, acetic anhydride can be used to acetylate hydroxyl groups in the samples, and trimethylchlorosilane can be used for less specific labeling of functional groups including hydroxyl groups, carboxylate groups and amines.

Mass Spectrometry

Masses of the fractionated metabolites are preferably determined by mass spectrometry, preferably using matrix assisted laser desorption ionization (MALDI) or electrospray ionization (ESI), and mass of the peptides is analyzed using time-of-flight (TOF), quadrapole, ion trap, magnetic sector or ion cyclotron resonance mass analyzers, or a combination thereof including, without limitation, TOF-TOF and other combinations. The mass of peptides analyzed in comparative proteomics applications is preferably determined with a mass accuracy of about 10 ppm or better; more preferably, masses are determined with a mass accuracy of about 5 ppm or better; most preferably they are determined with a mass accuracy of about 1 ppm or better. The lower the ppm value, the more accurate the mass determination and the less sequence data is needed for peptide identification.

Interpretation of the Spectra

Isotopic isoforms of a metabolite from control and experimental samples that have been mixed together will exhibit identical, or nearly identical, behavior during fractionation prior to mass spectrometry and will not be resolved. A mass spectrometer, however, can readily differentiate between species labeled with a heavy isotope and normal species. In proteomics applications, mass spectometric analysis of isoforms present as either as proteolytic fragments or as a low molecular weight (e.g., under about 15 kD) proteins allows ratios of protein abundance ("abundance ratios") between the two samples to be established. The relative abundance of most proteins will be the same and allow Δ to be calculated. A second group of proteins will be seen in which the relative abundance of specific proteins is much larger in the experimental sample. These are the up-regulated proteins. In contrast, a third group of proteins will be found in which the relative abundance of specific proteins is lower in the experimental sample. These are the down-regulated proteins. The degree (δ) to which proteins are up- or down-regulated is calculated based on the computed value of Δ.

A more detailed analysis of the interpretation of the resulting mass spectra is provided using amine-labeled proteins as an example. Signature peptides of experimental samples in this example are acetylated at the amino-termini and on ε-amino groups of lysines with either $^{13}CH_3CO$- or $CD_3CO$- residues, therefore any particular peptide will appear in the mass spectrum as a doublet. Although this example employs deuterium as the heavy isotope, it is readily applicable to isotope labeling with non-deuterium heavy isotopes in accordance with the invention, to reduce the isotope effect in fractionation procedures prior to mass spectrometry.

In the simplest case, which involves the use of deuterium as the heavy and is thus presented here for illustrative purposes only, where i) trideutero-acetic acid is used as the labeling agent, ii) the C-terminus is arginine, iii) there are no other basic amino acids in the peptide, and iv) the control and experimental samples are mixed in exactly a 1/1 ratio before analysis, i.e., Δ=1, the spectrum shows a doublet with peaks of approximately equal height separated by 3 amu. With 1 lysine the doublet peaks were separated by 6 amu and with 2 lysine by 9 amu. For each lysine that is added the difference in mass between the experimental and control would increase an additional 3 amu. It is unlikely in practice that mixing would be achieved in exactly a 1/1 ratio. Thus Δ will have to be determined for each sample and varies some between samples. Within a given sample, Δ will be the same for most peptides, as will also be the case in electrophoresis. Peptides that deviate to any extent from the average value of Δ are the ones of interest. The extent of this deviation is the value δ, the degree of up- or down-regulation. As indicated above, Δ will be the same for greater than 95% of the proteins, or signature peptides in a sample.

As noted above, amino acids with other functional groups are occasionally labeled. In the presence of a large excess of acylating agent hydroxyl groups of serine, threonine, tyrosine, and carbohydrate residues in glycoconjugates and the imidazole group of histidine can also be derivatized. This does not interfere with quantification experiments, but complicates interpretation of mass spectra if groups other than primary amines are derivatized. In the case of hydroxyl groups, esters formed in the derivatization reaction are readily hydrolyzed by hydroxylamine under basic conditions. Acylation of imadazole groups on the other hand occurs less frequently than esterification and is perhaps related to amino acid sequence around the histidine residue.

Another potential problem with the interpretation of mass spectra in the internal standard method of the invention can occur in cases where a protein is grossly up- or down-regulated. Under those circumstances, there will essentially be only one peak. When there is a large down-regulation this peak will be the internal standard from the control. In the case of gross up-regulation, this single peak will have come from the experimental sample. The problem is how to know whether a single peak is from up- or down-regulation. This is addressed by double labeling the control with $CH_3CO$—NHS and $^{13}CH_3CO$—NHS. Because of the lysine issue noted above, it is necessary to split the control sample into two lots and label them separately with $CH_3CO$—NHS and $^{13}CH_3CO$—NHS, respectively, and then remix. When this is done the control always appears as a doublet separated by 1-2 amu, or 3 amu in the extreme case where there are two lysines in the peptide. When double labeling the control with $^{12}C$ and $^{13}C$ acetate and the experimental sample with trideuteroacetate, spectra would be interpreted as follows. A single peak in this case would be an indicator of strong up-regulation. The presence of the internal standard doublet alone would indicate strong down-regulation.

Another potential problem with the double labeled internal standard is how to interpret a doublet separated by 3 amu. Because the control sample was labeled with $CH_3CO$—NHS and $^{13}CH_3CO$—NHS, this problem can arise only when the signature peptide has 2 lysine residues and is substantially down-regulated to the point that there is little of the peptide in the experimental sample. The other feature of the doublet would be that the ratio of peak heights would be identical to the ratio in which the isotopically labeled control peptides were mixed. Thus, it may be concluded that any time a doublet appears alone in the spectrum of a sample and A is roughly equivalent to that of the internal standard that i) the two peaks came from the control sample and ii) peaks from the experimental sample are absent because of substantial down regulation.

Microfabricated Analytical Systems

The method of the invention is amenable to automation by integrating most of the analytical steps in a single instrument. Reduction, alkylation, proteolysis, affinity selection, and reversed phase chromatography (RPC), or any subset thereof, can be executed within a single multidimensional chromatographic system. Samples collected from this system are manually transferred to MALDI plates for mass spectrometric analysis. In one embodiment, the invention provides a single channel integrated system. In a preferred embodiment, however, the invention thus provides a microfabricated, integrated, parallel processing, microfluidic system that carry out all the separation components of analysis on a single chip.

Real-time Intelligent Data Acquisition and Analysis (IDA)

Proteolysis of a proteome produces very large numbers of peptides and identifying all these peptides by MS/MS is a lengthy, formidable task. However, studies have shown that only a small percentage of all the proteins in a proteome change significantly in concentration as a result of some stimulus. When the objective it to identify only those proteins that have undergone change (comparative proteomics), throughput and data quality could be greatly improved by fragmenting only those peptides of interest. Real-time abundance ratio analysis would allow a mass spectrometer (MS) and data system to select peptides for MS/MS sequencing based on changes in relative concentration that exceed preset values.

Minimizing the isotope effect by controlling "R", the difference in elution times between isoforms, using the techniques described herein allows "real time ratio analysis" so that decisions regarding further (e.g., MS) analysis of chromatographic peaks can be made in real time. R (resolution) is defined as the differences between the retention times divided by the average peak width at half maximum.

$$R = \frac{t_2 - t_1}{w_{1/2}}$$

Further analysis is initiated only on the peptides or proteins whose changes (as evidenced by the abundance ratio) exceed the preset values. With real-time abundance ratio analysis, the amount of data that needs to be analyzed is substantially reduced, and throughput can be doubled.

There are a number of ways to do "real time ratio analysis". Using $^{13}C$ coding agents, which essentially exhibit no isotope effect, the abundance ratio does not change significantly across the LC elution peak, so the ratio can be determined by a single snapshot in MS. Although isotopically labeled isoforms of peptides are not resolved in the case of $^{13}C$ coding, large random errors in abundance ratio are often seen at both the leading and tailing edges of eluting peaks where concentration and counts are low. In the middle of a peak, however, counts are high. It is often desirable, however, to determine the abundance ratio as early as possible, preferably prior to the elution of the middle of the peak. One way to improve the accuracy of an early abundance ratio determination is to carry out the following steps.

Figure 6:
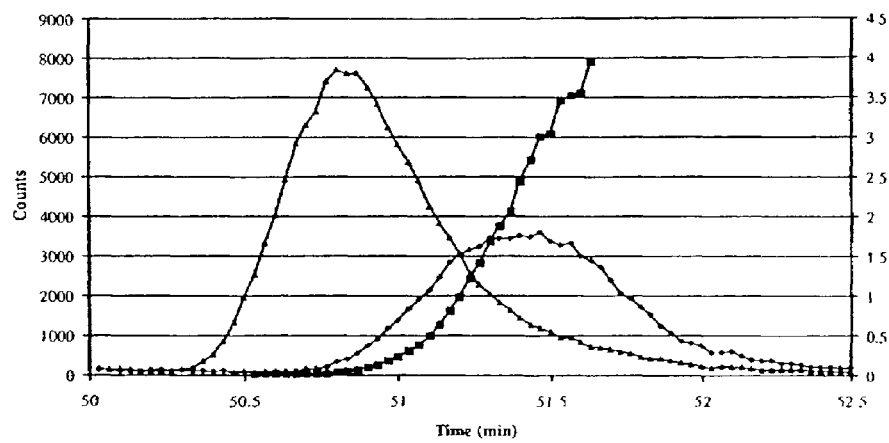
FIG. 6 depicts fractionation of a pair of ICAT-$^2H_0$ and $^2H_8$ labeled peptides in reversed-phase chromatography. The peptide sequence is QNCDQFEK (SEQ ID NO: 1). Eight deuterium were incorporated into the deuterated peptide. Resolution equals 0.74.
Figure 6:
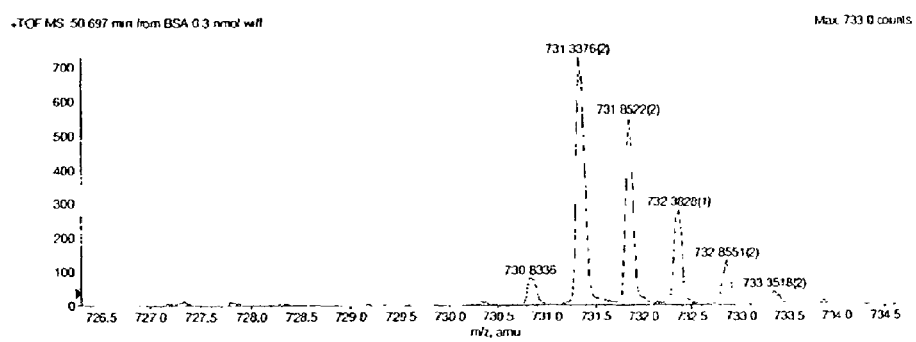
Figure 6:
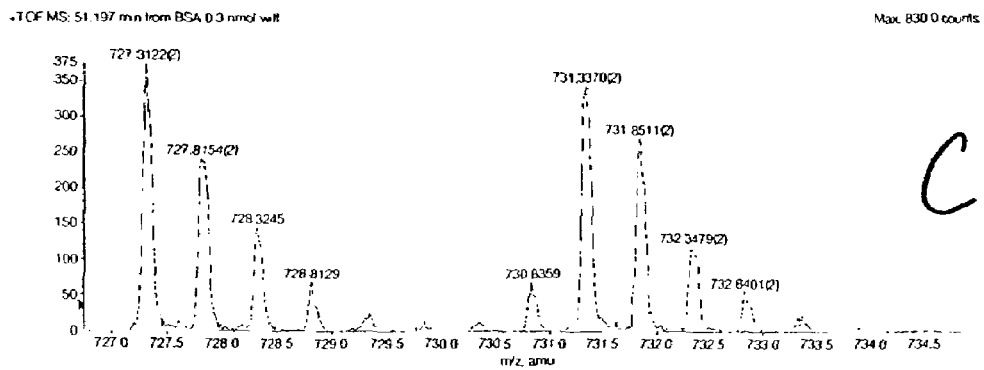
Figure 6:
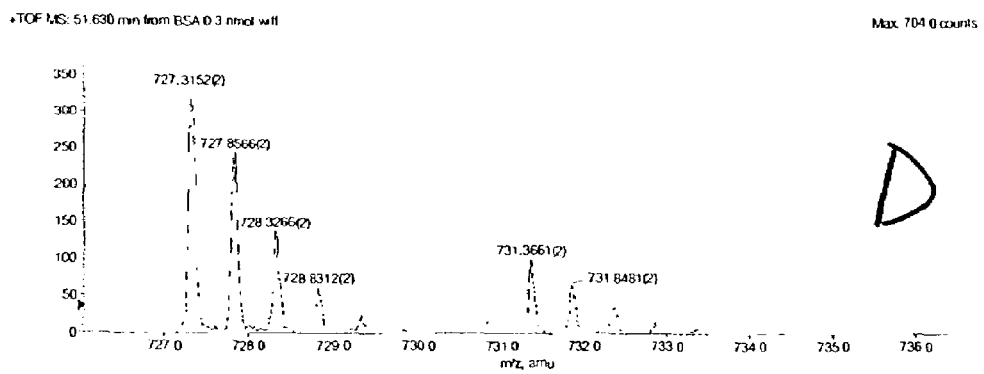
Figure 6:
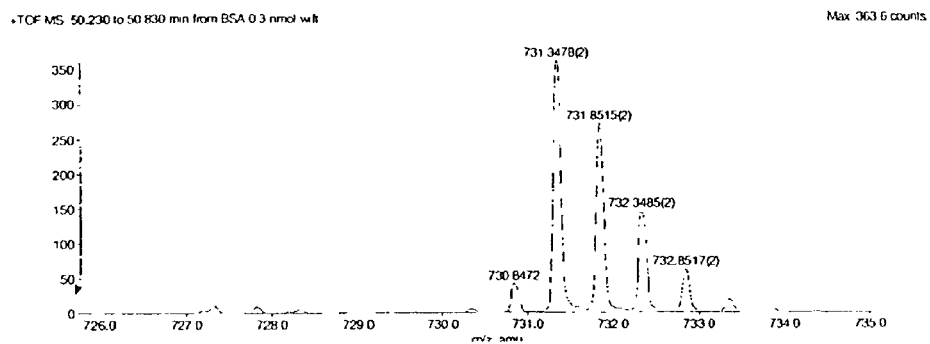
Figure 6:
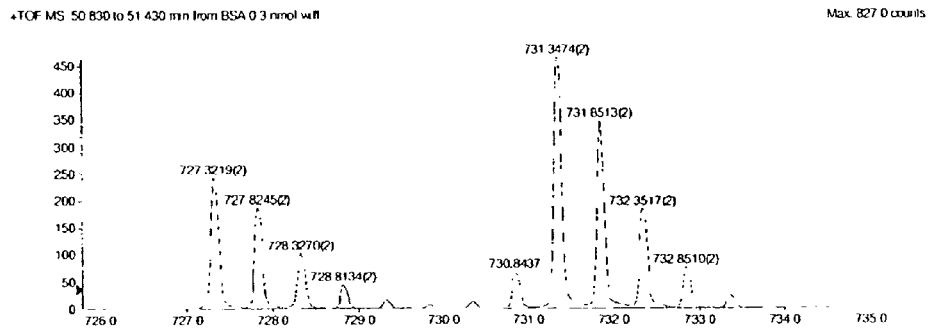
Figure 6:
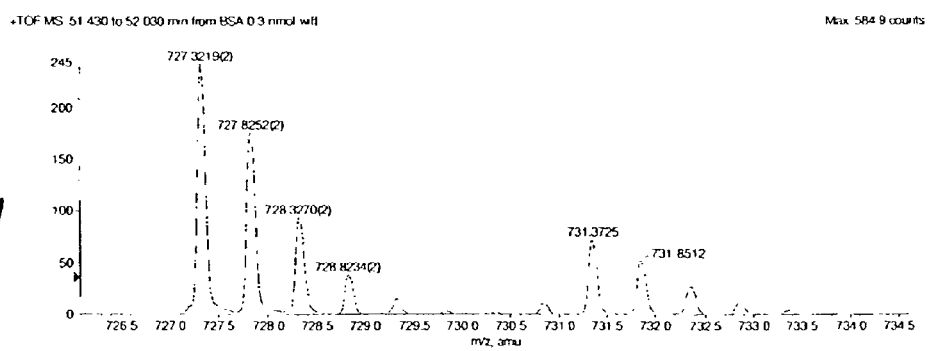
Figure 10C:
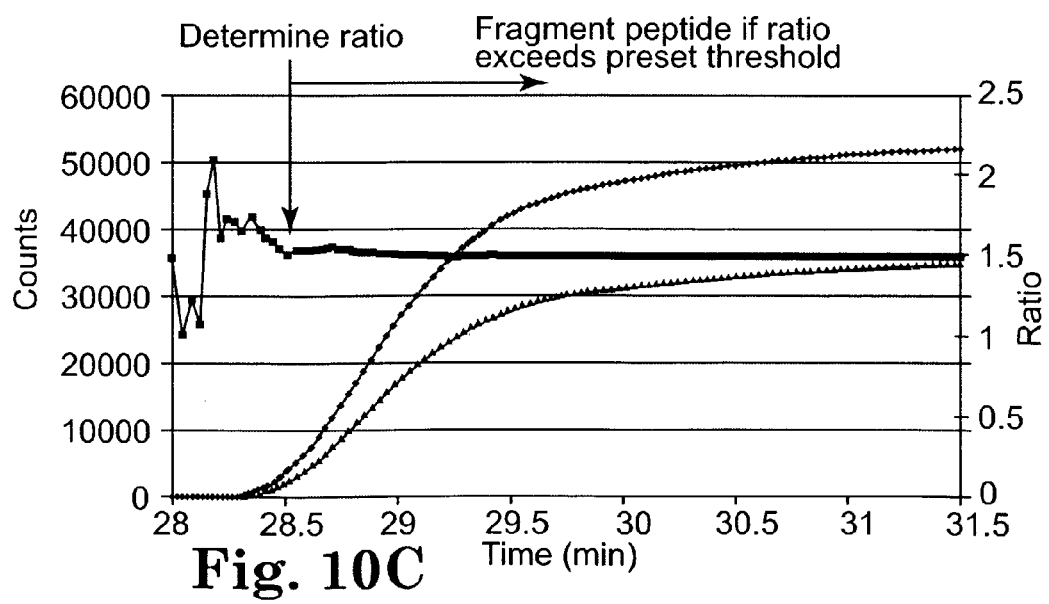

First, identify pairs of isotopically labeled peptides (isoform pairs) based on the mass differences, similar peak profile, constant abundance ratio across time, etc. Using non-deuterium isotopes such as 13C helps to identify of isoform pairs correctly, because the retention time of the isoforms should be the same. This means that the abundance ratio should be constant across the elution peak. If it is observed that the retention times are not the same, or on the other hand the abundance ratio is very different across the peak, it means the suspected isoform pair may not be a true pair, or perhaps that one of them is overlapped with other peptides, and the pair is not "pure." Second, trace accumulative counts of both isotopically labeled peptides. Third, average the ratio between the accumulated counts of subsequent measurements when they reach a preset level. Finally, perform an MS/MS analysis when the ratio exceeds the preset threshold. An example is seen in FIG. 10C of Example II. The ratio could be determined accurately at 28.5 minutes, which leaves approximately 1 minute for further analysis of the peptides if the ratio exceeds a preset threshold. The ratio could be determined even earlier if the intensities of the peptides are higher than in FIG. 6.

For reagents that produce a small isotope effect (e.g. $^{18}$O), the elution peaks of the isotopically labeled peptides can be tracked individually, and once they both reach the peak maximum, the first half of the elution peaks (from the start of the peak to the peak maximum) are integrated, the abundance ratio is calculated based on the integrated areas, and a decision is made whether further analysis need to be performed by MS.

Although abundance ratio would be the primary selection criterion, difference in mass between ion clusters could also be used. For example, peptides labeled with succinate in Example II varying by 4 amu contained a C-terminal arginine while those varying by 8 amu contained a C-terminal lysine. As more coding agents become available, it is likely that different types of derivatization will be coded by this mass shift technique.

Real-time IDA increases throughput, reduces sample consumption, and improves the quality of MS/MS data because more time can be spent on the peptides of interest. Isotopically labeled peptides can be fragmented together when resolution is small, which could help to identify the y and b ion series. For example, y ions are paired with mass differences of 4 Da and b ions are unpaired when the carboxyl terminus of the tryptic peptides are labeled by $^{18}$O during trypsin digestion.

Software Development

Software currently in use in some commercially available instruments instructs mass spectrometers to perform real-time MS-MS on the species that give the most intense signals in mass spectrum. Typically the top 3 signals are analyzed. The software directs selective fragmentation of the most intense isoform pairs, and ignores all the singlets. This scheme reduces the number of unnecessary MS/MS experiments by 50%. However, the most intense signal doesn't necessarily mean that species has the highest concentration. Moreover, those metabolites that are most abundant may not be the ones that have significant change in relative concentration.

The present invention allows real-time MS/MS to be performed on those isoforms that evidence a change in relative concentration, regardless of abundance as long as the abundance is sufficient to rise above the level of random error. By focusing on changed ratios, which include the singlets, it is expected that MS/MS experiments can be reduced by about 80%.

The isotope labeling method of the invention allows the identification of the small number of proteins (peptides) in a sample that are in regulatory flux. Observations of spectra with 50 or fewer peptides indicate that individual species generally appear in the spectra as bundles of peaks consisting of the major peptide ion followed by the $^{13}$C isotope peaks. Once a peak bundle has been located, peak ratios within that bundle are evaluated and compared with adjacent bundles in the spectrum. Based on the isotopes used in labeling, simple rules can be articulated for the identification of up- and down-regulated peptides in mass spectra. Software can be written that apply these rules for interpretation.

Data processed in this way can be evaluated in several modes. One is to select a given peptide and then locate all other peptides that are close in $\delta$ value. All peptides from the same protein should theoretically have the same $\delta$ value (i.e., the same relative degree of up- or down-regulation). For example, when more than one protein is present in the same 2-D gel spot there is the problem of knowing which peptides came from the same protein. The $\delta$ values are very useful in this respect, and provide an additional level of selection. The same is true in 2-D chromatography. 3-D regulation maps of chromatographic retention time vs. peptide mass vs. $\delta$ can also be constructed. This identifies proteins that are strongly up- or down-regulated without regard to the total amount of protein synthesized. In some experiments, one or more groups of proteins may be identified that have similar $\delta$ values, and identification of the members of a group may elucidate metabolic pathways that had not previously been characterized.

Construction of Temporal Maps

The discussion above would imply that regulation is a process that can be understood with single measurements, i.e., after a stimulus has been applied to a biological system one makes a measurement to identify what has been regulated. However, single measurements at the end of the process only identify the cast of characters. Regulation involves adjusting, directing, coordinating, and managing these characters. The issue in regulation is to understand how all these things occur. Regulation is a temporal process involving a cascade of events. Consider, for example, the hypothetical case in which an external stimulus might cause modification of a transcription factor, which then interacts with another transcription factor, the two of which initiate transcription of one or more genes, which causes translation, and finally post-translational modification to synthesize another transcription factor, etc. Temporal analysis brings a lot to understanding this process. Global analysis of protein synthesis in response to a variety of stimuli has been intensely examined and at least two mapping strategies have been developed (R. VanBogelen et al., in F. Neidhardt et al., Ed. *Escherichia coli and Salmonella: Cellular and Molecular Biology*, 2nd Ed. ASM Press, Washington D.C., pp. 2067-2117); H. Zhang et al., J. Mass Spec. 31:1039-1046 (1996)).

A temporal map of protein expression can be constructed by first identifying all species that change in response to a stimulus, then performing a detailed analysis of the regulatory process during protein flux. Identification of those proteins affected by the stimulus is most easily achieved by a single measurement after the regulatory event is complete and everything that has changed is in a new state of regulation. Both chromatographic and electrophoretic methods can be used to contribute to this level of understanding. The regulatory process during protein flux is then analyzed at short time intervals and involves many samples. The initial identification process yields information on which species are in flux, their signature peptides, and the chromatographic behavior of these peptides. As a result, the researcher thus knows which samples contain specific signature peptides and where to find them in mass spectra. Quantitating the degree to which their concentration has changed with the internal standard method is straightforward. The resulting data allows temporal maps of regulation to be constructed, and the temporal pattern of regulation will provide information about the pathway of response to the stimulus. The invention thus further provides a method for developing algorithms that identify signature peptides in regulatory change.

Affinity Selection

Affinity selection, although optional, is useful to help identify which proteins in a complex mixture have undergone up- or down-regulation as a result of the application of a stimulus. Preferably, an affinity selection process is used to select peptide fragments that contain specific amino acids, thereby substantially reducing the number of sample components that must be subjected to further analysis. The affinity selection can be effected using an affinity ligand that has been covalently attached to the protein (prior to cleavage) or its constituent peptides (after cleavage), or using an endogenous affinity ligand.

The affinity selection is preferably based on low abundance amino acids or post-translational modifications so as to preferentially isolate "signature peptides." Peptides from complex proteolytic digests that contain low abundance amino acids or specific post-translational modifications are selected (purified) to reduce sample complexity while at the same time aiding in the identification of peptides selected from the mixture. Selection of peptide fragments that contain cysteine, tryptophan, histidine, methionine, tyrosine, tyrosine phosphate, serine and threonine phosphate, O-linked oligosaccharides, or N-linked oligosaccharides, or any combination thereof can be achieved. It is also possible to determine whether the peptide has a C-terminal lysine or arginine and at least one other amino acid.

The method is not limited by the affinity selection method(s) employed and nonlimiting examples of affinity selections are described herein and can also be found in the scientific literature, for example in M. Wilchek, *Meth. Enzymol.* 34, 182-195 (1974). This approach enormously reduces the complexity of the mixture. If desired, two or more affinity ligands (e.g., primary and secondary affinity ligands) can be used, thereby allowing a finer selection.

Preferably, the affinity selected peptides are subjected to a fractionation step to further reduce sample size prior to the determination of peptide masses. A premise of the signature peptide strategy is that many more peptides are generated during proteolysis than are needed for protein identification. This assumption means that large numbers of peptides potentially can be eliminated, while still leaving enough for protein identification.

Affinity Tags

An affinity tag used for selection can be endogenous to the protein, or it can be added by chemical or enzymatic processes. The term "affinity tag," as used herein, refers to a chemical moiety that functions as, or contains, an affinity ligand that is capable of binding (preferably noncovalently, but covalent linkages are contemplated also) to a second, "capture" chemical moiety, such that a protein or peptide that naturally contains or is derivatized to include the affinity tag can be selected (or "captured") from a pool of proteins or peptides by contacting the pool with the capture moiety. The capture moiety is preferably bound to a support surface, preferably a porous support surface, as a stationary phase. Examples of suitable supports include porous silica, porous titania, porous zirconia, porous organic polymers, porous polysaccharides, or any of these supports in non-porous form.

Preferably the interactions between the affinity tag and the capture moiety are specific and reversible (e.g., noncovalent binding or hydrolyzable covalent linkage), but they can, if desired, initially be, or subsequently be made, irreversible (e.g., a nonhydrolyzable covalent linkage between the affinity tag and the capture moiety). It is important to understand that the invention is not limited to the use of any particular affinity ligand.

Examples of endogenous affinity ligands include naturally occurring amino acids such as cysteine (selected with, for example, an acylating reagent) and histidine, as well as carbohydrate and phosphate moieties. A portion of the protein or peptide amino acid sequence that defines an antigen can also serve as an endogenous affinity ligand, which is particularly useful if the endogenous amino acid sequence is common to more than one protein in the original mixture. In that case, a polyclonal or monoclonal antibody that selects for families of polypeptides that contain the endogenous antigenic sequence can be used as the capture moiety. An antigen is a substance that reacts with products of an immune response stimulated by a specific immunogen, including antibodies and/or T lymphocytes. As is known in the art, an antibody molecule or a T lymphocyte may bind to various substances, for example, sugars, lipids, intermediary metabolites, autocoids, hormones, complex carbohydrates, phospholipids, nucleic acids, and proteins. As used herein, the term "antigen" means any substance present in a peptide that may be captured by binding to an antibody, a T lymphocyte, the binding portion of an antibody or the binding portion of T lymphocyte.

A non-endogenous (i.e., exogenous) affinity tag can be added to a protein or peptide by, for example, first covalently linking the affinity ligand to a derivatizing agent to form an affinity tag, then using the affinity tag to derivatize at least one functional group on the protein or peptide. Alternatively, the protein or peptide can be first derivatized with the derivatizing agent, then the affinity ligand can be covalently linked to the derivatized protein or peptide at a site on the derivatizing agent.

An example of an affinity ligand that can be covalently linked to a protein or peptide by way chemical or enzymatic derivatization is a peptide, preferably a peptide antigen or polyhistidine. A peptide antigen can itself be derivatized with, for example, a 2,4-dinitrophenyl or fluorescein moiety, which renders the peptide more antigenic. A peptide antigen can be conveniently captured by an immunosorbant that contains a bound monoclonal or polyclonal antibody specific for the peptide antigen. A polyhistidine tag, on the other hand, is typically captured by an IMAC column containing a metal chelating agent loaded with nickel or copper.

Biotin, preferably ethylenediamine terminated biotin, which can be captured by the natural receptor avidin, represents another affinity ligand. Other natural receptors can also be used as capture moieties in embodiments wherein their ligands serve as affinity ligands. Other affinity ligands include dinitrophenol (which is typically captured using an antibody or a molecularly imprinted polymer), short oligonucleotides, and polypeptide nucleic acids (PNA) (which are typically captured by nucleic acid hybridization). Molecularly imprinted polymers can also be used to capture.

The affinity ligand is typically linked to a chemical moiety that is capable of derivatizing a selected functional group on a peptide or protein, to form an affinity tag. An affinity ligand can, for example, be covalently linked to maleimide (a protein or peptide derivatizing agent) to yield an affinity tag, which is then used to derivatize the free sulfhydryl groups in cysteine, as further described below.

Selecting Cysteine-containing Peptides

As noted above, is a common strategy to alkylate the sulfhydryl groups in a protein before proteolysis. Alkylation is generally based on two kinds of reactions. One is to alkylate with a reagent such as iodoacetic acid (IAA) or iodoacetamide (IAM). The other is to react with vinyl pyridine, maleic acid, or N-ethylmaleimide (NEM). This second derivatization method is based on the propensity of -SH groups to add to the C=C double bond in a conjugated system. Alkylating agents linked to an affinity ligand double as affinity tags and can be used to select cysteine containing peptides after, or concomitant with, alkylation. For example, affinity-tagged iodoacetic acid is a convenient selection for cysteine.

Optionally, the protein is reduced prior to alkylation to convert all the disulfides (cystines) into sulfhydryls (cysteines) prior to derivatization. Alkylation can be performed either prior to reduction (permitting the capture of only those fragments in which the cysteine is free in the native protein) or after reduction (permitting capture of the larger group containing all cysteine-containing peptides, include those that are in the oxidized cystine form in the native protein).

Preparation of an affinity tagged N-ethylmaleimide may be achieved by the addition of a primary amine-containing affinity tag to maleic anhydride. The actual affinity tag may be chosen from among a number of species ranging from peptide antigens, polyhistidine, biotin, dinitrophenol, or polypeptide nucleic acids (PNA). Peptide and dinitrophenol tags are typically selected with an antibody whereas the biotin tag is selected with avidin. When the affinity tag includes as the affinity ligand a peptide, and when proteolysis of the protein mixture is accomplished after derivatization using trypsin or lys-C, the peptide affinity ligand preferably does not contain lysine or arginine, so as to prevent the affinity ligand from also being cleaved during proteolysis. Biotin is a preferred affinity ligand because it is selected with very high affinity and can be captured with readily available avidin/streptavidin columns or magnetic beads. As noted above, polyhistidine tags are selected in an immobilized metal affinity chromatography (IMAC) capture step. This selection route has the advantage that the columns are much less expensive, they are of high capacity, and analytes are easily desorbed.

Alternatively, cysteine-containing peptides or proteins can be captured directly during alkylation without incorporating an affinity ligand into the alkylating agent. An alkylating agent is immobilized on a suitable substrate, and the protein or peptide mixture is contacted with the immobilized alkylating agent to select cysteine-containing peptides or proteins. If proteins are selected, proteolysis can be conveniently carried out on the immobilized proteins to yield immobilized cysteine-containing peptides. Selected peptides or proteins are then released from the substrate and subjected to further processing in accordance with the method of the invention.

When alkylation is done in solution, excess affinity tagged alkylating agent is removed prior to selection with an immobilized capture moiety. Failure to do so will severely reduce the capacity of the capture sorbent. This is because the tagged alkylating agent is used in great excess and the affinity sorbent cannot discriminate between excess reagent and tagged peptides. This problem is readily circumvented by using a small size exclusion column to separate alkylated proteins from excess reagent prior to affinity selection. The whole process can be automated (as further described below) by using a multidimensional chromatography system with, for example, a size exclusion column, an immobilized trypsin column, an affinity selector column, and a reversed phase column. After size discrimination the protein is valved through the trypsin column and the peptides in the effluent passed directly to the affinity column for selection. After capture and concentration on the affinity column, tagged peptides are desorbed from the affinity column and transferred to the reversed phase column where they were again captured and concentrated. Finally, the peptides are eluted with a volatile mobile phase and fractions collected for mass spectral analysis. Automation in this manner has been found to work well.

Selecting Tyrosine-containing Peptides

Like cysteine, tyrosine is an amino acid that is present in proteins in limited abundance. It is known that diazonium salts add to the aromatic ring of tyrosine ortho to the hydroxyl groups; this fact has been widely exploited in the immobilization of proteins through tyrosine. Accordingly, tyrosine-containing peptides or proteins can be affinity-selected by derivatizing them with a diazonium salt that has been coupled at its carboxyl group to a primary amine on an affinity ligand, for example through the α-amino group on a peptide tag as described above. Alternatively, that diazonium salt can be immobilized on a suitable substrate, and the protein or peptide mixture is contacted with the immobilized diazonium salt to select tyrosine-containing peptides or proteins. If proteins are selected, proteolysis can be conveniently carried out on the immobilized proteins to yield immobilized tyrosine-containing peptides. Selected peptides or proteins are then released from the substrate and subjected to further processing in accordance with the method of the invention.

Selecting Tryptophan-containing Peptides

Tryptophan is present in most mammalian proteins at a level of <3%. This means that the average protein will yield only a few tryptophan containing peptides. Selective derivatization of tryptophan has been achieved with 2,4-dinitrophenylsulfenyl chloride at pH 5.0 (M. Wilcheck et al., *Biochem. Biophys. Acta* 178:1-7 (1972)). Using an antibody directed against 2,4-dinitrophenol, an immunosorbant was prepared to select peptides with this label. The advantage of tryptophan selection is that the number of peptides will generally be small.

Selecting Histidine-containing Peptides

In view of the higher frequency of histidine in proteins, it would seem at first that far too many peptides would be selected to be useful. The great strength of the procedure outlined below is that it selects on the basis of the number of histidines, not just the presence of histidine. Immobilized metal affinity chromatography (IMAC) columns loaded with copper easily produce ten or more peaks. The fact that a few other amino acids are weakly selected is not a problem, and the specificity of histidine selection can, if desired, be greatly improved by acetylation of primary amino groups. Fractions from the IMAC column are transferred to an RPC-MALDI/MS system for analysis. The number of peptides that can potentially be analyzed jumps to 100,000-300,000 in the IMAC approach.

An automated IMAC-RPC-MALDI/MS system essentially identical to that used for cysteine selection has been assembled. The only difference is in substituting an IMAC column for the affinity sorbent and changes in the elution protocol. Gradient elution in these systems is most easily achieved by applying step gradients to the affinity column. After reduction, alkylation, and digestion, the peptide mixture is captured on the IMAC column loaded with copper. Peptides are isocratically eluted from the IMAC using imidazole or a change in pH, and directly transferred to the RPC column where they are concentrated at the head of the column. The IMAC is then taken off line, the solvent lines of the instrument purged at 10 ml/minute for a few seconds with RPC solvent A, and then the RPC column is gradient eluted and column fractions collected for MALDI-MS. When this is done, the RPC column is recycled with the next solvent for step elution of the IMAC column, the IMAC column is then brought back on line, and the second set of peptides is isocratically eluted from the IMAC column and transferred to the RPC column where they are readsorbed. The IMAC column is again taken off-line, the system purged, and the second set of peptides is eluted from the RPC column. This process is repeated until the IMAC column has been eluted. Again, everything leading up to MALDI-MS is automated.

Selecting Post-translationally Modified Proteins

Post-translational modification plays an important role in regulation. For this reason, it is necessary to have methods that detect specific post-translational modifications. Advantageously, the method of the invention can distinguish among proteins having a single signature peptide where speciation occurs by post-translational modification, if the affinity ligand is associated with, or constitutes, the post-translational moiety (e.g., sugar residue or phosphate). Among the more important post-translational modifications are i) the phosphorylation of tyrosine, serine, or threonine; ii) N-glycosylation; and iii) O-glycosylation.

Selecting Phosphoproteins

In the case of phosphorylated proteins, such as those containing phosphotyrosine and phosphoserine, selection can achieved with monoclonal antibodies that target specific phosphorylated amino acids. For example, immunosorbant columns loaded with a tyrosine phosphate specific monoclonal antibody are commercially available. Preferably, all proteins in a sample are digested, then the immunosorbant is used to select only the tyrosine phosphate containing peptides. As in other selection schemes, these peptides can separated by reversed phase chromatography and subjected to MALDI.

Alternatively, selection of phosphopeptides can be achieved using IMAC columns loaded with gallium (M. Posewitz et al., *Anal. Chem.* 71(14):2883-2992 (1999)). Phosphopeptides can also be selected using anion exchange chromatography, preferably on a cationic support surface, at acidic pH.

In addition, because zirconate sorbents have high affinity for phosphate containing compounds (C. Dunlap et al., *J. Chromatogr. A* 746:199-210 (1996)), zirconia-containing chromatography is expected to be suitable for the purification of phosphoproteins and phosphopeptides. Zirconate clad silica sorbents can be prepared by applying zirconyl chloride dissolved in 2,4-pentadione to 500 angstrom pore diameter silica and then heat treating the support at 400EC. Another alternative is the porous zirconate support recently described by Peter Carr (C. Dunlap et al., *J. Chromatogr. A* 746:199-210 (1996)). Phosphopeptides are eluted using a phosphate buffer gradient. In many respects, this strategy is the same as that of the IMAC columns.

Selecting O-linked Oligosaccharide Containing Peptides

Glycopeptides can be selected using lectins. For example, lectin from *Bandeiraea simplicifolia* (BS-II) binds readily to proteins containing N-acetylglucosamine. This lectin is immobilized on a silica support and used to affinity select O-glycosylated proteins, such transcription factors, containing N-acetylglucosamine and the glycopeptides resulting from proteolysis. The protocol is essentially identical to the other affinity selection methods described above. Following reduction and alkylation, low molecular weight reagents are separated from proteins. The proteins are then tryptic digested, the glycopeptides selected on the affinity column, and then the glycopeptides resolved by RPC. In the case of some transcription factors, glycosylation is homogeneous and MALDI-MS of the intact glycopeptide is unambiguous. That is not the case with the more complex O-linked glycopeptides obtained from many other systems. Heterogeneity of glycosylation at a particular serine will produce a complex mass spectrum that is difficult to interpret. Enzymatic deglycosylation of peptides subsequent to affinity selection is indicated in these cases. Deglycosylation can also be achieved chemically with strong base and is followed by size exclusion chromatography to separate the peptides from the cleaved oligosaccharides.

It is important to note that O-linked and N-linked glycopeptides are easily differentiated by selective cleavage of serine linked oligosaccharides (E. Roquemore et al., *Meth. Enzymol.* 230:443-460 (1994)). There are multiple ways to chemically differentiate between these two classes of glycopeptides. For example, basic conditions in which the hemiacetal linkage to serine is readily cleaved can be utilized. In the process, serine is dehydrated to form an $\alpha,\beta$ unsaturated system (C=C—C=O). The C=C bond of this system may be either reduced with $NaBH_4$ or alkylated with a tagged thiol for further affinity selection. This would allow O-linked glycopeptides to be selected in the presence of N-linked glycopeptides. The same result could be achieved with enzymatic digestion.

Selecting N-linked Oligosaccharide-containing Peptides

As with O-linked oligosaccharide-containing peptides, lectins can be used to affinity select N-linked glycopeptides following reductive alkylation and proteolysis. To avoid selecting O-linked glycopeptides, the peptide mixture is subjected to conditions that cause selective cleavage O-linked oligosaccharides prior to affinity selection using the lectin. Preferably O-linked deglycosylation is achieved using a base treatment after reductive alkylation, followed by size exclusion chromatography to separate the peptides from the cleaved oligosaccharides. To address the potential problem of heterogeneity of glycosylation, and N-linked glycopeptides are deglycosylated after selection. Automation can be achieved with immobilized enzymes, but long residence times in the enzyme columns are needed for the three enzymatic hydrolysis steps.

Identification of Signature Peptides and their Parent Proteins

After peptides of interest are detected using mass spectrometry, for example by identifying and determining the mass of those peptides that show a different abundance ratio, it is often desired to identify the protein from which a peptide originated. In most instances this can be accomplished using a standard protocol that involves scanning either protein or DNA databases for amino acid sequences that would correspond to the proteolytic fragments generated experimentally, matching the mass of all possible fragments against the experimental data (F. Hsieh et al., *Anal. Chem.* 70:1847-1852 (1998); D. Reiber et all, *Anal. Chem* 70:673-683 (1998)). When a DNA database is used as a reference database, open reading frames are translated and the resulting putative proteins are cleaved computationally to generate the reference fragments, using the same cleavage method that was used experimentally. Likewise, when a protein database is used, proteolytic cleavage is also performed computationally to generate the reference fragments. In addition, masses of the reference peptide fragments are adjusted as necessary to reflect derivatizations equivalent to those made to the experimental peptides, for example to include the exogenous affinity tag.

The presence of signature peptides in the sample is detected by comparing the masses of the experimentally generated peptides with the masses of signature peptides derived from putative proteolytic cleavage of the set of reference proteins obtained from the database. Software and databases suited to this purpose are readily available either through commercial mass spectrometer software and the Internet. Optionally, the peptide databases can be preselected or reduced in complexity by removing peptides that do not contain the amino acid(s) upon which affinity selection is based.

There will, of course, be instances where peptides cannot be identified from databases or when multiple peptides in the database have the same mass. One approach to this problem is to sequence the peptide in the mass spectrometer by collision induced dissociation. Ideally this is done with a MALDI-MS/MS or ESI-MS/MS instrument. Another way to proceed is to isolate peptides and sequence them by a conventional method. Because the signature peptide strategy is based on chromatographic separation methods, it is generally relatively easy to purify peptides for amino acid sequencing if sufficient material is available. For example, conventional PTH-based sequencing or carboxypeptidase based C-terminal sequencing described for MALDI-MS several years ago (D. Patterson et al., *Anal. Chem.* 67:3971-3978 (1995)). In cases where 6-10 amino acids can be sequenced from the C-terminus of a peptide, it is often possible to synthesize DNA probes that would allow selective amplification of the cDNA complement along with DNA sequencing to arrive at the structure of the protein.

EXAMPLES

The present invention is illustrated by the following examples. It is to be understood that the particular examples, materials, amounts, and procedures are to be interpreted broadly in accordance with the scope and spirit of the invention as set forth herein.

Example 1

Fractionation of Isotopically Labeled Peptides in Quantitative Proteomics

This study examines the extent to which isotopic forms of peptides having the same amino acid sequence are resolved by reversed-phase chromatography and assesses the degree to which resolution of these isotopically different forms of a peptide impact quantification.

Materials and Methods

Materials. Human angiotensin I (Asp-Arg-Val-Tyr-Ile-His-Pro-Phe-His-Leu-OH), HPLC-grade acetonitrile (ACN), N-hydroxysuccinimide, N-acetoxysuccinimide, monobasic sodium phosphate, dibasic sodium phosphate, acetic-$d_6$-anhydride, succinic anhydride, and succinic-$d_4$-anhydride were purchased from Sigma-Aldrich Co. (St. Louis, Mo.). The PepMap C18 4.6 i.d. (internal diameter)×250 mm was purchased from Applied Biosystems (Framingham, Mass.). Double-deionized water (ddI $H_2O$) was produced by a Milli-Q Gradient A10 System from Millipore Co. (Bedford, Mass.). All reagents were used directly without further purification.

Synthesis of N-Acetoxy-$d_3$-succinimide. A solution of 4.0 g (34.8 mmol) of N-hydroxysuccinimide in 11.4 g (105 mmol) of acetic-$d_6$-anhydride was stirred at room temperature. White crystals began to deposit in 10 minutes. After 15 hours the solution was filtered. The crystals were washed with hexane and then dried in a vacuum. The product yield was 5.43 g (100%), mp 133-134° C. (Ji et al., *J. Chromatogr. B* 2000, 745, 197-210).

Acetylation of peptides. A 3-fold molar excess of N-acetoxysuccinimide and N-acetoxy-$d_3$-succinimide was added individually to equal aliquots of 1 mg/mL peptide solution in phosphate buffer at pH 7.5. After 4-5 hours stirring at room temperature, equal aliquots of the two samples were mixed (Ji et al., *J. Chromatogr. B* 2000, 745, 197-210).

Isotopic labeling of peptides by succinic anhydride and succinic-$d_4$-anhydride. A 50-fold molar excess of succinic anhydride and succinic-$d_4$-anhydride was added individually to experimental and control samples in phosphate buffer, pH 7-8. Labeling reagent was added in small aliquots over the course of the first hour, and the reaction was allowed to proceed for another 2 hours. N-Hydroxylamine was then added in excess, and the pH was adjusted to 11-12. Incubation with hydroxylamine was allowed to proceed for 10 minutes. The function of the hydroxylamine reaction was to hydrolyze esters that might have been formed during the acylation reaction.

Reversed-phase elution of isotopically labeled peptides. Isotopically labeled peptide mixtures were separated by gradient elution from a 4.6 i.d.×250 mm PepMap C18 silica column on an Integral Micro-Analytical Workstation (Applied Biosystems, Framingham, Mass.). The PepMap C18 column was equilibrated using 95% mobile phase A (0.1% TFA in ddI $H_2O$) and 5% mobile phase B (95% ACN/0.1% TFA in ddI $H_2O$) at a flow rate of 1.00 mL/min for 3 column volumes (CV). A 100-µL portion of the isotopically labeled peptides was injected automatically and gradient elution of the analyte was achieved using 100% mobile phase A to 100% mobile phase B over 60 minutes at a flow rate of 1.00 mL/min. The gradient was then held at 100% mobile phase B for an additional 5 minutes. Throughout the analysis, an on-line UV detector set at 214 nm was used to monitor isotopic separation of the peptide mixture. The peptides were simultaneously monitored by ESI-MS directly coupled to the LC.

ESI-MS analysis. Mass spectral analyses were performed using a Mariner Biospectrometry Workstation (Applied Biosystems, Framingham, Mass.) equipped with an atmospheric pressure ESI source. All spectra were obtained in the positive ion mode at a sampling rate of 1 spectrum every 3 seconds. During the coupled ESI-MS acquisition, masses were scanned from m/z 500 to 3000 at 140 V nozzle potential. The instrument was tuned and mass calibrated by manual injection of Mariner calibration mixture (Applied Biosystems, Framingham, Mass.) at 3.0 µL/min. Extracted ion chromatograms were used to reconstruct elution profiles of deuterated and nondeuterated peptides separately.

Results and Discussion

The goals of this study were to (1) assess the extent to which resolution of internal standards and analytes would impact quantification, (2) develop methods to quantify partial resolution of components in nonsymmetrical chromatographic peaks, and (3) examine experimentally the degree to which resolution of several isotopically labeled species occurred.

Theoretical assessment of isotopic fractionation. Simulations were used to examine the influence of isotopic fractionation on abundance ratio quantification. In the simulation below, deuterated and nondeuterated peptide chromatographic peaks were assumed to have a Gaussian shape. Deuterated compounds usually elute earlier than their nondeuterated counterparts in reversed-phase liquid chromatography. Assuming Gaussian peak shape, the elution profile of the deuterated peptide peak can be described by the equation $$f(t) = \frac{1}{\sigma\sqrt{2\pi}} e^{\frac{1t^2}{2\sigma^2}} \quad (1)$$

but that of the nondeuterated peptide peak would be $$f(t-\Delta) = \frac{1}{\sigma\sqrt{2\pi}} e^{\frac{1}{2}\frac{(t-\Delta)^2}{\sigma^2}} \quad (2)$$

where t is time relative to the center of the deuterated peptide peak, f(t) is peak intensity of the deuterated peptide at time t, f(t−Δ) is peak intensity of the nondeuterated peptide at time t, Δ is the separation between the deuterated and nondeuterated peptide peaks (which was positive in all cases studied), σ is standard deviation and is equal to $W_{1/2}/2.355$ for Gaussian peaks, and $W_{1/2}$ is the full peak width at half-maximum of a Gaussian peak. When resolution (R) between these two compounds is expressed as $$R = \frac{\Delta}{W_{1/2}} = \frac{\Delta}{2.355\sigma} \quad (3)$$

the observed abundance ratio (ratio$_{obs}$, nondeuterated peptide vs deuterated peptide, i.e., H/D) at any point in the elution profile of the two analytes will be given by the equation $$\text{ratio}_{obs} = \text{ratio}_{true} \frac{f(t-\Delta)}{f(t)} = \text{ratio}_{true} e^{\frac{\Delta}{2\sigma^2}(2t-\Delta)} \quad (4)$$

$$= \text{ratio}_{true} e^{2.355R\frac{1}{\sigma} - 2.773R^2}$$

where ratio$_{true}$ is the abundance ratio in the sample before chromatography. Following rearrangement and substitution of terms, equation 4 becomes $$\ln(\text{ratio}_{obs}) = \frac{2.355R}{\sigma} t + (\ln \text{ratio}_{true} - 2.773R^2) \quad (5)$$

and $$R = \text{slope}\frac{\sigma}{2.355\text{ratio}_{true}} = \frac{(\text{slope})(W_{1/2})}{5.546} \quad (6)$$

Eqs. 5 and 6 suggest that a plot of ln(ratio$_{obs}$) vs. t will be linear and the slope could be used to calculate R when peak asymmetry is small. Plots of experimental data using this model will be referred to as a Gaussian model log plot.

Using a Taylor series expansion when R and |t| are small, $$\text{ratio}_{obs} \approx \text{ratio}_{true}\left(1 + 2.355R\frac{t}{\sigma} - 2.773R^2\right) \quad (7)$$

$$= \frac{2.355R\text{ratio}_{true}}{\sigma} t +$$

$$(\text{ratio}_{true} - 2.773\text{ratio}_{true}R^2)$$

and $$R = \text{slope}\frac{\sigma}{2.355\text{ratio}_{true}} = \frac{(\text{slope})(W_{1/2})}{5.546\text{ratio}_{true}} \quad (8)$$

According to Eqs. 7 and 8, a plot of ratio$_{obs}$ vs t will be linear at the center of the peak (±1σ), and the slope of the straight line obtained could be used to calculate R when R and peak asymmetry are small. Plots derived using this model will be designated as a Gaussian model linear plot.

Figure 1:
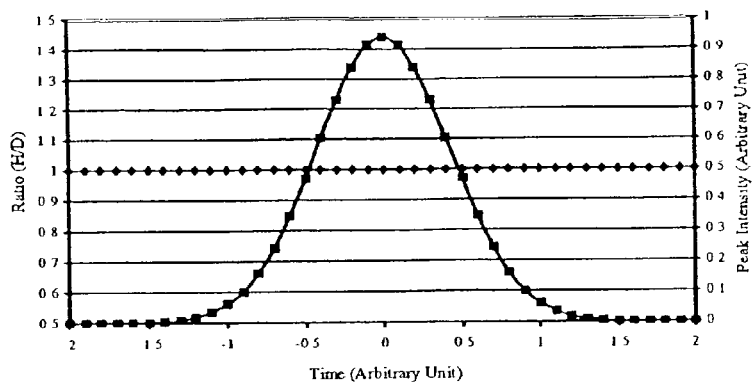
FIG. 1 depicts a simulation based on Eqs. 4 and 7 of abundance ratio (◆) as a function of elution time in a chromatographic separation of isotopically labeled peptides when ratio$_{true}$=1. (a) when R=0, ratio$_{obs}$ (◆) does not vary with time and always equals ratio$_{true}$; (b) assuming that R=0.025, the deuterated peptide (●) elutes first, and the full peak width at half-maximum ($W_{1/2}$) of the peak is 60 seconds, the deuterated peptide (●) would elute 1.5 seconds faster than the nondeuterated peptide (■), and ratio$_{obs}$ (◆) would vary continuously across the peak. Eq. 7 approximates the ratio$_{obs}$ well at the center of the peak when R is small (▲); (c) assuming that R=0.5, the deuterated peptide (●) elutes first and the full peak width at half-maximum ($W_{1/2}$) of the peak is 60 seconds, the deuterated peptide (●) would elute 30 seconds faster than the nondeuterated peptide (■), and ratio$_{obs}$ (◆) would vary continuously across the peak.
Figure 1:
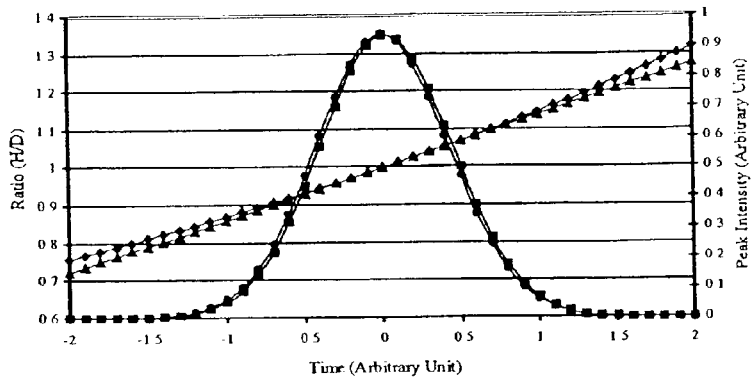
Figure 1:
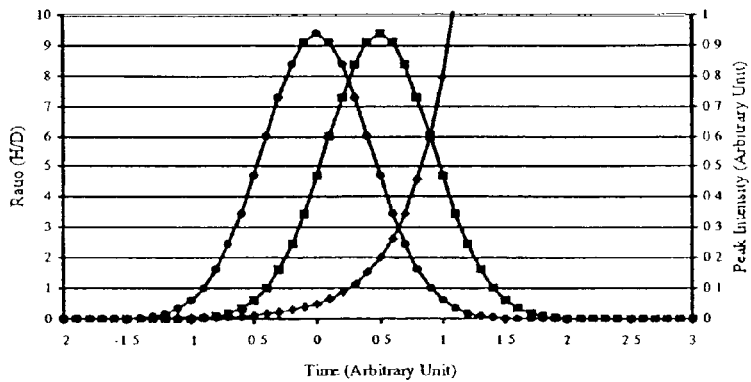
Figure 2:
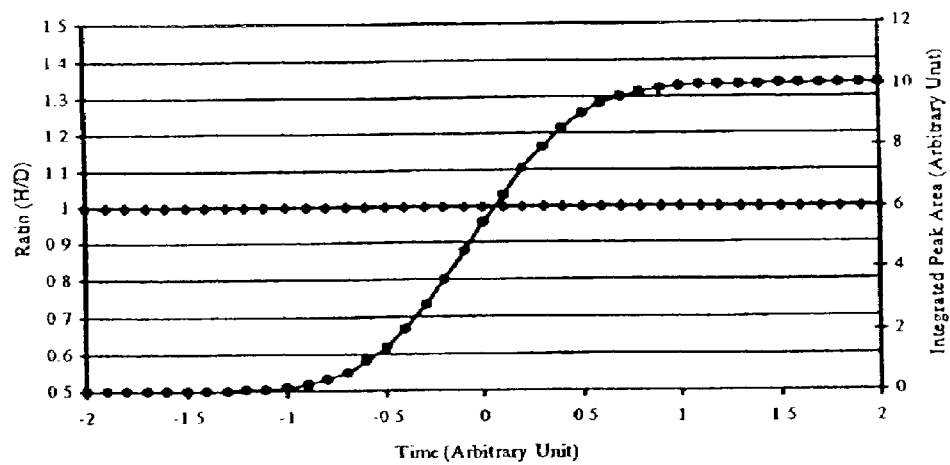
FIG. 2 depicts a simulation of isotopic fractionation of deuterated (●) and nondeuterated (■) peptides in reversed-phase chromatography, ratio$_{true}$=1. (a) deuterated and nondeuterated peptides elute at exactly the same time, that is, R=0. Ratio$_{obs}$ (◆) does not vary with time and always equals ratio$_{true}$; (b) R=0.1, ratio$_{obs}$ (◆) increases with time and eventually levels off to give ratio$_{true}$.
Figure 2:
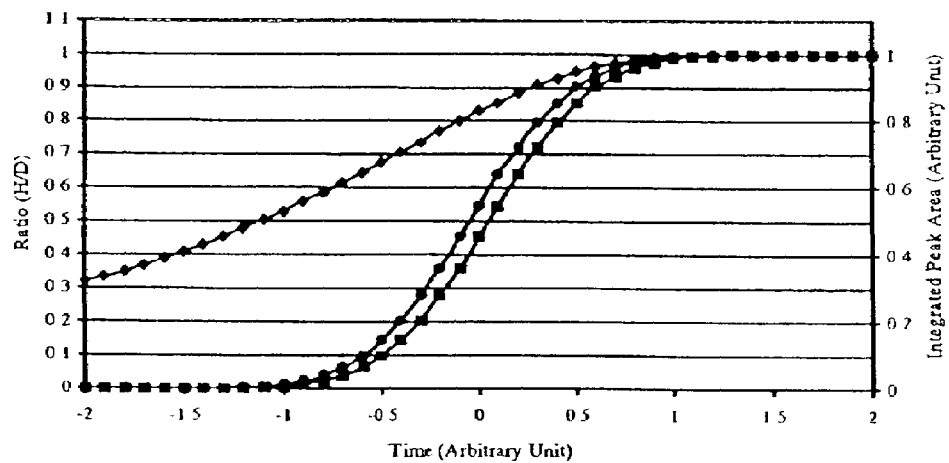
Figure 3:
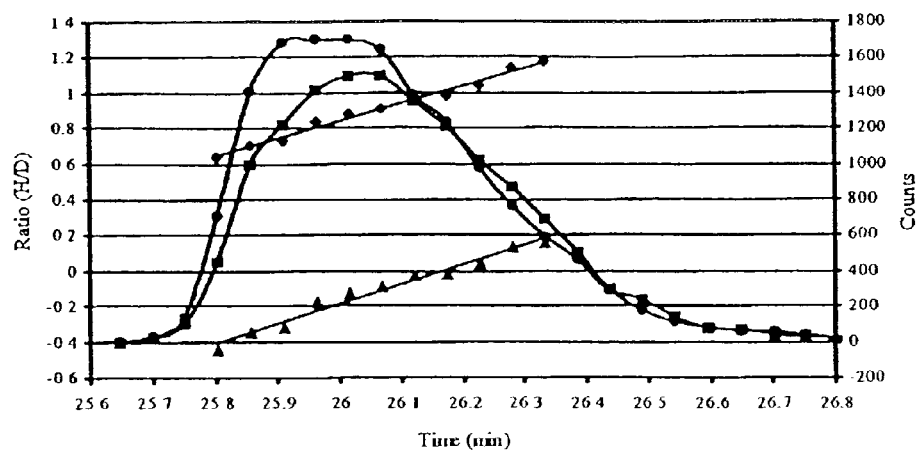
FIG. 3 depicts extracted ion chromatograms of angiotensin I labeled by succinic anhydride and succinic-$d_4$-anhydride. Four deuterium atoms were incorporated in the deuterated peptide. (a) deuterated peptide (●) eluted faster than the nondeuterated peptide (■). Ratio$_{obs}$ (◆) increased from 0.64 at 25.80 minutes to 1.17 at 26.33 minutes, while ratio$_{true}$ equaled 0.90. Both ratio$_{obs}$ (◆) vs. time and ln(ratio$_{obs}$) (▲) vs time were linear ($R^2$ equaled 0.98 and 0.97, respectively), because the peak asymmetry was small. Both R's calculated from the slopes equaled 0.088 (Eqs. 6 and 8); (b) plotting integrated peak area vs time, ratio$_{obs}$ (◆) increased with time (i.e., 0.70 at 25.91 minutes) and eventually leveled off to give ratio$_{true}$ (i.e., 0.90); (c) curve of the dueterated peptide (●) was normalized (multiplied by ratio$_{true}$) and horizontally shifted toward the right by 1.94 seconds to make the curves of deuterated (■) and nondeuterated (●) peptides coincide.
Figure 3:
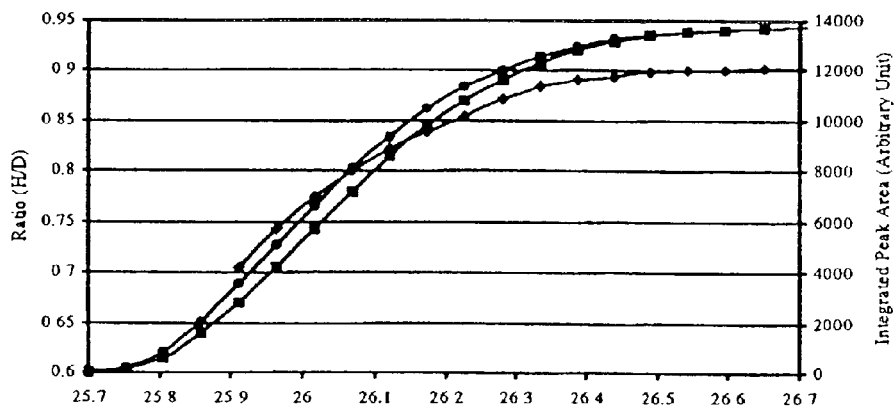
Figure 3:
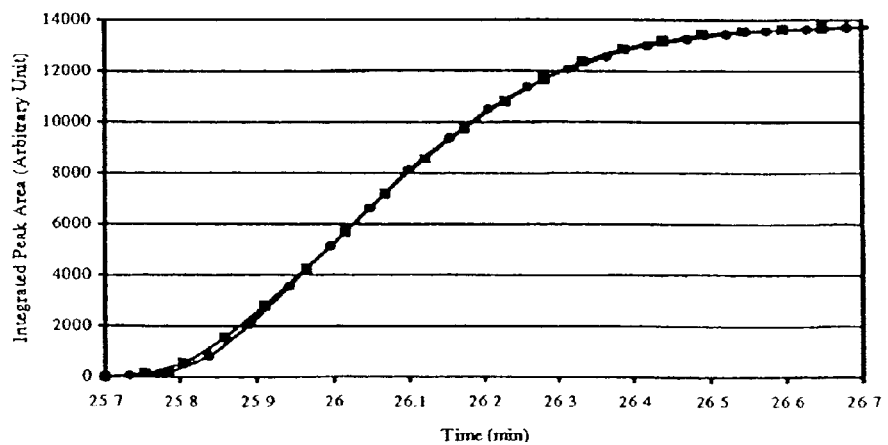
Figure 4:
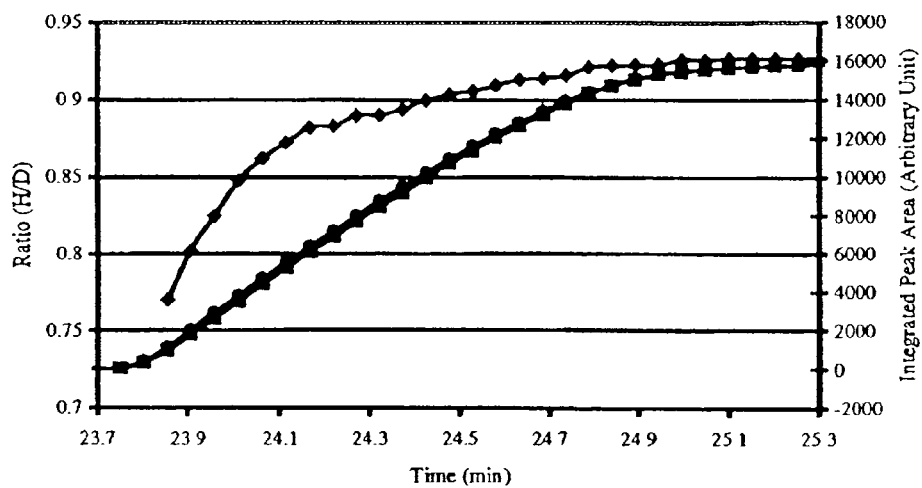
FIG. 4 depicts extracted ion chromatograms of angiotensin I labeled by CH$_3$CO- and CD$_3$CO-groups. (a) only the NH$_2$ group at the N-terminus of the peptide was acetylated. Three deuterium atoms were incorporated into the deuterated peptide. The deuterated peptide (●) eluted 1.31 seconds faster than the nondeuterated (■) peptide. Ratio$_{obs}$ (◆) increased with time (i.e., 0.76 at 23.80 minutes) and eventually leveled off to give ratio$_{true}$ (i.e., 0.93); (b) both the NH$_2$ group at the N-terminus of the peptide and the OH group of tyrosine were acetylated. Six deuterium atoms were incorporated into the deuterated peptide. The deuterated peptide (●) eluted 3.75 seconds faster than the nondeuterated peptide (■). Ratio$_{obs}$ (◆) increased with time (i.e., 0.33 at 25.57 minutes) and eventually leveled off to give ratio$_{true}$ (i.e., 0.50).
Figure 4:
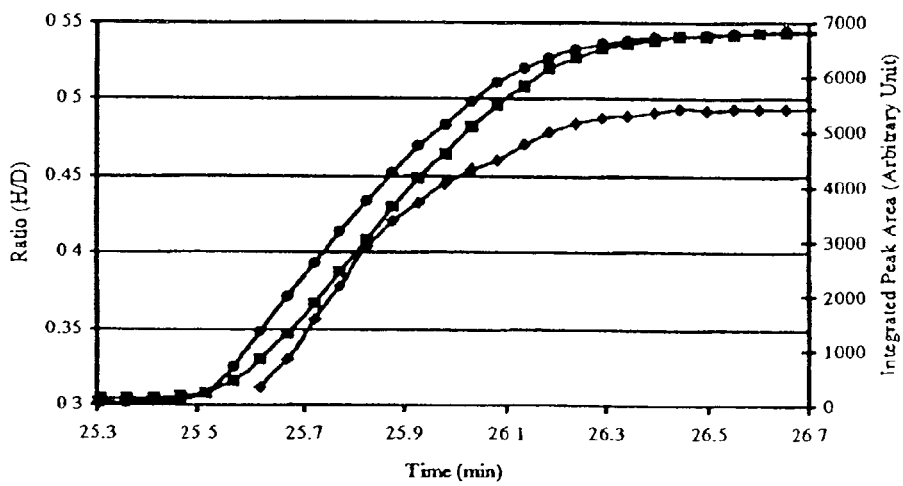
Figure 5:
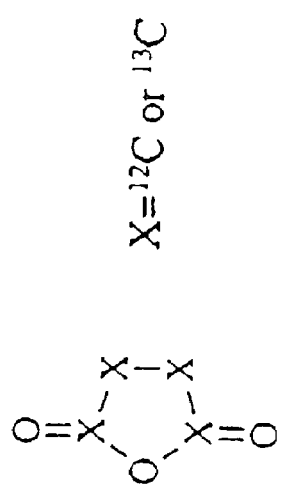
FIG. 5 depicts structures of derivatization agents (a) succinic anhydride-$^{13}C_0$ and $^{13}C_4$; (b) ICAT-$^2H_0$ and $^2H_8$.
Figure 5:
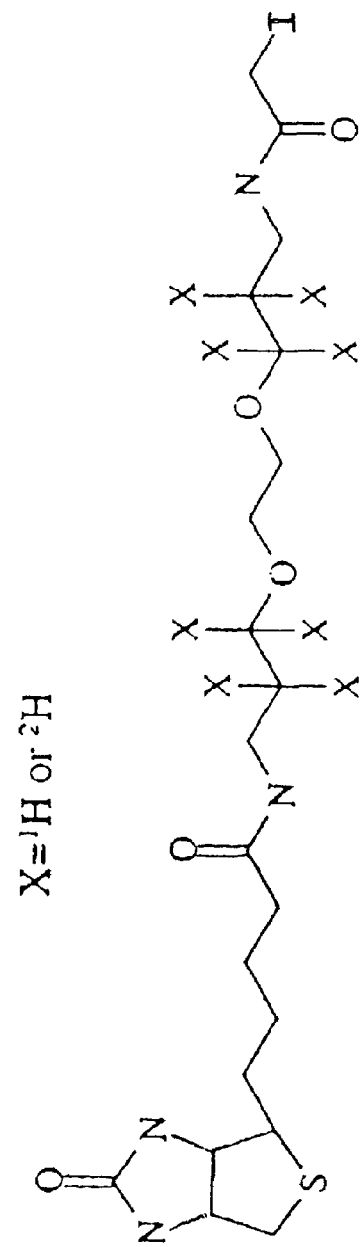
Figure 1A:
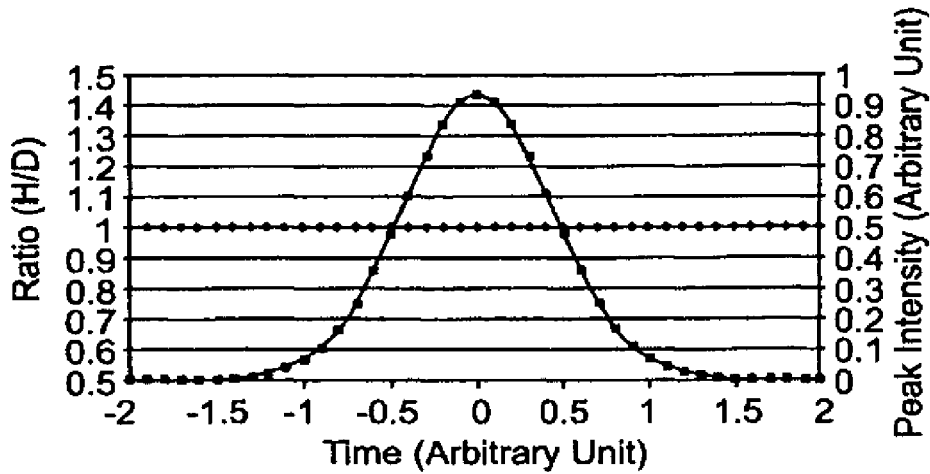
Figure 1B:
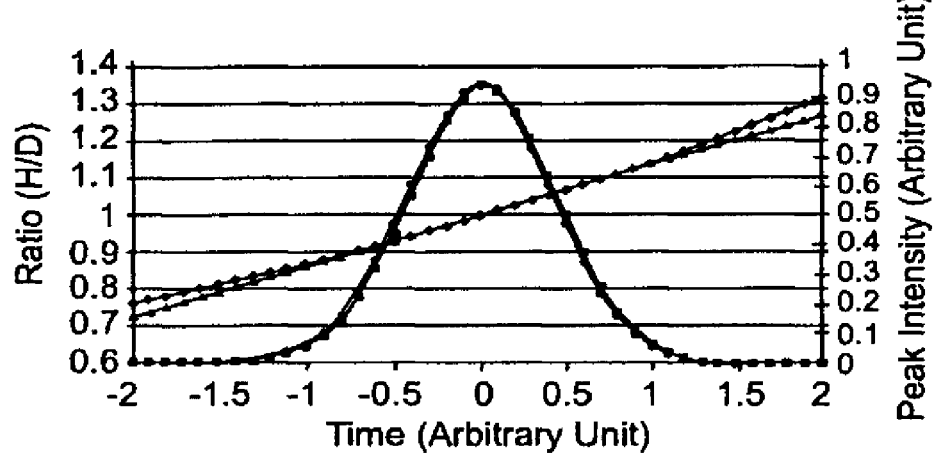

Simulation of the elution of two substances from a chromatography column as Gaussian curves is seen in FIG. 1. Ratio$_{obs}$ is constant with time and always equals ratio$_{true}$ when R=0 (FIG. 1A). Assuming that R=0.025 and 0.5, the deuterated peptide elutes first, and the full peak width at half-maximum ($W_{1/2}$) of the peak is 60 seconds, the deuterated peptide would elute 1.5 and 30 seconds faster than the nondeuterated peptide and ratio$_{obs}$ would vary continuously across the peak (FIG. 1B, C). This leads to a substantial error in determining the abundance ratio in a sample when quantification measurements are made at the peak extremes. It is seen in Table 1 that a measurement made at ±1σ would deviate by −83 and +500% from the abundance ratio in the original sample (ratio$_{true}$) when R=0.5. The error would be even greater at larger values of σ.

TABLE 1

Examples of Systematic Quantification Errors Resulting from Fractionation of Isotopically Labeled Peptides

| measurement point | R | ratio$_{obs}$ | ratio$_{true}$ | error % |
|---|---|---|---|---|
| t = −1σ | 0.025 | 0.94 | 1.0 | −6% |
|  | 0.5 | 0.17 | 1.0 | −83% |
| t = +1σ | 0.025 | 1.06 | 1.0 | +6% |
|  | 0.5 | 6.0 | 1.0 | +500% |
| t = 0 (center of peak) | 0.025 | 1.0 | 1.0 | 0 |
|  | 0.5 | 1.0 | 1.0 | 0 |
| integration of first half of the peak | 0.025 | 0.96 | 1.0 | −4% |
|  | 0.5 | 0.39 | 1.0 | −61% |
| integration of second half of the peak | 0.025 | 1.04 | 1.0 | +4% |
|  | 0.5 | 2.6 | 1.0 | +160% |
| integration across the whole peak | 0.025 | 1.0 | 1.0 | 0 |
|  | 0.5 | 1.0 | 1.0 | 0 |

Figure 1C:
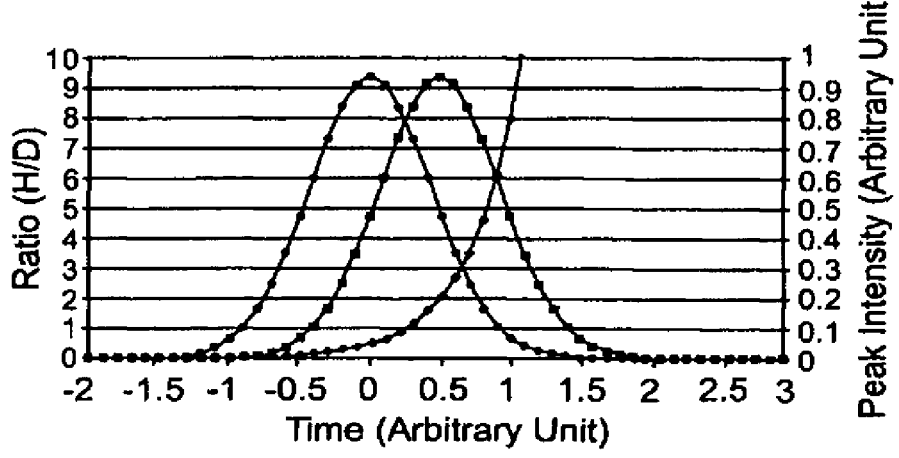

There is the possibility that only a portion of a peak will be collected and sent into subsequent dimensions of analysis, because multidimensional separations are used in proteomics. Assuming that only half of the peak was sent into a second chromatographic dimension in the case described in FIG. 1C, the leading edge of the peak would have 44% more of the deuterated species and the trailing edge 44% less than that found in the original sample (Table 1). The opposite is true for the nondeuterated species. Table 1 also shows that accurate ratio measurements may be made either at the center of the peak or by integrating the whole peak. Unfortunately, these options are not always available.

There are many cases in which partial resolution of isotopically labeled peptides might be a problem. The multidimensional chromatography case has been noted above. Similar problems would arise with the collection of fractions across a chromatographic peak (FIG. 1B, C) for analysis by matrix assisted laser desorption ionization mass spectrometry (MALDI-MS). The abundance ratio in fractions collected at large σ values would deviate substantially from the "true" ratio in the sample. Another potential problem is that matrix components eluting with the analyte at leading and trailing edges of peaks can be very different. This introduces the potential for differences in ionization efficiency across a peak. In this case, integration of the whole peak or taking measurements at the center of the peak to achieve accurate ratio measurement becomes invalid.

Table 2 presents another view of the problem. Assuming R=0.5 and the ratio measurement is made at ±1σ from the center of the peak, it is seen in Table 2 that there is little difference between the $ratio_{obs}$ value of 0.18 at +1σ from a sample in which $ratio_{true}$ is 0.1 and the $ratio_{obs}$ value of 0.17 at −1σ from a sample in which $ratio_{true}$ is 1.0. A similar problem is seen in differentiating between the $ratio_{obs}$ values of 1.0 and 10 at their respective time of +1σ and −1σ. When R is larger or ratio measurements are made further away from the center of the peak, the problem is even more serious!

TABLE 2

Systematic Errors Caused by Fractionation of the Deuterated and Nondeuterated Peptides in Reversed-Phase Chromatography, R = 0.5

| $ratio_{true}$ | $ratio_{obs}$ | |
| --- | --- | --- |
| | −1σ | +1σ |
| 1:10 (down-regulated) | 0.017 | 0.18 |
| 1:1 (no change) | 0.17 | 6.0 |
| 10:1 (up-regulated) | 5.8 | 60 |

Figure 2A:
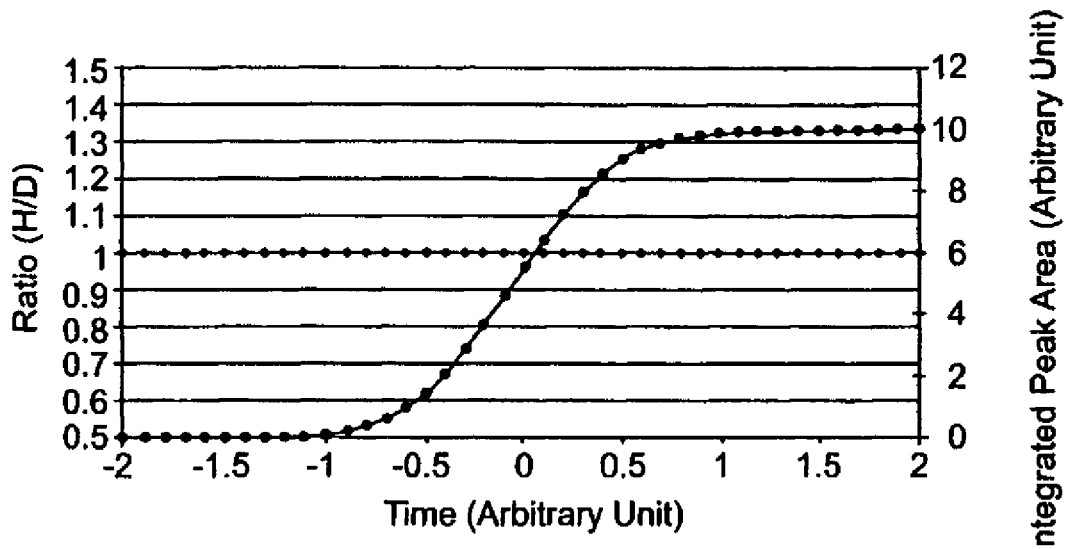

Calculation of R. It has been seen in FIG. 1 that even small differences in R can have a substantial impact on abundance ratio determinations. Unfortunately, chromatography peaks are frequently not Gaussian, and Eqs. 6 and 8 will not predict R with the accuracy needed to evaluate small differences in R. Although Gaussian models still provide good estimations, a more general method is needed to evaluate resolution (R). The Δ tuning method described below allows evaluation of R with peaks of any shape. Assuming that deuterated and nondeuterated peptides have the same peak shape and plotting integrated peak area against time, $ratio_{obs}$ is redefined as the integrated peak area of the nonduterated peptide over that of deuterated peptide (H/D) at time t in this model. When R=0, $ratio_{obs}$ obviously does not vary with time (FIG. 2A).

Figure 2B:
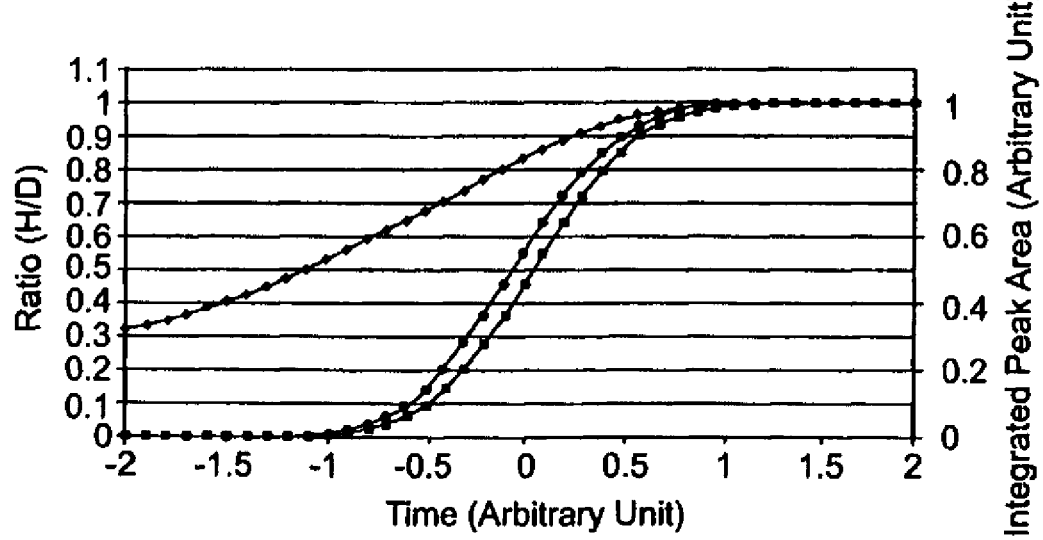

When the deuterated peptide is partially resolved from the nondeuterated peptide, $ratio_{obs}$ increases with elution time and eventually reaches a plateau at $ratio_{obs}$ (FIG. 2B). Assuming that the two elution curves are of the same shape, they may be brought to overlap if the elution curve of the deuterated peptide is normalized (i.e., multiplied by $ratio_{true}$) and shifted in time until the two curves coincide. The shifting in time, or Δ tuning, required to cause overlap is given by the expression $$\Delta = R \ast W_{1/2} \quad (9)$$

Retention times of the deuterated peptide ($t_D$) and nondeuterated peptide ($t_H$) can be measured directly from the extracted ion chromatograms produced by an electrospray ionization (ESI) mass spectrometer, and R can be calculated using the equation $$R = \frac{t_H - t_D}{W_{1/2}} \quad (10)$$

when R is large.

Table 3 summarizes the options for calculating R in four different cases. It is seen that the Δ tuning method is the most general, applying to all four cases.

TABLE 3

Calculation of Resolution (R) in Different Situations

| | R | peak asymmetry | methods apply |
| --- | --- | --- | --- |
| case I | small | small | Gaussian model linear plot; Gaussian model log plot; Δ tuning; |
| case II | small | large | Δ tuning; |
| case III | large | small | $t_H$-$t_D$; Gaussian model log plot; Δ tuning; |
| case IV | large | large | $t_H$-$t_D$; Δ tuning; |

Comparison of R values from three different labeling reagents. R values from three different labeling reagents, succinic anhydride ($d_0$ and $d_4$), N-acetoxysuccinimide ($d_0$ and $d_3$), and an isotope-coded affinity tag (i.e., ICAT, $d_0$ and $d_8$) (Parker et al., 48th ASMS Conference on Mass Spectrometry and Allied Topics, 2000) were determined using the methods in Table 3.

Figure 3A:
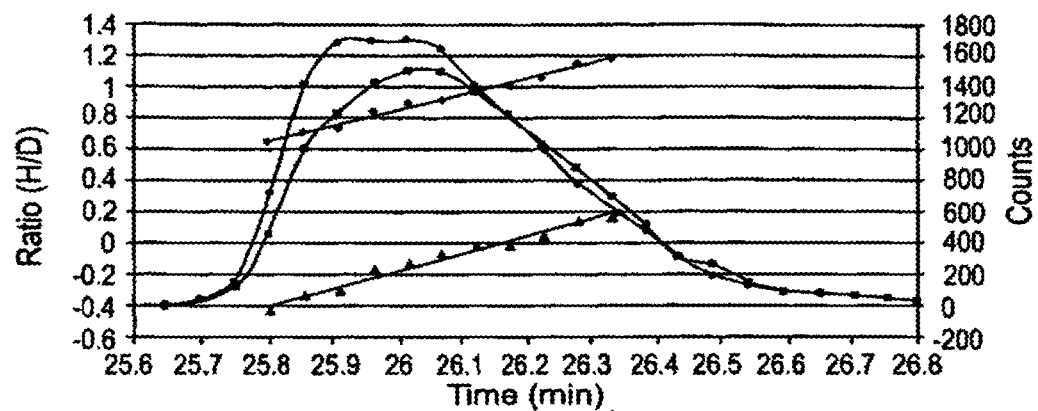
Figure 3B:
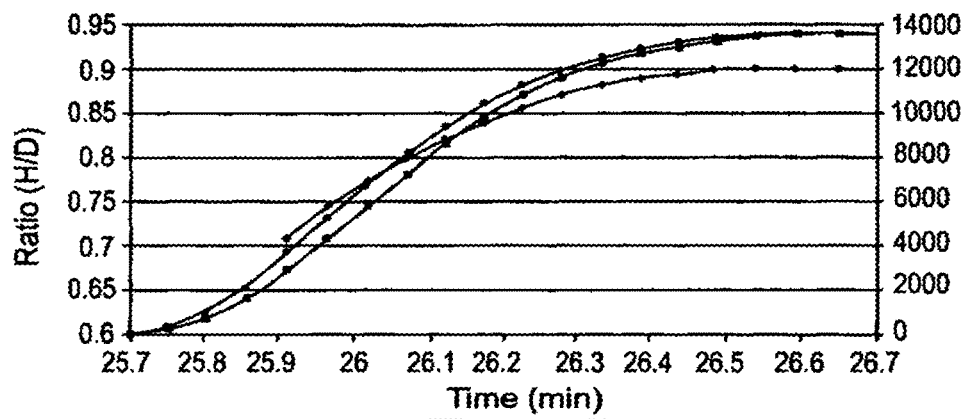
Figure 3C:
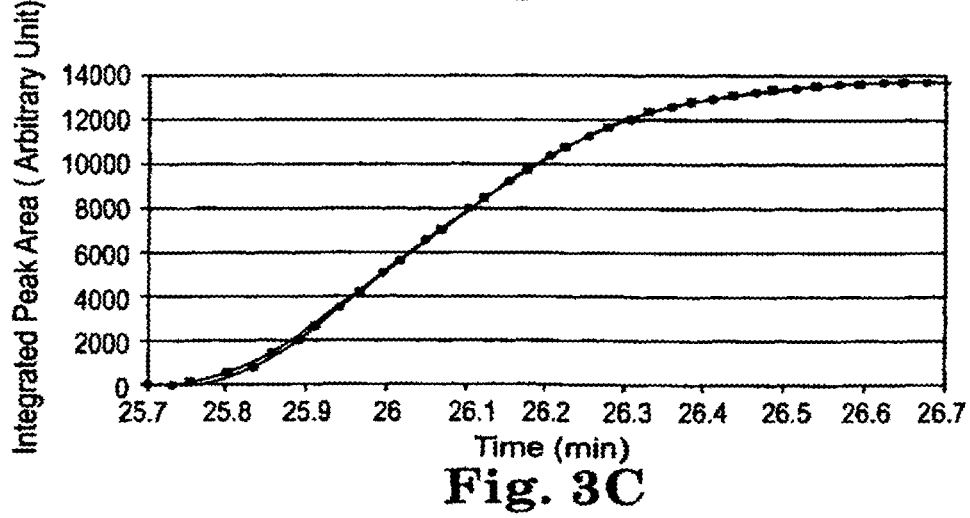

Angiotensin I samples were labeled with succinic anhydride and succinic-$d_4$-anhydride and mixed. Peak asymmetry was small, and the plots of $ratio_{obs}$ vs time and $\ln(ratio_{obs})$ vs. time showed good linearity in FIG. 3A. Calculation of R based on the Gaussian model linear plot and Gaussian model log plot both equal 0.088 (Eqs. 6 and 8). The Δ tuning method was applied in FIG. 3B, C. It was necessary to shift the elution curve of the deuterated peptide 1.94 seconds to the right to make the two curves coincide. The R value based on the Δ tuning method was 0.073, close to the R values obtained with the Gaussian model linear plot and Gaussian model log plot (i.e., 0.088).

At low peptide concentration, the peak intensity plot was found to be very noisy, and the integrated peak area plot greatly improved accuracy and precision of the R measurement. In addition, because Δ tuning is based on only one assumption that deuterated and nondeuterated peptides have the same peak shape, the method will be generally applicable to the determination of R values.

Figure 4A:
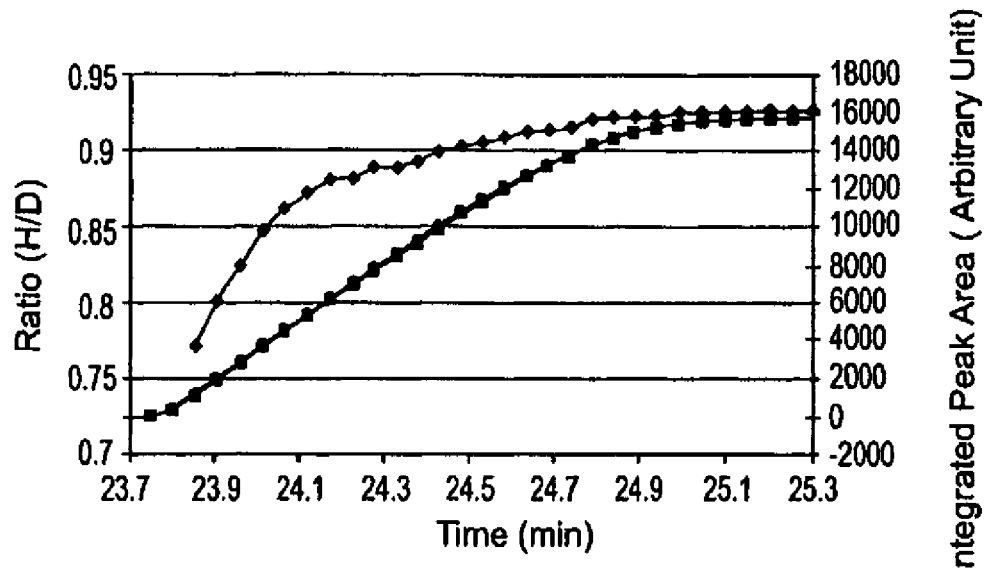
Figure 4B:
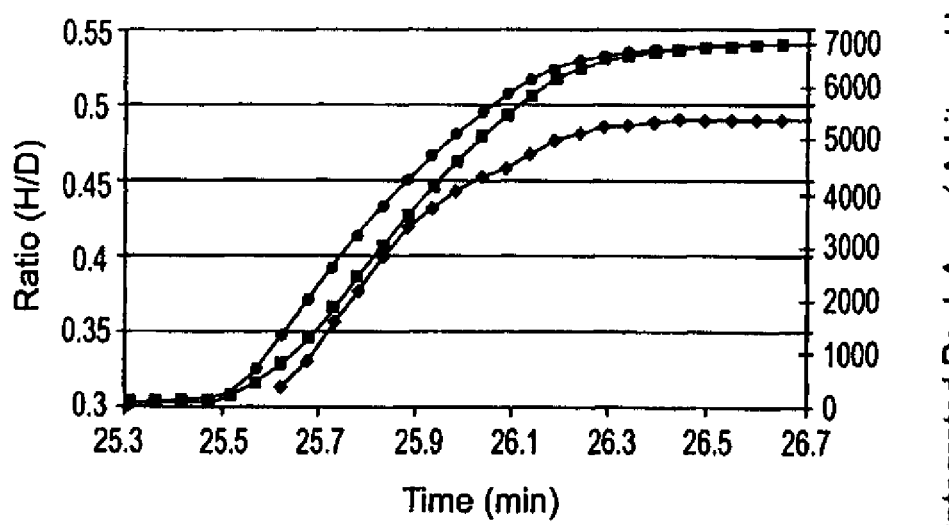

Angiotensin I was also labeled with $CH_3CO$- and $CD_3CO$- groups. The sample was intentionally over-derivatized to produce an analyte with a single acetate group (FIG. 4A) and another with two acetate groups (FIG. 4B). R values calculated using the Δ tuning method were 0.023 and 0.11, respectively. A resolution of 0.023 is roughly equivalent to that seen in FIG. 1B. The large increase of R when six deuterium atoms were incorporated, as compared to three, could result from the fact that the second acetylation was on tyrosine. Tyrosine is hydrophobic and interacts heavily with the stationary phase in reversed-phase chromatography.

In the literature, ICAT $d_0$- and $d_8$-labeled peptides were shown to be separated (Parker et al., 48th ASMS Conference on Mass Spectrometry and Allied Topics, 2000). $Ratio_{obs}$ kept increasing across the peak. R was estimated to be 0.45 on the basis of both the $t_H$-$t_D$ and Gaussian model log plot methods. It was assumed that the deuterated peptide and nondeuterated peptide reached their peak maxima at spectrum numbers 390 and 400, respectively (Table 4). A resolution of 0.45 is roughly equivalent to that seen in FIG. 1C.

TABLE 4

Ratio$_{obs}$ in Selected Spectra of ICAT-d$_0$ and d$_8$ Labeled Peptide
(Adapted from Parker et al., 48th ASMS Conference on
Mass Spectrometry and Allied Topics, 2000).

| spectrum # | d$_0$ mass | intensity | d$_8$ mass | intensity | ratio (H/D) |
|---|---|---|---|---|---|
| 390 | 592.2802 | 5385 | 594.9623 | 9953 | 0.54 |
| 400 | 592.2808 | 10066 | 594.9619 | 6370 | 1.6 |
| 410 | 592.2802 | 3896 | 594.9616 | 1011 | 3.8 |

R values under different conditions for all of the labeling reagents studied are summarized in Table 5. It is obvious that R varies substantially with different labeling reagents and the number of deuterium atoms incorporated.

TABLE 5

Comparison of R under Different Conditions*

| | succinic anhydride | N-acetoxysuccinimide | ICAT | |
|---|---|---|---|---|
| no. $^2$H atoms incorporated | 4 | 3 | 6 | 8 |
| R | 0.073 | 0.023 | 0.11 | 0.45 |

*Data from all three labeling agents were derived under slightly different chromatographic conditions. The extent to which this impacts resolution of isotopic isoforms is unknown.

Significance of fractionation of isotopically labeled peptides in quantitative proteomics. Suppression of ionization between peptides has been noted in ESI-MS when total peptide concentration is high, as when one peptide is eluting in a large background of another. This means that ionization efficiency can vary across a chromatographic peak. Similar problems are seen in MALDI-MS in which matrix peptides have a large impact on suppression. The whole chromatographic peak may not be in the fraction being examined, because samples for MALDI-MS are obtained by fraction collection. As the deuterated and nondeuterated peptides separate from each other, they are ionized at different times and in different matrixes. They effectively become external standards instead of internal standards. This has the potential to produce both significant systematic errors and much greater random errors. In addition, as the elution time becomes longer, the danger of overlapping with other peptides with similar mass increases.

There are other important reasons to minimize R. It is very difficult to do MS/MS analyses on every peptide as it elutes from a chromatography column, particularly when sample fractions contain 10-50 peptides. When the objective is to analyze only a small percentage of peptides that are up- or down-regulated, rapid quantification of changes in concentration based on a single mass spectrum would allow near real-time decisions of whether to execute an MS/MS analysis of a peptide. To accomplish this, ratio$_{true}$ must be determined accurately as early as possible so that the up- or down-regulated peptides can be analyzed by MS/MS during elution of the rest of the peak. This is impossible when ratio$_{obs}$ varies with time. This would mean that the LC-MS analysis has to be done twice on each sample. The first time would be for abundance ratio analysis and the second, for MS/MS on selected peptides. Appropriate stable isotope labeling reagents are desired to make R minimal so that ratio$_{obs}$ stays constant or varies insignificantly with time.

Conclusions

It has been demonstrated both theoretically and experimentally that the chromatographic fractionation of deuterated and nondeuterated peptides could cause substantial systematic errors in quantitative proteomics.

The data were examined in four different ways. The most generally useful treatment of the data was the one in which extracted ion elution data was integrated and resolution was assessed by the time shift required to cause the curves from isotopically different forms of a peptide to coincide (i.e., Δ tuning).

Acetylated peptides showed the lowest degree of separation. Resolution of the deuterated and nondeuterated forms in this case was 0.023. In contrast, resolution of the deuterated and nondeuterated forms of the ICAT reagent were calculated to be 0.45. The deuterium content of the labeling reagent appears to play a major role. Deuterium content should be minimized to reduce isotopic fractionation problems.

Example 2

Minimizing Chromatographic Resolution Using $^{13}$C/$^{12}$C-Coded Peptide Isoforms This experiment was conducted to determine the magnitude of the isotope effect with a commercial deuterated coding agent and to assess the degree to which isotope effects can be minimized with a $^{13}$C labeled derivatizing agent.

Materials and Methods

Materials. Bovine serum albumin (BSA), HPLC grade acetonitrile (ACN), succinic anhydride, acetyl chloride, phosphorus pentoxide, dithiothreitol (DTT), iodoacetic acid (IAA), urea, tris(hydroxymethy)aminomethane (Tris base), tris(hydroxymethyl)aminomethane hydrochloride (Tris acid), calcium chloride were purchased from Sigma-Aldrich (St. Louis, Mo.). Trifluoroacetic acid (Sequanal Grade) was obtained from Pierce (Rockford, Ill.). Sequencing grade modified trypsin was purchased from Promega (Madison, Wis.). Butanedioic acid-$_{13}$C$_4$ was supplied by Isotec (Miamisburg, Ohio). The ICAT kit was purchased from Applied Biosystems (Framingham, Mass.). A C18 column (2.1 mm×250 mm) was obtained from Vydac (Hesperia, Calif.). Double deionized water (ddI H$_2$O) was produced by a Milli-Q™ Gradient™ A10 System from Millipore (Bedford, Mass.).

Proteolysis of BSA. BSA (5 mg) was reduced in 1 mL of 0.2 mol/L Tris buffer (pH 8.5) containing 8 M urea and 10 mM DTT. After a 2 hour incubation at 37° C., iodoacetic acid was added to a final concentration of 20 mmol/L and incubated in darkness on ice for 2 more hours. After dilution with 0.2 mol/L Tris buffer to a final urea concentration of 2 M, modified sequencing grade trypsin was added to the sample at a 50/1 BSA to trypsin mass ratio and the solution was incubated for 8 hours at 37° C. Digestion was stopped by freezing the mixture in liquid nitrogen for 10 minutes.

Synthesis of succinic anhydride-$^{13}$C$_4$. 2 g of butanedioic-$^{13}$C$_4$-acid and 5 mL of acetyl chloride were heated under reflux for 1.5 hours. After reaction the clear solution was cooled to room temperature and kept at 0° C. overnight. The crystals formed upon cooling were further purified from dry diethyl ether and dried in vacuo over P$_2$O$_5$.

Derivatization of peptides. A fifty fold molar excess of succinic anhydride and succinic anhydride-$^{13}$C$_4$ were added individually to tryptic peptides from experimental and control samples. The reaction was allowed to proceed for two hours at room temperature. Peptides were also derivatized with ICAT and ICAT-$^2$H$_8$ as described in the instructions of ICAT kit.

Reversed-phase chromatography of isotopically labeled peptides. Isotopically labeled peptide mixtures were separated by gradient elution from a Vydac C18 column (2.1 mm×250 mm) on an Integral Micro-Analytical Workstation (Applied Biosystems, Framingham, Mass.). The C18 column was equilibrated using 100% mobile phase A (0.01% TFA in ddI H$_2$O) at a flow rate of 250 μL/min for 2 column volumes (CV). Isotopically labeled peptide mixtures (2 nmol) were injected and eluted at a flow rate of 250 μL/min in a linear gradient ranging over 60 min from 100% mobile phase A to 60% mobile phase B (95% ACN/0.01% TFA in ddI H$_2$O). At the end of this period a second linear gradient was applied in 10 minutes from 60% B to 100% B at the same flow rate. The gradient was then held at 100% mobile phase B for an additional 10 minutes. Throughout the analysis an on-line UV detector set at 214 nm was used to monitor separation of the peptide mixtures. The peptides were simultaneously monitored by ESI-MS by directing 10% of the flow into the mass spectrometer.

ESI-MS analysis. Mass spectral analyses were performed using a QSTAR workstation (Applied Biosystems, Framingham, Mass.) equipped with an Ionspray source. All spectra were obtained in the positive ion TOF mode at a sampling rate of one spectrum every two seconds. During LC-MS data acquisition, masses were scanned from m/z 300 to 1800.

Results and Discussion

Assessing the impact of heavy isotopes on chromatographic behavior requires quantification of small changes in resolution (R). Moreover, peaks are not always Gaussian and it is important to deal with peak asymmetry in computing resolution. A "Δ Tuning" method is capable of determining resolution in the case of both symmetrical and asymmetric peaks. It was chosen for the studies outlined below for this reason. This method is based on shifting integrated plots of isoform elution profiles until they overlap. Resolution (R) from the shifting in time, or "Δ tuning" required to cause overlap is give by the expression $$R = \frac{\Delta}{W_{1/2}} \quad (11)$$

where Δ is the time shift required to cause the heavy isotope labeled analyte and the non-isotope labeled analyte elution curves to overlap and $W_{1/2}$ is the average of full peak width at half maximum (FWHM) derived from extracted ion chromatograms of the isoforms. Even the peak shapes of the isotopically labeled peptides are sometime very different when resolution is large. In this case "Δ" simply equals the differences in retention times and "$W_{1/2}$" still equals the average peak widths.

The possibility that isotope effects could vary between peptides must also be considered. For example, peptides with multiple derivatizable functional groups would be expected to show larger isotope effects. The location of the derivatizing agent relative to hydrophobic groups in the peptide could also play a role. Rather than select specific peptides to test these hypotheses, a tryptic digest of bovine serum albumin (BSA) was chosen for study.

Figure 5A:
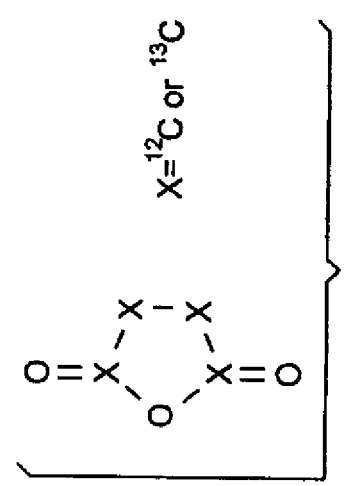
Figure 5B:
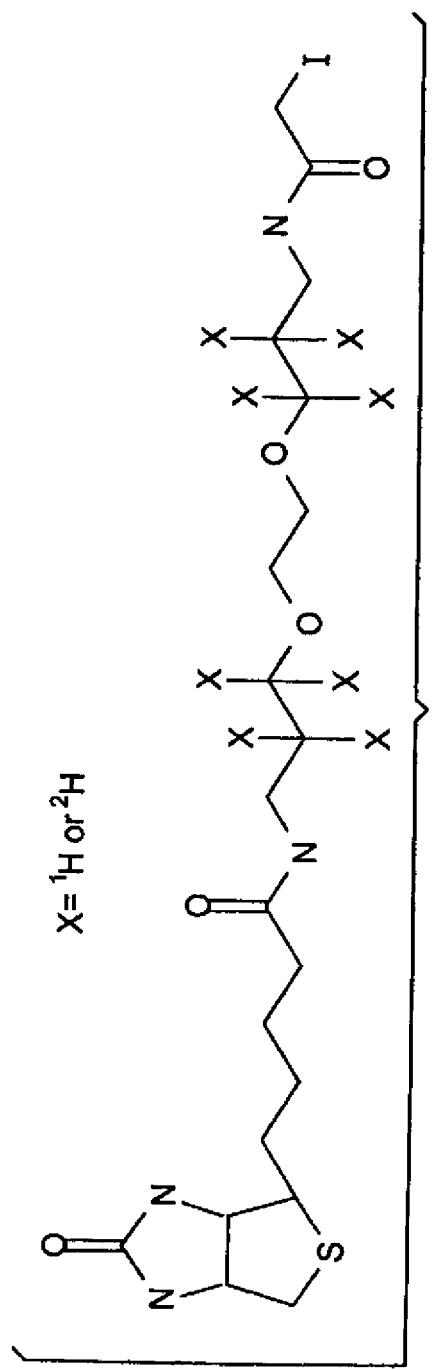

Isotope effects with ICAT. The isotope coded affinity tag (ICAT) reagent is offered commercially for differentially labeling peptides. This reagent is a sulfhydryl directed alkylating agent composed of iodoacetate attached to biotin through a coupling arm. Isotopic isoforms of this reagent are differentially labeled in the coupling arm (FIG. 5A). During the normal course of reducing and alkylating proteins in preparation for proteolysis, the ICAT reagent is used to alkylate cysteine residues in proteins. Subsequent to differential labeling of control and experimental samples with the $^2$H$_0$ and $^2$H$_8$ versions of the ICAT reagent respectively, the samples are mixed and digested with a proteolytic enzyme. Biotinylated, cysteine-containing peptides were selected from digests and the relative concentration of the isotopic isoforms of peptides quantified by mass spectrometry. Approximately 10-20% of all peptides derived from the proteome of eukaryotes contain one or more cysteine residues. This means that the ICAT reagent can only be used to quantify changes in a proteome that involve cysteine-containing peptides.

Figure 6A:
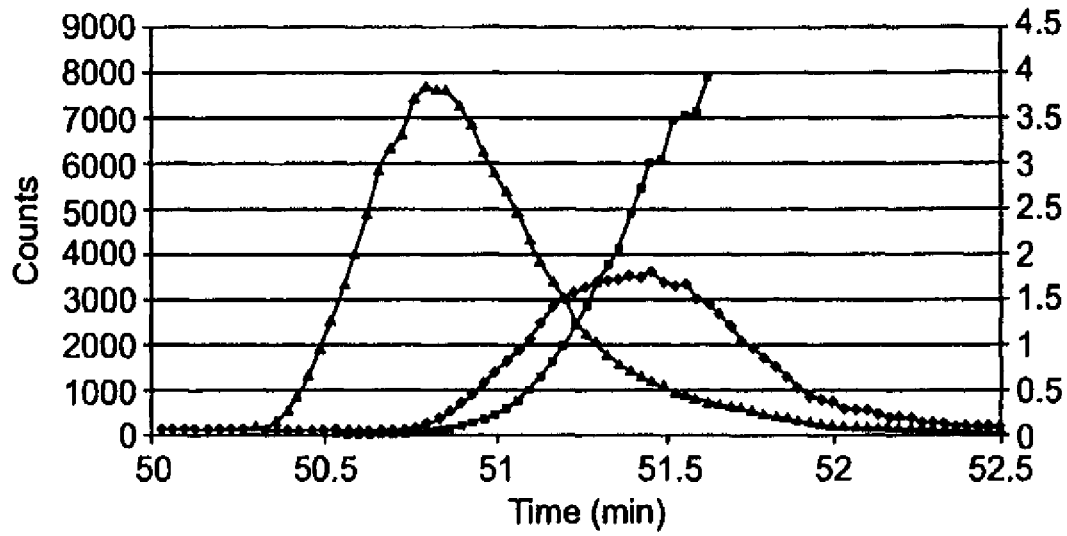
Figure 6B:
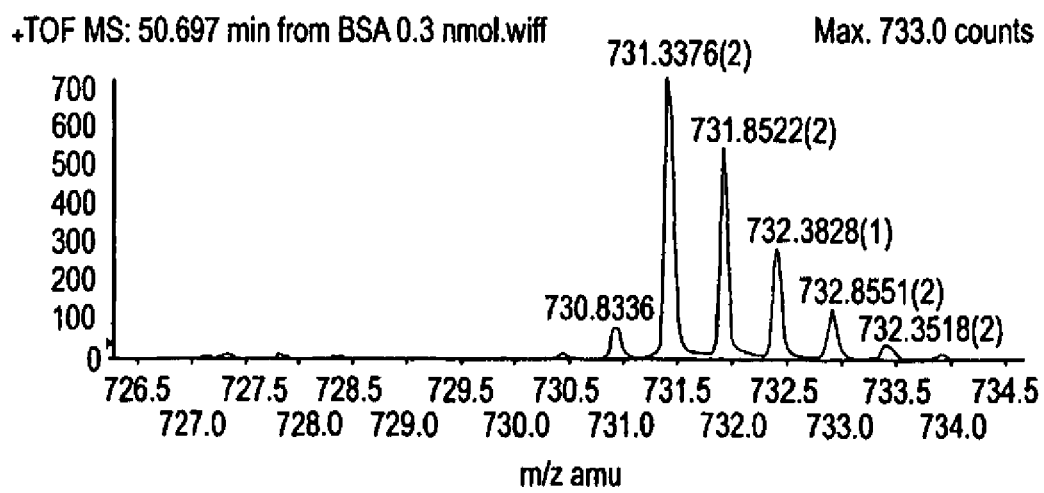
Figure 6C:
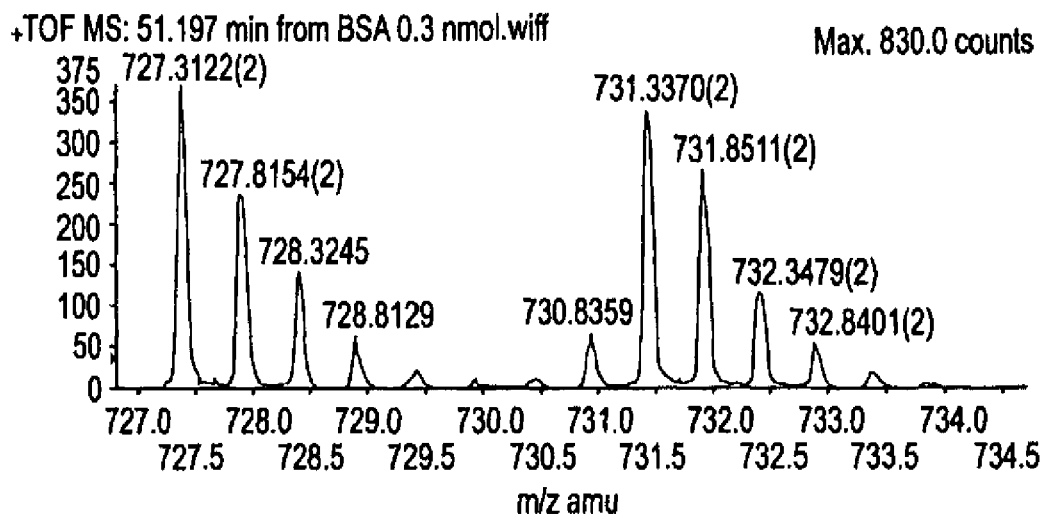
Figure 6D:
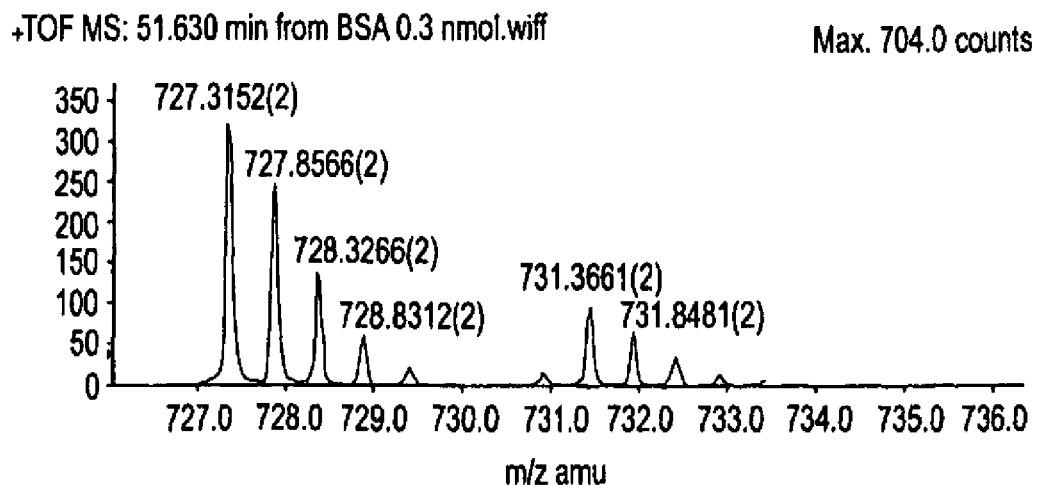

An example of isotopic fractionation of ICAT-$^2$H$_0$ and $^2$H$_8$ labeled peptides is seen in the case of QNCDQFEK (SEQ ID NO:1). Derivatization was at the single cysteine residue in the peptide. The $^2$H$_8$ labeled peptide eluted approximately 28 seconds earlier than the non-deuterated peptide, causing an enormous variation in abundance ratio across the elution profile of the isoforms (FIGS. 6A-D). Resolution of the isoforms was calculated to be 0.74. Even the chromatographic peak shapes of the deuterated and non-deuterated peptides can differ (FIG. 6A). It is readily seen that the only accurate way to quantify the abundance ratio in the initial sample is through a comparison of the integrated extracted ion chromatograms of the isoforms.

Resolution of tryptic peptides from a digest of bovine serum albumin is seen in FIG. 8. Twenty percent of the peptides examined in this limited study showed a resolution of greater than 0.5. Of this number, three fourth were derivatized with two molecules of ICAT reagent. In fact, half the peptides derivatized with two molecules of ICAT reagent showed a resolution of greater than 0.5. In contrast, only 23% of singly labeled peptides had a resolution greater than 0.4. It is also seen in FIG. 8 that isotope effects tend to become smaller with increasing molecular weight of the peptide, particularly with those that are singly derivatized.

Resolution of peptide isoforms is an important concern for a number of reasons. One is the matter of ionization efficiency across the elution profile of the isoforms. It is probable that in a complex mixture that peptides eluting in the leading and tailing parts of a peak are different. If sample matrix components diminish ionization efficiency more in one part of an analyte peak than another does, there is a problem in ESI-MS. Integrated peak areas will not be accurate in cases where the ionization efficiency of a compound varies during peak elution. Moreover, ionization efficiency could vary between the isoforms when they are partially resolved for the same reason.

Figure 6E:
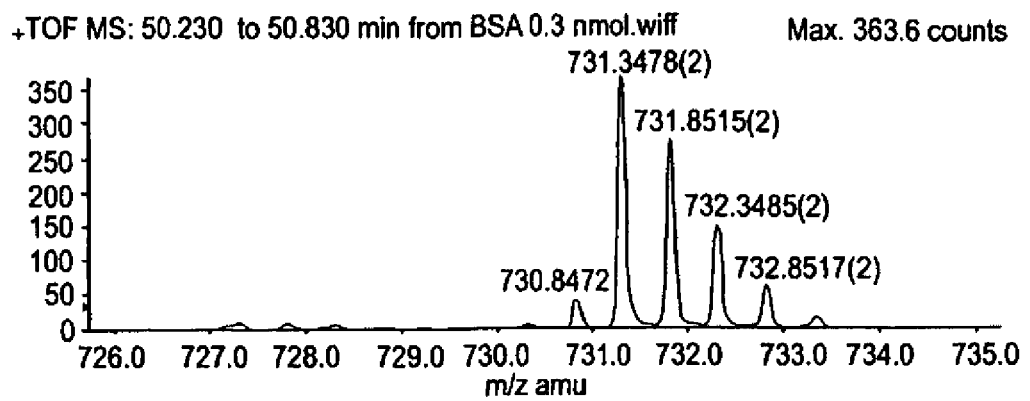
Figure 6F:
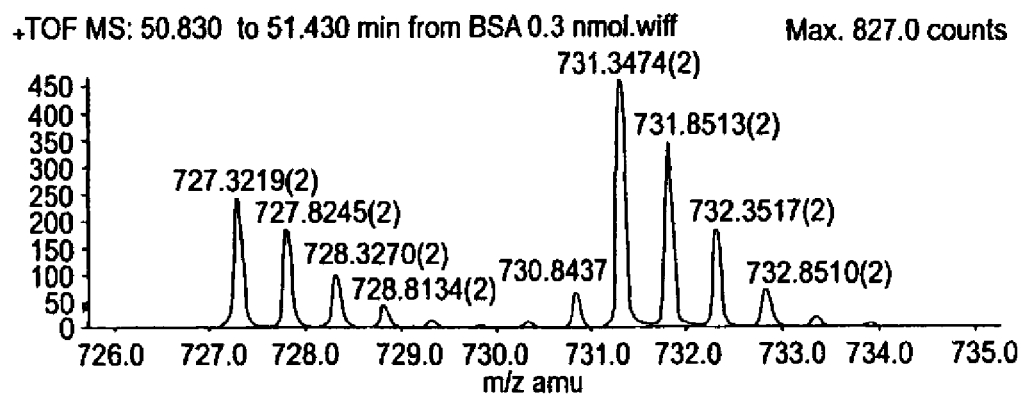
Figure 6G:
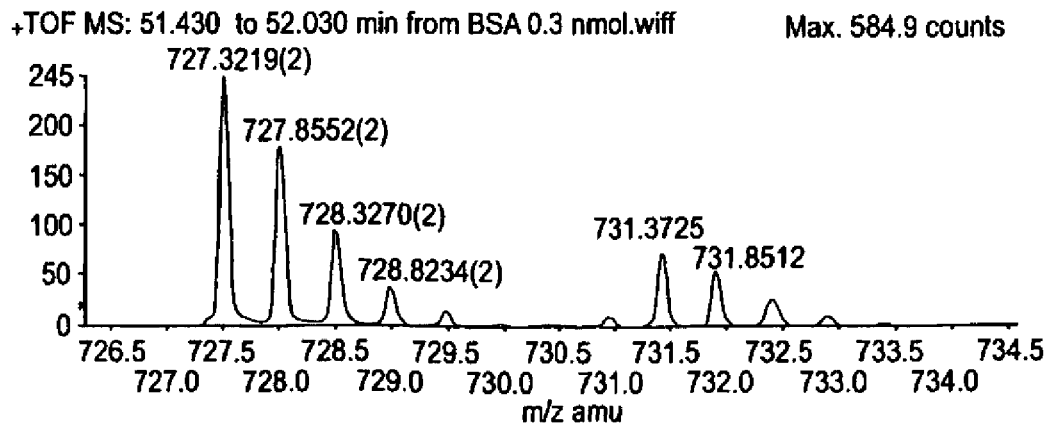

A similar problem occurs with MALDI-MS. Large numbers of peaks will overlap in the reversed phase elution profile of complex tryptic digests and there will be no distinct peaks. This means that fraction collection for MALDI-MS from chromatography columns will be time based and there is a high probability components will inadvertently be split into multiple fractions. When isotopic isoforms are differentially resolved in these fractions they will differ substantially in abundance ratio as the simulation in FIG. 6E-G shows. The problem is in knowing the portion of the analyte present in each fraction that is needed to calculate the true abundance ratio in the initial sample.

Still another problem is that it is necessary to wait until both isoforms elute before extracted ion chromatograms can be constructed and peak areas can be calculated to determine abundance ratio. When the objective is to identify only those components in the mixture that have been up or down-regulated and there is a need for MS/MS data to identify a peptide that has changed in concentration, the isoforms will have eluted before it is known that MS/MS sequence data is needed. This means that either MS/MS data must be acquired on all components as they elute, which is difficult to do, or the sample must be run a second time to acquire the necessary MS/MS data, which costs more time and sample.

Figure 7A:
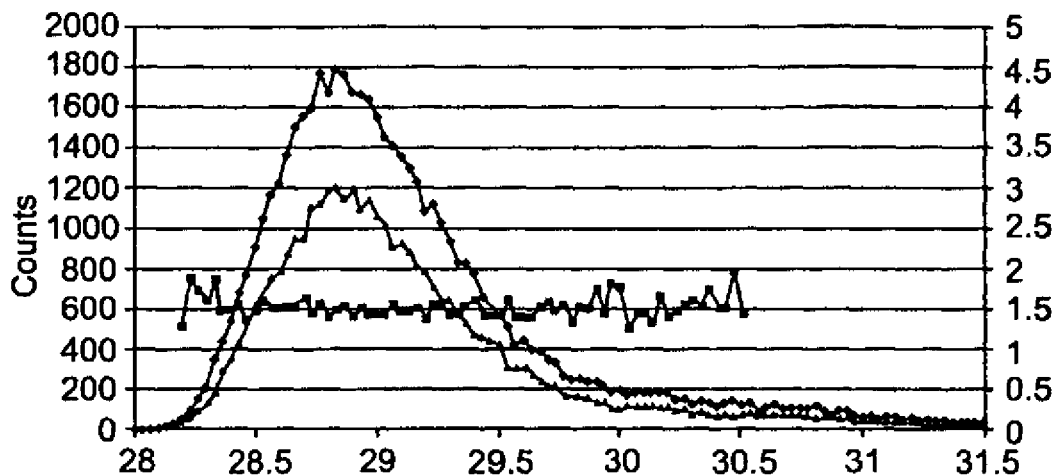
Figure 7B:
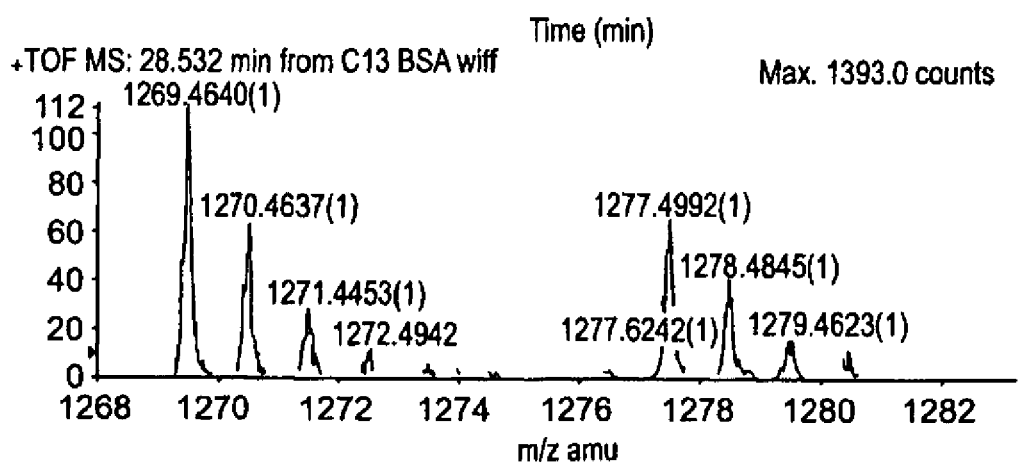
Figure 7C:
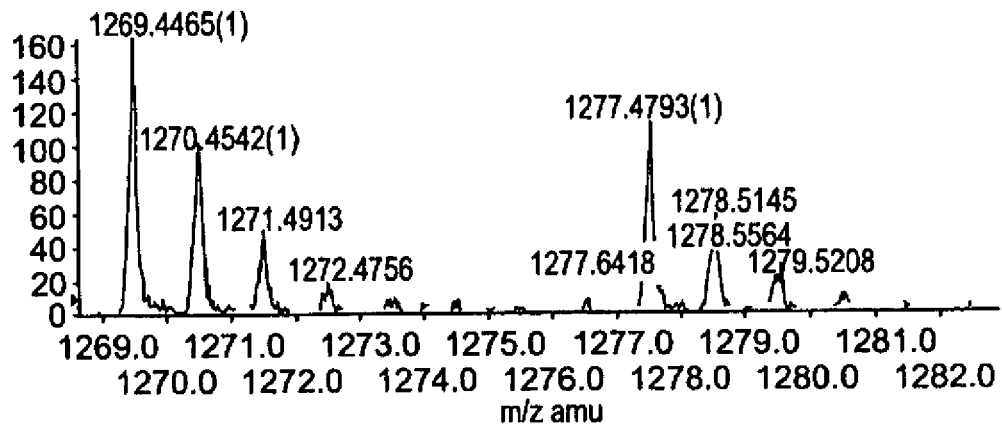
Figure 7D:
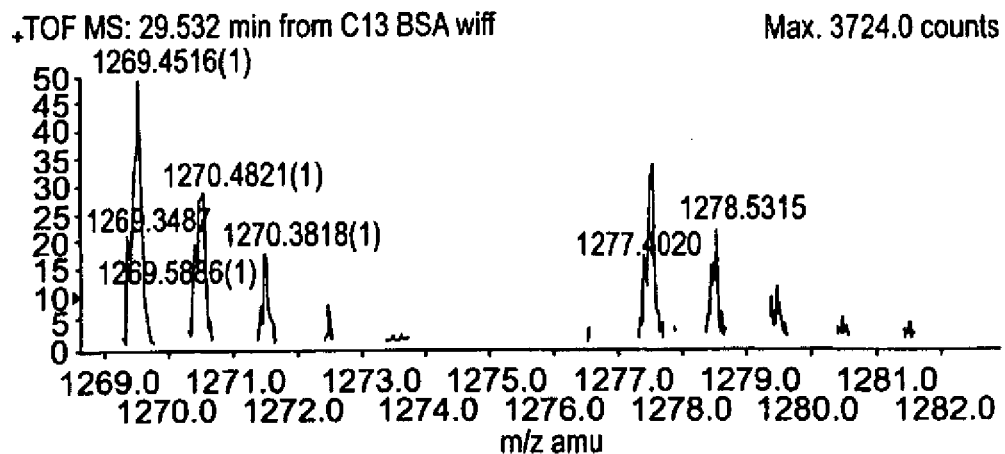

Isotope effects with $^{13}C$ succinate. Succinic anhydride (FIG. 5A) derivatizes primary amine groups in peptides at their N-termini and in lysine residues. This means that each peptide produced during proteolysis can be derivatized. The exception would be rare peptides 1) that do not contain a lysine residue and 2) are derived from the amino terminus of an amino terminally blocked protein. Differential labeling of tryptic digests from control and experimental samples with $^{13}C_0$ and $^{13}C_4$-succinic anhydride respectively, produces peptide isoforms that vary by 4 and 8 atomic mass units (amu). Peptides with a C-terminal arginine appear in mass spectra as a double cluster of ions separated by 4 amu whereas C-terminal lysine-containing peptides are separated by 8 amu. In the case of the peptide QNCDQFEK (SEQ ID NO:1), two moles of succinate were added when it was derivatized with succinic anhydride. The reversed-phase chromatography elution profile of the $^{13}C_0$ and $^{13}C_4$-succinate labeled isoforms of QNCDQFEK (SEQ ID NO:1) is seen in FIG. 7A. Resolution of the isoforms was calculated to be −0.0043. This is within the measurement error of the method. The fact that there is no detectable resolution of the isoforms means that the abundance ratio will be constant across the elution profile (FIG. 7A-D). Resolution of all the peptide isoforms from a tryptic digest of BSA falls between +0.01 and −0.01 (FIG. 9), again within experimental error.

It is important to know that there was no evidence of peptide fractionation based on the content of natural heavy isotopes in peptides. In view of the fact that all peptides contain small amounts of $^{13}C$ and $^{2}H$ from the occurrence of these isotopes in nature, it is interesting that they were not observed to resolve in reversed phase chromatography. This is probably because the isotope peaks of unlabeled peptides are due mainly to $^{13}C$. The natural abundance of $^{13}C$ is 1.10% whereas that of $^{2}H$ is 0.015%. Although peptides have roughly twice as many hydrogen as carbon atoms, few peptides would contain more than one or two deuterium atoms. The lack of isotope effects in the fractionation of $^{13}C$ labeled peptides and the corresponding natural monoisotopic peptides means they could be added together to calculate the ratio between experimental and control samples to improve the precision of abundance ratio measurement.

A direct comparison of peptide resolution caused by succinic anhydride-$^{13}C_4$ and ICAT-$^{2}H_8$ in the same group of peptides is seen in Table 6. ICAT-$^{2}H_8$ caused significant resolution between the isotopically labeled peptides, while succinic anhydride-$^{13}C_4$ did not. Clearly, coding labeling agents with $^{13}C$ is vastly superior to $^{2}H$ coding. A second major advantage of succinate labeling is that the number of peptides labeled is much broader. All peptides in tryptic digests are labeled except those that are N-terminally blocked and contain no lysine.

Conclusion

It was observed during reversed-phase chromatography of peptides from a BSA tryptic digest differentially labeled with the $^{2}H_0$ and $^{2}H_8$-ICAT reagents that resolution of the isoforms exceeded 0.5 with 20% of the peptides in the digest. Three fourth of the peptides in this group contained two cysteine residues and were doubly labeled. Only 23% of the peptides labeled with a single ICAT residue had a resolution greater than 0.4.

The resolution of peptides differentially labeled with $^{13}C$ and $^{12}C$-succinate never exceeded ±0.01, even in the case of peptides from the BSA digest labeled with two moles of succinate. Because this value is within the limits of the method used to determine resolution, it was concluded the $^{13}C$ and $^{12}C$ coded isoform of labeled peptides did not resolve. Abundance ratio in the case of $^{13}C/^{12}C$ coding could be determined from a single mass spectrum taken at any point in the elution profile. This enabled abundance ratio analysis to be completed early in the elution of a peptide from chromatography columns.

It is concluded that isotopic fractionation can be minimized in isotope based, internal standard methods for quantifying relative concentrations of peptides by using coding reagents containing $^{13}C$ instead of $^{2}H$. As a result of eliminating isotope effects in reversed phase chromatography, quantification can be achieved much faster and with greater accuracy. This is expected to improve throughput and pave the way for real-time monitoring and intelligent data analysis.

TABLE 6

Comparison of resolution (R) caused by succinic anhydride-$^{13}C_4$ and ICAT-$^{2}H_8$.

| peptide sequence | R (succinic anhydride-$^{13}C_4$) | number of $^{13}C$ | R (ICAT-$^{2}H_8$) | number of $^{2}H$ |
|---|---|---|---|---|
| CASIQK (SEQ ID NO:6) | −0.0081 | 8 | 0.32 | 8 |
| GACLLPK (SEQ ID NO:7) | 0.0012 | 8 | 0.41 | 8 |
| LCVLHEK (SEQ ID NO:8) | 0.0015 | 8 | 0.4 | 8 |
| QNCDQFEK (SEQ ID NO:1) | −0.0043 | 8 | 0.74 | 8 |
| SHCIAEVEK (SEQ ID NO:9) | 0.0044 | 8 | 0.15 | 8 |
| SLHTLFGDELCK (SEQ ID NO:10) | 0.0091 | 8 | 0.27 | 8 |
| YICDNQDTISSK (SEQ ID NO:11) | 0.004 | 8 | 0.33 | 8 |
| LFTFHADICTLPDTEK (SEQ ID NO:12) | −0.0045 | 8 | 0.28 | 8 |
| GLVLIAFSQYLQQCPFDEHVK (SEQ ID NO:13) | 0.0083 | 8 | 0.18 | 8 |
| MPCTEDYLSLILNR (SEQ ID NO:14) | −0.0025 | 4 | 0.21 | 8 |

Example 3

High Throughput Proteomics by Minimizing Isotopic Fractionation and Intelligent Data Acquisition (IDA)

This work further demonstrates that the isotopic fractionation can be minimized by using reagents containing $^{13}C$ or $^{18}O$ instead of $^{2}H$, which in turn allows accurate quantification of relative protein expression/modification levels and high throughput identification of up or down-regulated proteins by real time ratio determination (RTRD) and intelligent data acquisition (IDA). An accurate ratio between experimental and control samples can be determined in the early stage of their elution peak, and only those peptides that are significantly up or down-regulated need to be fragmented.

Materials and Methods

Materials. Cytochrome c, HPLC grade acetonitrile (ACN), N-hydroxysuccinimide, ammonium bicarbonate, succinic anhydride, acetic anhydride, acetyl chloride, phosphorus pentoxide, urea, hydroxylamine hydrochloride were purchased from Sigma-Aldrich (St. Louis, Mo.). Trifluoroacetic acid (Sequanal Grade) was purchased from Pierce (Rockford, Ill.). Sequencing grade modified trypsin was purchased from Promega (Madison, Wis.). Acetic-$^{2}H_6$-anhydride, succinic-$^{2}H_4$-anhydride, $^{18}O$ enriched water (95% enrichment), butanedioic-$^{13}C_2$-acid were purchased from Isotec (Miamisburg, Ohio). C18 column (4.6×250 mm) was purchased from Vydac (Hesperia, Calif.). Double diionized water (ddI $H_2O$) was produced by a Milli-Q™ Gradient™ A10 System from Millipore (Bedford, Mass.).

Proteolysis of cytochrome c. Cytochrome c (2 mg/mL) was mixed with sequencing grade modified trypsin at ratio of 50:1 (w/w). Proteolysis was carried out in 50 mM ammonium bicarbonate buffer for 12 hours at 37° C. and stopped by freezing the mixture in liquid nitrogen for 10 minutes. Proteolysis was performed in $^{18}O$ enriched water (95% enrichment) in the $^{18}O$ labeling experiments.

Synthesis of N-acetoxy-$^{2}H_3$-succinimide. A solution of 4.0 g of N-hydroxysuccinimide in 11.4 g of acetic-$^{2}H_6$-anhydride was stirred at room temperature. White crystals began to deposit in 10 minutes. After 15 hour the solution was filtered. The crystals were washed with hexane and then dried in vacuum. N-acetoxy-succinimide (synthesized by Peiran Liu), propionate-N-hydroxysuccinimide ester and propionate-$^{2}H_5$-N-hydroxysuccinimide ester (synthesized by Li Xiong) were synthesized in a similar way.

Synthesis of succinic-$^{13}C_2$-anhydride. 2.0 g of butanedioic-$^{13}C_2$-acid and 5 mL of acetyl chloride were heated under reflux for 1.5 hours. After reaction the clear solution was cooled to room temperature and kept at 0° C. overnight. The crystals formed upon cooling was further purified from dry diethyl ether and dried in vacuo over $P_2O_5$.

Derivatization of peptides. A fifty fold molar excess of derivatization reagents (i.e. succinic anhydride, succinic-$^{13}C_2$-anhydride, succinic-$^{2}H_4$-anhydride, N-acetoxysuccinimide, N-acetoxy-$^{2}H_3$-succinimide, propionate-N-hydroxysuccinimide ester and propionate-$^{2}H_5$-N-hydroxysuccinimide ester) were added individually to experimental and control samples in ammonium bicarbonate buffer. Labeling reagents were added in small aliquots over the course of the first hour and the reaction was allowed to proceed for another two hours. N-hydroxylamine was then added in excess and the pH was adjusted to 11-12. Incubation with hydroxylamine was allowed to proceed for 10 min to hydrolyze esters that might have been formed.

Reversed-phase elution of isotopically labeled peptides. Isotopically labeled peptide mixtures were separated by gradient elution from a Vydac C18 column on an Integral Micro-Analytical Workstation (Applied Biosystems, Framingham, Mass.). The C18 column was equilibrated using 100% mobile phase A (0.01% TFA in ddI $H_2O$) at a flow rate of 1.0 mL/min for 2 column volumes (CV). Isotopically labeled peptide mixtures (2 nmol) were injected and gradient elution of the analytes was achieved using 100% mobile phase A to 60% mobile phase B (95% ACN/0.01% TFA in ddI $H_2O$) over 60 minutes, then 60% B to 100% B in 10 minutes at a flow rate of 1.00 mL/min. The gradient was then held at 100% mobile phase B for an additional 10 minutes. Throughout the analysis an on-line UV detector set at 214 nm was used to monitor separation of the peptide mixtures. The peptides were simultaneously monitored by ESI-MS by directing 5% of the flow to the ion source.

ESI-MS analysis. Mass spectral analyses were performed using a QSTAR workstation (Applied Biosystems, Framingham, Mass.) equipped with an Ionspray source. All spectra were obtained in the positive TOF mode at a sampling rate of one spectrum every two seconds. During the LC-MS acquisition, masses were scanned from m/z 300 to 1500.

Results and Discussion

The goals of this study are to (1) determine the degrees of isotopic fractionation of peptides derivatized by various reagents containing $^{2}H$, $^{13}C$ or $^{18}O$, (2) illustrate the problems when isotopic fractionation is significant, (3) demonstrate that isotopic fractionation can be minimized by using reagents containing $^{13}C$ or $^{18}O$ instead of $^{2}H$, which then allows real time ratio determination (RTRD) and intelligent data acquisition (IDA).

Tryptic peptides from cytochrome c were isotopically labeled, mixed and subjected to LC-MS separation and quantification. FIG. 11 shows mass spectra of a peptide (IFVQK; SEQ ID NO:2) labeled by succinic anhydride (m/z=834.4, control sample), succinic-$^{13}C_2$-anhydride (m/z=838.4, experimental sample 1) and succinic-$^{2}H_4$-anhydride (m/z=842.4, experimental sample 2) at different time. Four $^{13}C$ and eight $^{2}H$ were incorporated in experimental sample 1 and experimental sample 2 respectively because both the amine group at the amino terminus and the lysine at the carboxyl terminus were derivatized by succinic anhydride. FIG. 11 demonstrates that the ratio between experimental sample 1 and control sample does not change with time while the ratio between experimental sample 2 and control sample varies continuously with time.

A more quantitative analysis is seen in FIG. 12. FIG. 12 shows the extracted ion chromatograms of monoisotopic peaks at m/z of 834.4 (control sample), 838.4 (experimental sample 1) and 842.4 (experimental sample 2) and the ratios between experimental samples and control sample. The continuously decreasing ratio between the $^{2}H$ labeled experimental sample 2 and the non-isotope labeled control sample indicates that the $^{2}H$ labeled peptide eluted significantly earlier than the non-isotope labeled control sample. The $^{2}H$ labeling even changed the shape of the chromatographic peak which can be easily visualized and is also indicated by the increase of the ratio late in the chromatographic peak.

On the contrary to $^{2}H$, no significant isotopic fractionation was observed between the $^{13}C$ labeled peptide and non-isotope labeled peptide, as the ratio between them was constant across the chromatographic peak (FIG. 12).

The same analysis was done to the individual isotope peaks (m/z=835.4, 836.4, 837.4, FIG. 11), which showed no significant separation from the monoisotopic peak (m/z=834.4, FIG. 11). One reason could be that the isotope peaks at m/z of 835.4, 836.4 and 837.4 mainly consist of $^{13}C$, etc. but not $^2H$ because the natural abundance of $^2H$ (0.015%) is much lower than that of $^{13}C$ (1.10%) etc. Another reason could be that the heavy isotopes ($^{13}C$ etc.) randomly distribute in the whole peptide instead of being enriched in one particular functional group. The insignificant fractionation between the isotope peaks and the corresponding monoisotopic peak indicates that they can be added together to calculate the ratio between experimental and control samples to improve the precision of the ratio measurement.

As in Example 2, resolution (R) is defined as $$R = \frac{\Delta}{W_{1/2}} \quad (11)$$

where $\Delta$ is the separation between the heavy isotope labeled experimental samples and the non-isotope labeled control sample and $W_{1/2}$ is the average full peak width at half maximum (FWHM) of the extracted ion chromatographic peaks of experimental and control samples.

Figure 13A:
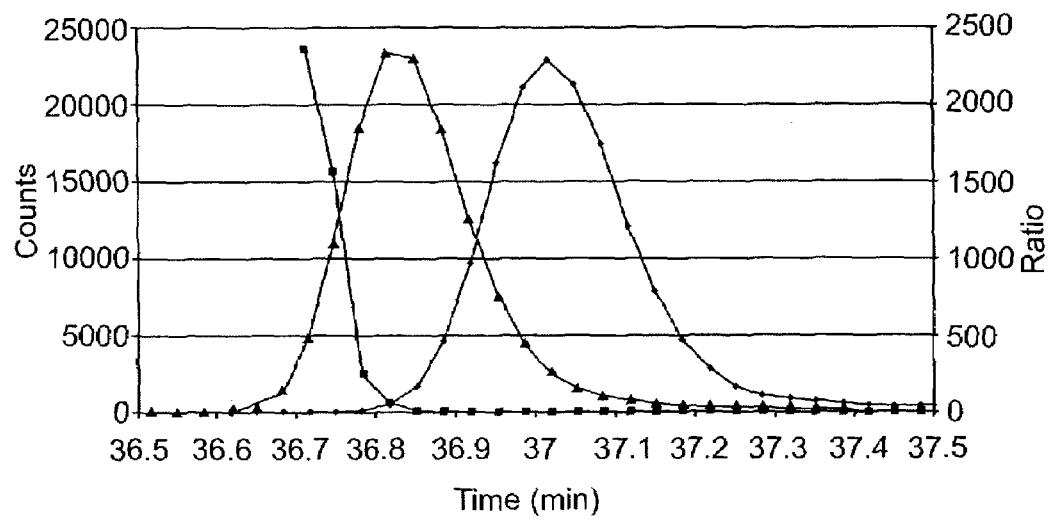
Figure 13B:
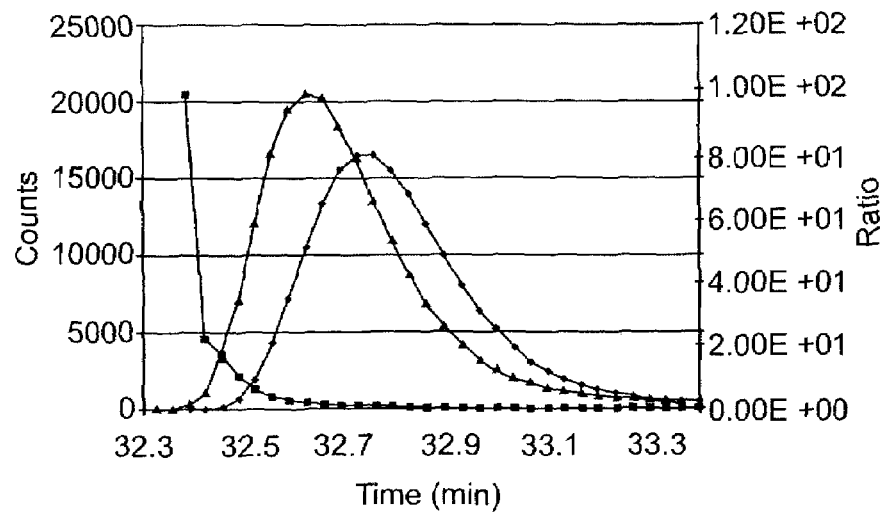
Figure 13C:
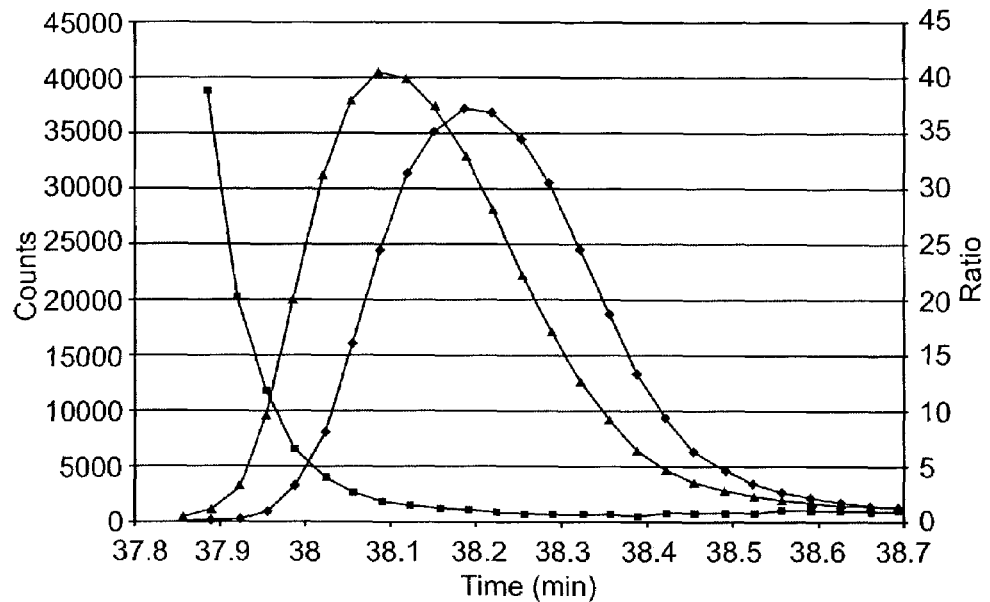
Figure 13D:
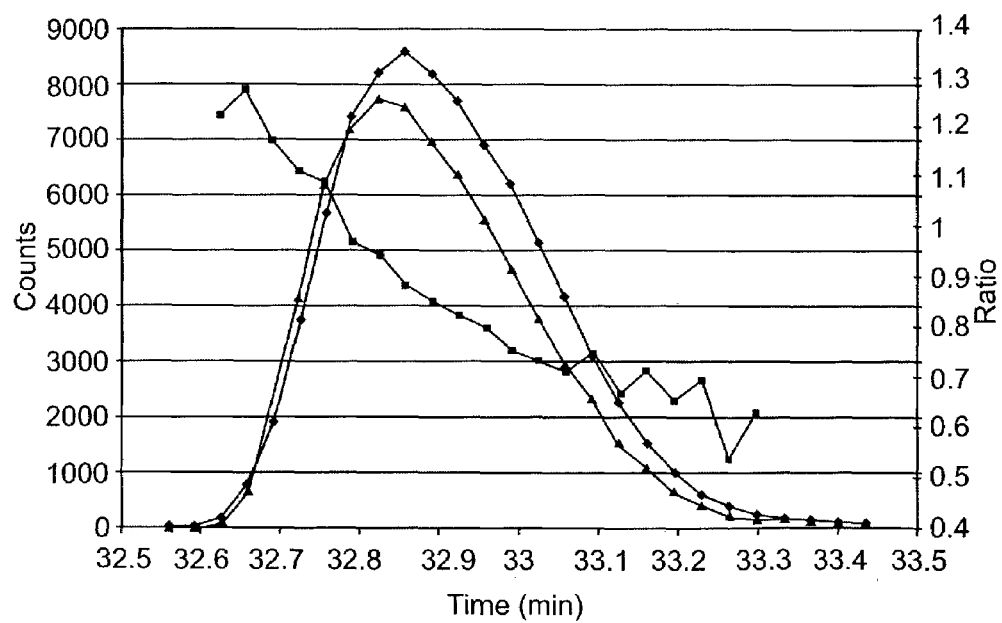

Peptides labeled by propionate-$^2H_5$-N-hydroxysuccinimide ester showed the greatest resolution (R) among all the five reagents tested (FIG. 13A). The resolution is so large that most of the time the deuterated and non-deuterated peptides do not even show up in the same mass spectrum! When fractions are collected in the LC separation of a complicated peptide mixture, it is very probable that the deuterated and non-deuterated peptides go to two different fractions so that the isotope ratio cannot be measured at all. Instead they may be mistakenly regarded as grossly up or down-regulated peptides since they appear as single isotope cluster instead of two isotope clusters with certain mass difference. The popular ICAT reagent causes equal or larger R as eight or more deuterium is incorporated depending on the number of cystine the peptide has.

Resolution (R) caused by succinic-$^2H_4$-anhydride (FIG. 13B) and N-acetoxy-$^2H_3$-succinimide (FIG. 13C) are comparable to each other and much smaller than that of propionate-$^2H_5$-N-hydroxysuccinimide ester while they are still significant. When fractions are collected to do MALDI-MS or nanospray-MS, they could be enriched in either the deuterated or non-deuterated peptides so that the isotope ratios are not accurate. In online LC-MS experiments ratio may be estimated in two ways. One way is to calculate the ratio based on integration of the extracted ion chromatographic peaks of individual isotopically labeled peptides, which can only be done after the peptides completely elute from column so that real time ratio determination (RTRD) and intelligent data acquisition (IDA) are impossible. A better way is to keep tracking the intensities of elution peaks of deuterated and non-deuterated peptides. Once the non-deuterated peptide reaches peak maximum, the ratio is estimated based on integrated peak area of the leading half of the non-deuterated and deuterated peptides. The peptides are fragmented in the trailing half of the elution peaks if the ratio is significantly different from one. It works when peak shapes of the isotopically labeled peptides are the same, which is not always true for the $^2H$ labeling reagents (e.g. FIG. 13).

$^{18}O$ can be incorporated into peptides during trypsin digestion and be used in quantification. $^{18}O$ labeling could be a valuable alternative to amino acylation strategies. However, important issues in case of $^{18}O$ labeling are that (1) more than one $^{18}O$ can be incorporated into a peptide, (2) incorporation varies with structure, and (3) peptides arising from the C-terminus of a protein are not labeled.

Incorporation of multiple molecules of $^{18}O$ into a peptide is a unique property of trypsin as opposed to other proteolytic enzymes. Apparently, trypsin covalently associates reversibly with peptides containing basic C-terminal amino acids. Exchange of $^{18}O$ into these peptides even occurs in the absence of proteolysis when $H_2^{18}O$ is added to a trypsin digest still containing trypsin. We found that this reaction is sometimes inhibited by urea. When urea is eliminated, in many cases two molecules of $^{18}O$ are incorporated in pure $H_2^{18}O$. Again resolution varied between peptides with the greatest resolution occurring in smaller peptides.

In this example, resolution caused by $^{18}O$ (FIG. 13D) was smaller than that of succinic-$^2H_4$-anhydride and N-acetoxy-$^2H_3$-succinimide. However, it can still cause 15% or more errors when fractions are collected in the worst cases. Also the resolution is still not small enough to allow real time ratio determination (RTRD) from single mass spectrum snapshot because, for example, in FIG. 13D ratio varied from 1.3 to 0.6 across the elution peak when the true value is 0.87. In this case real time ratio determination (RTRD) works well using the integration of the leading halves of the elution peaks of isotopically labeled peptides because now R is sufficiently small and peak shapes are identical.

Figure 13E:
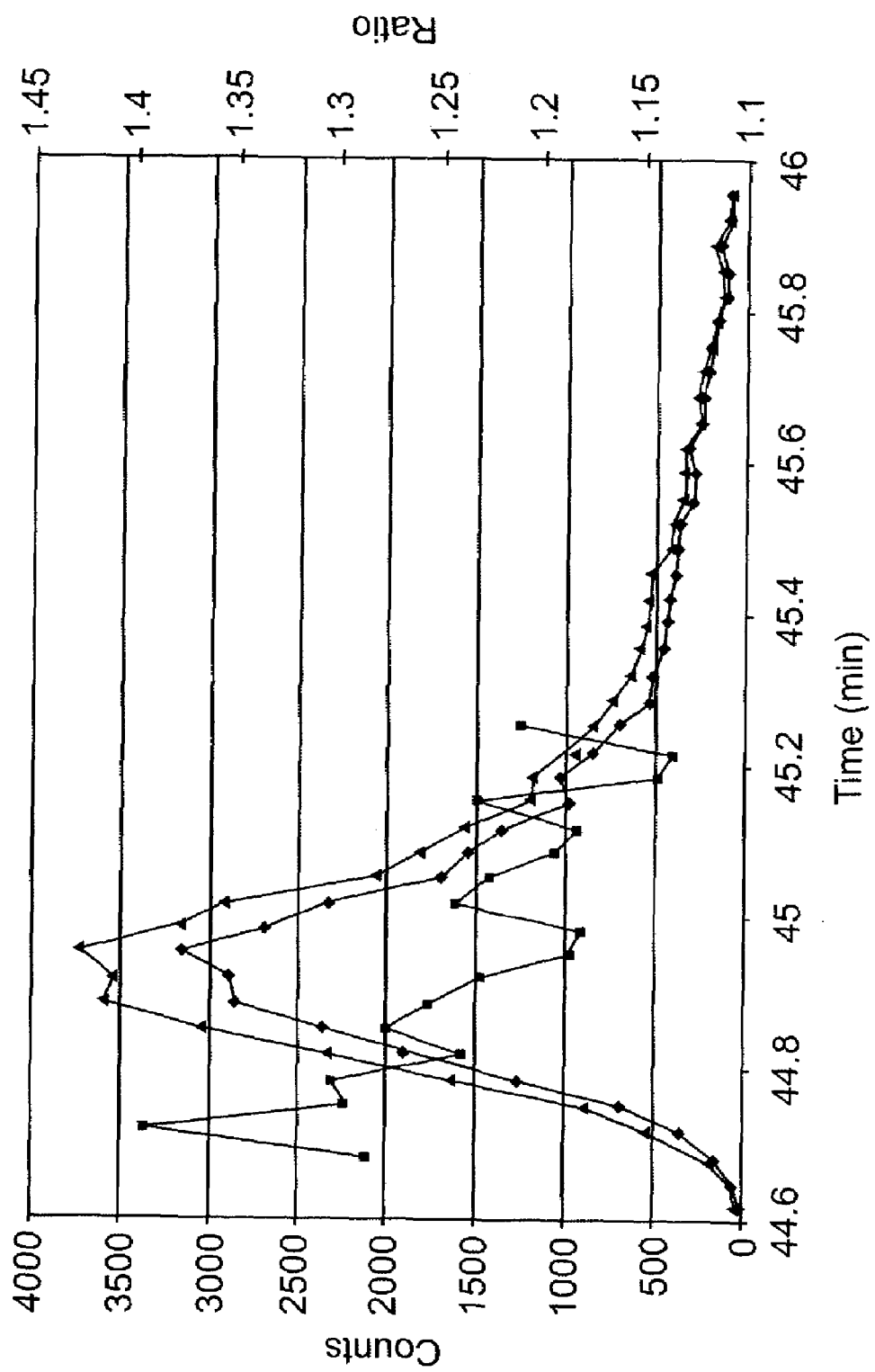
Figure 14A:
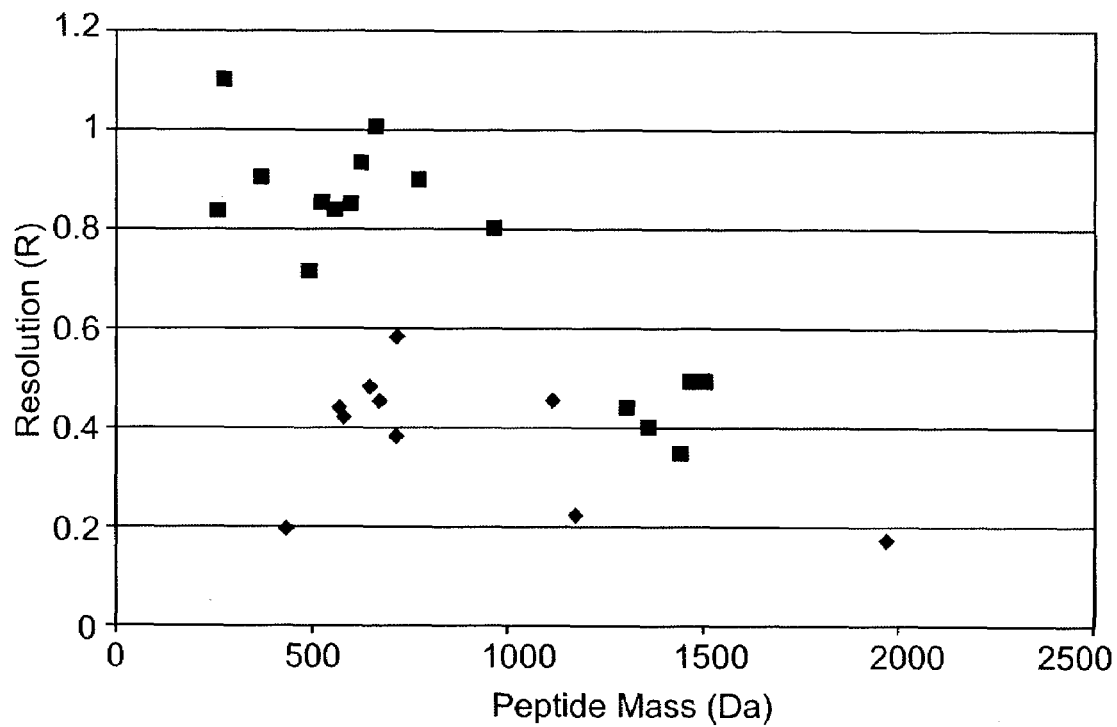
Figure 14B:
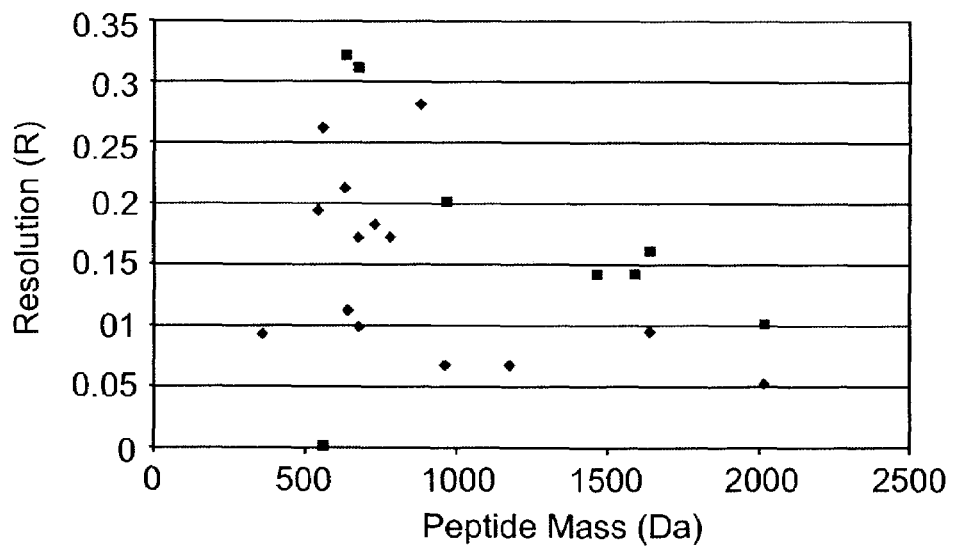
Figure 14C:
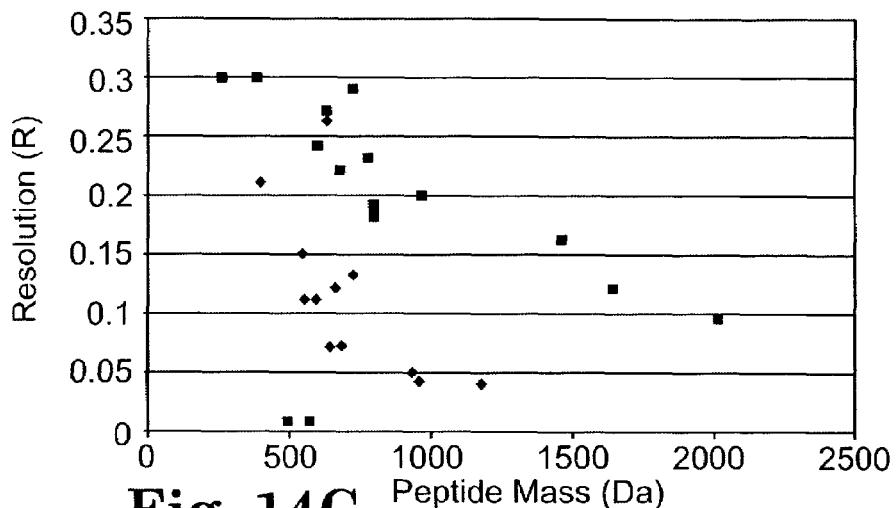
Figure 14D:
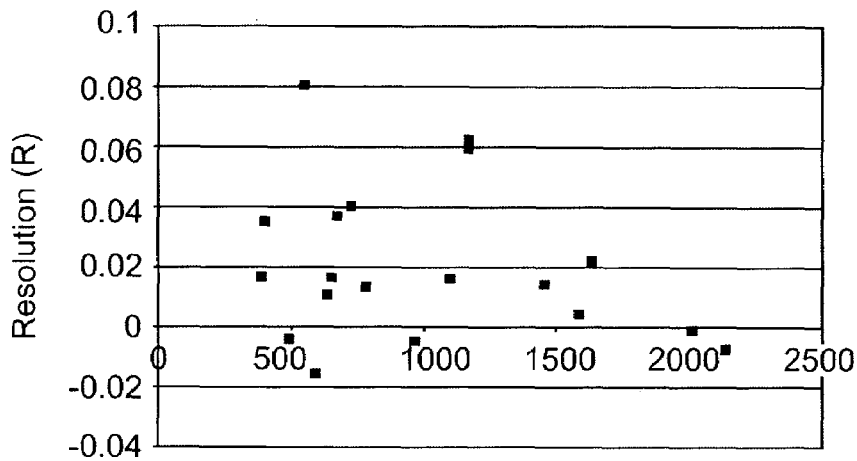
Figure 14E:
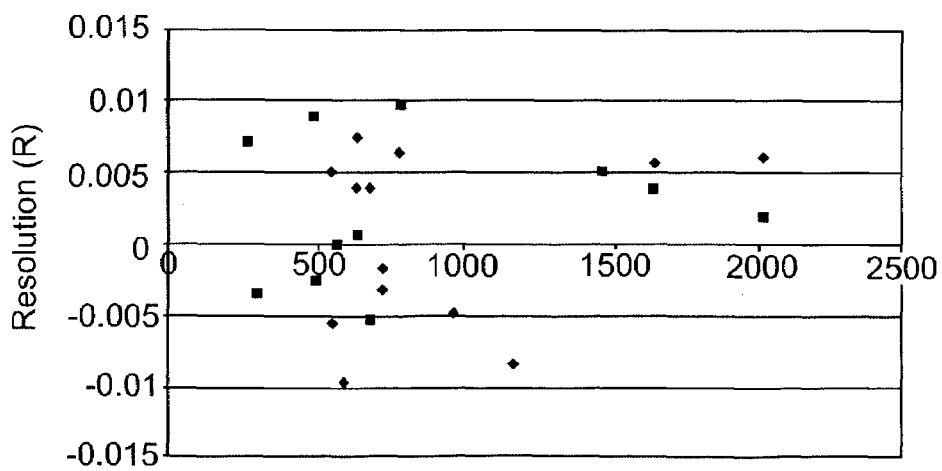

Succinic-$^{13}C_2$-anhydride showed the smallest resolution among all five reagents tested in this work. In FIG. 13E, ratio varied less than 5% across the elution peak. Now systematic errors are negligible (less than 1%) when fractions are collected. Real time ratio determination (RTRD) can be performed much earlier before reaching the peak maximums, which leaves more time for optimizing conditions and accumulate high quality MS/MS spectra.

Also minimizing R makes the accurate isotope ratios preserved in the fragment ions when the mass windows are wide enough that two isotope clusters are simultaneously fragmented. This is particularly useful when multiple pairs of peptides overlap in mass spectra. It is difficult to do deconvolution to obtain the accurate isotope ratios of each pair of peptides. In this case, the only hope is that different pairs of peptides generate different fragment ions and some of the fragment ions do not overlap with others and thus allow the calculation of accurate isotope ratios of original pair of peptides. The ratio calculated based on fragment ion clusters in MS/MS spectra reflect the ratio at the point that the fragmentation takes place, which could be very different from the true value when R is not small and ratio varies across the elution peak.

FIG. 14 shows that the larger the peptide mass the smaller the resolution (R). Also in all the cases of $^2H$ labeling, peptides end with lysine are derivatized twice, have twice as many $^2H$ as peptides end with arginine, and have a correspondingly larger R when peptide masses are similar. Even resolution of peptides having similar masses and are derivatized by the same reagent with the same amount of $^2H$ or $^{18}O$ incorporation still varies, which means resolution also depend on peptide sequences/structures. However, Resolution is independent of peptide retention time as resolution is dependent of peptide mass and retention time is independent of peptide mass. In the case of $^{13}C$ labeling no clear pattern was found probably because R is already within measurement error.

FIG. 15 again shows the decrease of resolution in the order of propionate-$^2H_5$-N-hydroxysuccinimide ester, succinic-$^2H_4$-anhydride, N-acetoxy-$^2H_3$-succinimide, $H_2^{18}O$, succinic-$^{13}C_2$-anhydride in the cases of three peptides from cytochrome c. Resolution (R) should also depend on column and gradient program.

An interesting fact is that the natural abundance of $^2H$ (0.015%) is much lower than that of $^{13}C$ (1.10%), $^{18}O$ (0.2%) or $^{15}N$ (0.37%). However, reagents containing $^2H$ are much cheaper than that containing $^{13}C$, $^{15}N$, $^{18}O$ etc. The reason may be that the difference between $^2H$ and $^1H$ is much larger than that between $^{13}C$ and $^{12}C$, $^{15}N$ and $^{14}N$, $^{18}O$ and $^{16}O$, etc. and thus $^2H$ is the easiest heavy isotope to purify. At the mean time the large difference between $^2H$ and $^1H$ makes deuterated compounds not the best internal standards.

Another fact is that the cost of $^{13}C$ containing reagents is not very high considering only several milligrams of reagents is used in each experiment, while gains in accuracy and throughput are very significant.

Example 4

Chemically Multiplexed Global Internal Standard Technology (mGIST)

Elimination of Isotope Effect Makes Multiplexing Possible

The global internal standard technique (GIST) (PCT WO 01/86306, published Nov. 15, 2001; U.S. patent application Ser. No. 09/849,924) allows 1) quantification in the cases of both protein expression and post-translational modifications as they relate to cellular regulation and 2) quantification may be achieve with all types of targeting schemes. Through various kinds of group specific chromatographic selectors, it is possible to target natural features of peptides and proteins for selection and subsequent analysis. For example, in the case of protein expression, either histidine- or cysteine-containing peptides or those that contain both of these amino acids can be selected. (Surprisingly, almost as many proteins produce a tryptic peptide carrying both histidine and cysteine as either amino acid alone. The great advantage of double selection is that there are so many fewer peptides with both amino acids.) As another example, post-translational modifications such as glycosylation and phosphorylation can also be used for selection.

There remains the problem of increasing throughput. A number of recent presentations have addressed the throughput issue with what we call the "Gatling gun" or physical multiplexing approach. Although there are many clever ways to achieve parallel processing with LC/MS instrumentation, all the reports have a common thread. Separations are carried out with multiple columns or gels simultaneously and fractions from each column or gel are either 1) mechanically collected or transferred directly onto a MALDI plate for later analysis in a single mass spectrometer, 2) electrosprayed into a single mass spectrometer through valve switching, or 3) electrosprayed into one of an array of mass spectrometers. The requisite replication and synchronization of multiple components can be both costly and complex. Equally important is the fact that the total number of column fractions (F) generated by a mechanically multiplexed systems is equal to the number being generated from a single column times the number of columns (N), i.e. F=fN. Because a mass spectrum must be generated for each of these fractions, the total number of mass spectra (S) taken will be directly proportional to F. This means that mechanical multiplexing neither reduces the number of spectra that must be taken nor the amount of sample processing that must be done. S is the same in all cases. Only the number of samples delivered per unit time changes.

An alternative strategy to increase throughput in proteomics using "chemical multiplexing" (mGIST) is possible. mGIST means synthesizing multiple reagents which are chemically identical but have different numbers of isotopes. We can then use the reagents to "code" multiple samples simultaneously. We already know that 1) the global derivatization strategies described above make it possible to code every peptide in a sample without regard to sample complexity, 2) identical peptides from two samples can be traced through complex analyses involving many steps, 3) when a coded peptide has been identified or sequenced, the sequence of isoforms is also known, and 4) relative concentration of an analyte in two samples can be determined when both are analyzed simultaneously. Exploiting these facts could substantially increase throughput. It is expected that this strategy can be expanded to allow 3-5 samples to be analyzed simultaneously.

The concept underlying mGIST is to fill a portion of the unused separation space in mass spectra with isotopically coded forms of peptides from multiple samples, at least until multiple components fill the same separation space, i.e. isobaric peptides are being generated. In mGIST the abundance ratio should be well defined. For example, it is preferred that the abundance ratio be normalized against the most abundant analyte or against a control sample.

This chemical multiplexing approach has many advantages. One is that the number of column fractions being generated is independent of the number of samples being analyzed. Another is that more of the analytical work is being loaded onto the faster, higher resolution mass spectrometer. Still another is that increases in the amount of data processing required are far less than the increase in the number of samples. The fact that throughput would be increased with existing systems is also attractive. And finally, quantitative comparisons between multiple samples could easily be achieved.

Importantly, limiting the resolution of a differentially derivatized peptides as in the preceding Examples enables sample multiplexing during analysis. For example, differential derivatization of samples with a series of isoforms of an isotope coding agent that differ in mass by three daltons (e.g., isoforms having masses of 3, 6 and 9 daltons in excess of the mass of the isoform containing no heavy isotopes) will allow at least four samples to be analyzed concurrently. (For convenience, these heavy isotope isoforms can be generically referred to as $^3$CODR, $^6$CODR and $^9$CODR, respectively, with $^0$CODR referring to isoform that contains no heavy isotopes, and where CODR stands for the coding reagent.) This means that individual components in 3-5 samples can be chemically coded and quantified simultaneously using a single analytical system. Targeted, quantitative proteomics thereby become amenable to chemically multiplexed global internal standard technology (mGIST).

Oxygen-18 mGIST coding reagents. Oxygen-18 has certain features that diminish its attractiveness for mGIST reagents. One is that mass would only increases two amu per oxygen atom added to the coding reagent. A second problem is the abundance issue in organic compounds. Although it is possible to synthesize a set of four mGIST reagents varying by a single $^{18}O$, a correction would have to be made for their overlap with M+2 isotope peaks from natural isotopes containing $^{13}C$ and $^2H$. Corrections work well when the $^2$CODR derivatized peak is equal to or larger than the $^0$CODR peak, but become more problematic as the $^2$CODR derivatized peak becomes smaller relative to the $^0$CODR peak. Distinguishing the $^2$CODR peptide peak from the M+2 peak of the $^0$CODR peptide is difficult when the ($^0$CODR peptide)/($^2$CODR peptide) ratio is high.

It is desirable that coding reagents vary by three or more atomic mass units (amu) to circumvent the problem of overlap with natural isotope peaks. This suggests that coding reagents based on $^{18}$O should vary by two $^{18}$O atoms. At least six $^{18}$O atoms would be required to produce a set of four coding reagents varying by four amu. Carbohydrates and polyoxyethylenes meet this criterion, although the requisite isotopically labeled derivatizing reagents are not at present commercially available.

Carbon-13 coding reagents. It is desirable that the mass difference between coding reagents be at least three amu, production of a 0, +3, +6, and +9 amu set would require a CODR structure with at least nine carbon atoms that could be manipulated.

m-GIST in the study of post-translational modifications. Most of the work in proteomics related to post-translational modification (PTM) is along two lines. One is to use unique mass spectral characteristics to identify particular types of PTM, such as in the case of phosphorylation. This is a lengthy process. Another is to use affinity chromatography systems to select particular types of PTM as we have done with glycosylation and phosphorylation (PCT WO 01/86306, published Nov. 15, 2001). The problem is that affinity selectors may not be available for all types of PTM.

mGIST enables another approach. There are a number of enzymes that cleave post-translational modifications from peptides or proteins. The specificity of these enzymes can be used in an analytical mode for PTM identification. The control sample is split into two fractions and one is treated with the analytical enzyme. Following tryptic digestion of the two fractions, the untreated control would be derivatized with a $^0$CODR and the enzyme treated sample with the $^6$CODR species. The experimental sample would be treated with trypsin and derivatized with the $^3$CODR. All three samples will then be mixed and fractionated.

This strategy leads to the experimental sample being boxed between an untreated and enzyme treated control. This means all peptide peaks will appear as triplet clusters in mass spectra with one exception. Those in which the enzyme cleaved a PTM from the protein will cause peptides to appear as doublet clusters. This unique pattern will be readily apparent and identify the PTM. The first and second clusters may still be used for quantification and location of the PTM by MS/MS sequencing.

This concept can be tested with alkaline phosphatase to detect phosphorylation, low molecular weight tyrosine phosphatase to search for tyrosine phosphorylation, serine/threonine phosphatase, sulfatases, glycosidases, and a variety of other enzymes to detect hydrolysis of their respective substrates.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

SELECTED BIBLIOGRAPHY

S. P. Gygi, B. Rist, S. A. Gerber, F. Turecek, M. Gelb, and R. Aebersold. Quantitative analysis of complex proteins mixtures using isotope-coded affinity tags. Nat. Biotechnol. (1999) 17, 994-999.

J. Ji, A. Chakraborty, M. Geng, X. Zhang, A. Amini, M. Bina, and F. Regnier. Strategy for qualitative and quantitative analysis in proteomics based on signature peptides. J. Chromatogr. B, (2000) 745, 197-210.

X. Yao, A. Freas, J. Ramirez, P. Demirev, and C. Fenselau. Proteolytic $^{18}$O labeling for comparative proteomics: Model studies with two serotypes of adenovirus. Anal. Chem. (2001) 73, 2836-2842.

T. P. Conrads, K. Alving, T. D. Veenstra, M. Belov, G. Anderson, D. Anderson, M. Lipton, L. Pasa-Tolic, J. Udseth, W, Chrisler, B. Thrall, and R. Smith. Quantitative analysis of bacterial and mammalian proteomes using a combination of cysteine affinity tags and 15N metabolic labeling. Anal. Chem. (2001) 73, 2132-2139.

D. Goodlett, A. Keller, J. Watts, R. Newitt, E. Yi, S. Purvine, J. Eng, P, Von Haller, and R. Aebersold. Differential stable isotope labeling of peptides for quantitation and de novo sequence derivation. Rapid Commun. Mass Spectrom. (2001) 15, 1214-1221.

R. Zhang, C. Sioma, S. Wang, and F. Regnier. Fractionation of isotopically labeled peptides in quantitative proteomics. Analytical Chemistry, (2001) 73, 5142-5149.

A. Amini, S. Dormady, L. Riggs, Larry; and F. Regnier. The impact of buffers and surfactants from micellar electrokinetic chromatography on matrix-assisted laser desorption ionization (MALDI) mass spectrometry of peptides. J. of Chromatogr. A, (2000) 894, 345-355.

F. Regnier, A. Amini, A. Chakraborty, M. Geng, J. Ji, L. Riggs, C. Sioma, S. Wang, and X. Zhang, Xiang. Multidimensional chromatography and the signature peptide approach to proteomics. LC/GC, (2001) 19, 200-213.

S. Wang and F. Regnier. Covalent chromatography for the selection of cysteine containing peptides in proteomics. J. Chromatogr. (2001) 924(1-2), 345-357.

M. Larsen, P. Larsen, S. Fey, and P. Roepstroff. Characterization of differently processed forms of enolase 2 from *Saccharomyces cerevisiae* by two-dimensional gel electrophoresis and mass spectrometry. Electrophoresis. (2001) 22, 566-575.

T. Kosaka, T. Takazawa, and T. Nakamura. Identification and C-terminal characterization of proteins from two-dimensional polyacrylamide gels by a combination of isotope labeling and nanoelectrospray fourier transform ion cyclotron resonance mass spectrometry Anal. Chem. (2000) 72, 1179-1185.

P. K. Jensen, L. Pasa-Tolic, G. Anderson, J. Homer, M. Lipton, J. Bruce, and R. Smith. Probing proteomics using capillary isoelectric focusing electrospray ionization Fourier transform ion cyclotron resonance mass spectrometry. Anal. Chem. (1999) 71, 2076-2084.

O. A. Kirgorodskaya, Y. P. Koz'min, M. I. Titov, N. V. Savel'eva, R. Komer, C. Sonksen, A. I. Miroshnikov, P. Roepstorff. Quantitative determination of peptides and proteins by MALDI MS. Fuss. J. Biorg. Chem. (2000) 26, 593-602.

B. Kuster and M. Mann. $^{18}$O labeling of N-glycosylation sites to improve the identification of gel-separated glycoproteins using peptide mass mapping and database searching. Anal. Chem. (1999) 71, 1431-1440.

J. D. Watson. The human genome project; past, present, and future. Science. (1990) 248, 44-49.

M. Washburn, D. Wolthers, and J. Yates. Large-scale analysis of the yeast proteome by multidimensional protein identification technology. Nat. Biotechnol. (2001) 19, 242-247.

M. Mann, R. Hendrickson, and A. Pandey. Analysis of proteins and proteomes by mass spectrometry. Ann. Rev. Biochem. (2001) 70, 437-473.

N. Anderson, A. Matheson, and L. Anderson. Back to the future: the human protein index (HPI) and the agenda for post-proteomic biology. Proteomics (2001) 1, 3-12.

B. Walsh, M. Molloy, and K. Williams. The Australian proteome analysis facility (APAF). Assembling large-scale proteomics through integration and automation. Electrophoresis. (1998) 19, 1883-1890.

G. Cothals and P. Nelson. Large-scale proteomics and its future impact on medicine. Pharmagocgenomics J. (2001) 1, 15-19.

M. Van der Werf, F. Schuren, S. Bijlsma, A. C. Tas, and B. Van Ommen. Nutrigenomics: application of genomics technologies in nutritional sciences and food technology. J. Food Sci, (2001) 66, 772-780.

G. Thomas. Metabolomics breaks the silence. Trends Biotech. (2001) 19, 126-127.

O. Fiehn. Combining genomics, metabolome analysis, and biochemical modeling to understand metabolic networks. Comp. Funct. Genomic. (2001) 2, 156-158.

L. Raamsdonk, B. Teusink, D. Broadhurst, N. Zhang, A. Hayes, M. Walsh, J. Berden, K. Brindle, D. Kell, J. Rowland, H. Westerhoff, K. Van Dan, and S. Oliver. A functional genomics strategy that uses metabolome data to reveal the phenotype of silent mutations. Nat. Biotechnol. (2001) 19, 45-50.

M. Foersma, I. Solyanikova, W. Van Berkel, L. Golovleva, and I. Rietjens. $^{19}$F NMR metabolomics for the elucidation of microbial degradation pathways of fluorophenols. J. Ind. Microbiol. Biotechnol. (2001) 26, 22-34.

K. D. W. Roth, Z.-H. Huang, N. Sadagopan, and J. Throck Watson. Charge Derivatization of peptides for analysis by mass spectrometry. Mass Spectrometry. Rev. (1998) 17, 255-274.

L. Andersson. The use of immobilized $Fe^{+3}$ and other hard metal ions in chromatography of peptides and proteins. Int. J. Bio-Chromatogr. (1996) 2, 25-36.

H. Kaufmann, J. Gailey, and M. Fussenegger. Use of antibodies for detection of phosphorylated proteins separated by two-dimensional gel electrophoresis. Proteomics (2001) 1, 194-199.

M. Dwek, J. Ross, and A. Leathem. Proteome and glycosylation mapping identifies post-translational modifications associated with aggressive breast cancer. Proteomics (2001) 1, 756-762.

J. Ji, A. Chakraborty, M. Geng, X. Zhang, A. Amini, M. Bina, and F. Regnier, Fred. Strategy for qualitative and quantitative analysis in proteomics based on signature peptides. J. Chromatogr. B, (2000) 745, 197-210.

M. Geng, X. Zhang, M. Bina, and F. Regnier. Proteomics of glycoproteins based on affinity selection of glycopeptides from tryptic digests. J. Chromatogr. B, (2001) 752, 293-306.

L. Riggs, C. Sioma, and F. Regnier. An Automated Signature Peptide Approach for Proteomics. J. Chromatogr. A, (2001) 924(1-2), 359-368.

H. Wang, C. Desilets, and F. E. Regnier. A Study of Retention Mechanism in Semipermeable Surface Chromatography. Anal. Chem. (1992) 64, 2821-2827.

C. Dass, P. Mihalakshmi, and D. Gandberry. Manipulation of the ion-paining reagents for reversed-phase high-performance liquid chromatographic separation of phosphorylated opoid peptides from their non-phosphorylated analogues. J. Chromatogr. A (1994) 67, 249-257.

M. Schnoelzer, P. Jedrzejeski, W. D. Lehman. Protease-catalyzed incorporation of $^{18}$O into peptide fragments and its application for protein sequencing by electrospray and matrix-assisted laser desorption/ionization mass spectrometry. Electrophoresis. (1996) 17, 945-953.

B. Karger. High throughput mass spectrometry. Ab. Paper. Am. Chem. Soc. (2001) $221^{st}$ IEC-386.

R. D. Rocklin, R. Ramsey, J. M. Ramsey. A microfabricated fluidic device for performing two-dimensional liquid phase separation. Anal. Chem. (2001) 72, 5244-5249.

E. R. Badman and R. G. Cooks. Cylindrical ion trap array with mass selection by variation in trap dimensions. Anal. Chem. (2000) 72, 5079-5086.

S. D. Patterson, R. Aebersold, and D. Goodlett. Mass spectrometry-based methods for protein identification and phosphorylation site analysis. Proteomics (2001) 1, 87-130.

N. Ishizuka, H. Minakuchi, K. Nakanishi, N, Soga, H. Nagayama, K, Hosoya, and N. Tanaka. Performance of monolithic silica column in a capillary under pressure-driven and elctrodriven conditions. Anal. Chem. (2000) 72, 1275-1280.

Parker, K. C.; Griffin, T.; Gygi, S.; Aebersold, R. 48th ASMS Conference on Mass Spectrometry and Allied Topics, 2000.

S. Wang, X. Zhang, and F. Regnier. A quantitative proteomics strategy involving the selection of peptides containing both cysteine and histidine from tryptic digests of cell lysates. J. Chromatogr. A (2002) 949(1-2), 153-162.

What is claimed is:

1. An isotope coding agent comprising:
   a reactive functional group that reacts with an amine, a thiol, a hydroxyl or a carboxyl; and
   an isotopic linker comprising at least three heavy non-deuterium isotopes.

2. The isotope coding agent of claim 1 further comprising an affinity functional group for affinity selection.

3. The isotope coding agent of claim 1 wherein each heavy non-deuterium isotope is independently selected from the group consisting of $^{13}C$, $^{18}O$ and $^{15}N$.

4. The isotope coding agent of claim 1 wherein the heavy non-deuterium isotopes are identical.

5. The isotope coding agent of claim 1 comprising at least three $^{13}C$ isotopes.

6. The isotope coding agent of claim 1 comprising at least three $^{18}O$ isotopes.

7. The isotope coding agent of claim 1 wherein at least two of the heavy non-deuterium isotopes differ.

8. The isotope coding agent of claim 1 wherein the reactive functional group is iodoacetic acid or Iodoacetamide and wherein the affinity functional group is biotin.

9. An isotope coding agent comprising:
   a reactive functional group selected from the group consisting of iodoacetic acid and iodoacetamide;
   an isotopic linker having the structural formula $C_{10}H_{17}N_3O_3$ and comprising about nine $^{13}C$ isotopes; and
   a functional group for affinity selection comprising biotin.

10. An isotope coding agent comprising a compound selected from the group consisting of succinic anhydride, N-acetoxysuccinimide and propionate-N-hydroxysuccinimide, wherein the compound comprises at least three heavy non-deuterium isotopes.

11. An isotope coding agent comprising at least three $^{13}C$ isotopes, wherein the isotope coding agent reacts with an amine, a carboxyl, a hydroxyl or a thiol.

12. An isotope coding agent comprising at least three $^{18}O$ isotopes, wherein the isotope coding agent reacts with an amine, a carboxyl, a hydroxyl or a thiol.

13. An isotope coding agent comprising at least three $^{15}N$ isotopes, wherein the isotope coding agent reacts with an amine, a carboxyl, a hydroxyl or a thiol.

14. A method for isotopically coding an analyte, the method comprising:
   covalently linking the analyte to an isotope coding agent, wherein the isotope coding agent comprises a reactive functional group that reacts with an amine, a thiol, a hydroxyl or a carboxyl; and an isotopic linker comprising at least at least three heavy isotopes independently selected from the group consisting of $^{13}C$, $^{18}O$ and $^{15}N$.

* * * * *

UNITED STATES PATENT AND TRADEMARK OFFICE
CERTIFICATE OF CORRECTION

PATENT NO. : 7,449,170 B2
APPLICATION NO. : 10/256326
DATED : November 11, 2008
INVENTOR(S) : Regnier et al.

It is certified that error appears in the above-identified patent and that said Letters Patent is hereby corrected as shown below:

Title Page, Item
(74) Attorney, Agent or Firm
Delete "Meuting" and insert --Mueting--

Delete Drawing Sheets 1-10, and replace with Drawing Sheets 1-10. (attached)

Column 55, Line 40, Claim 8
Delete "Iodoacelamide" and insert --iodoacetamide--

Signed and Sealed this

Thirty-first Day of March, 2009

JOHN DOLL
*Acting Director of the United States Patent and Trademark Office*